United States Patent [19]

Farge et al.

[11] 4,415,562

[45] * Nov. 15, 1983

[54] 3-THIOVINYLCEPHALOSPORINS AND PHARMACEUTICAL COMPOSITIONS

[75] Inventors: Daniel Farge; Pierre L. Roy, both of Thiais; Claude Moutonnier, Le Plessis Robinson; Jean-François Peyronel, Palaiseau, all of France

[73] Assignee: Rhone-Poulenc Industries, Paris, France

[*] Notice: The portion of the term of this patent subsequent to Dec. 22, 1998 has been disclaimed.

[21] Appl. No.: 322,901

[22] Filed: Nov. 19, 1981

[30] Foreign Application Priority Data

Nov. 20, 1980 [FR] France ................... 80 24633

[51] Int. Cl.³ .................. A61K 31/545; C07D 501/24
[52] U.S. Cl. .................... 424/246; 542/413; 544/27
[58] Field of Search ............ 424/246; 542/413; 544/27

[56] References Cited

U.S. PATENT DOCUMENTS 4,307,116 12/1981 Farge et al. ............... 544/27

Primary Examiner—Paul M. Coughlan, Jr.
Attorney, Agent, or Firm—Stevens, Davis, Miller & Mosher

[57] ABSTRACT

New cephalosporins of the general formula:

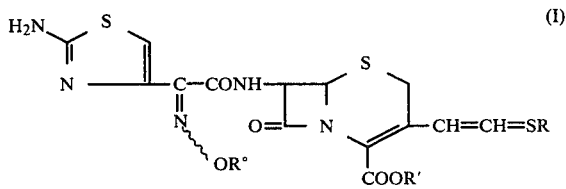

in which R is alkyl, L-2-amino-2-carboxyethyl, phenyl or various heterocyclic rings, R' is a hydrogen atom or a radical of the general formula:

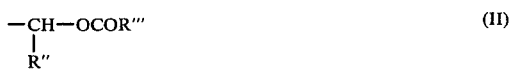

and R° is hydrogen, alkyl, vinyl, cyanomethyl or a carboxyalkyl radical of the general formula:

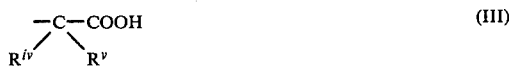

and also their salts, their preparation and the pharmaceutical compositions in which they are present.

16 Claims, No Drawings

3-THIOVINYLCEPHALOSPORINS AND PHARMACEUTICAL COMPOSITIONS

The present invention relates to new 3-thiovinylcephalosporins of the general formula:

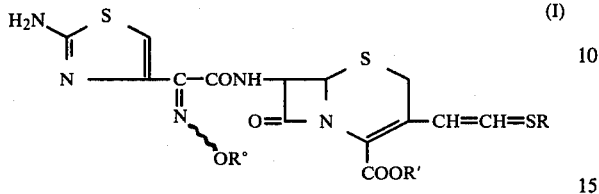

their salts, their preparation and the pharmaceutical compositions in which they are present.

The French Patent Application published under Nos. 2,081,451 and 2,137,899 described cephalosporins carrying, in the 3-position, a vinyl radical which can be substituted by aliphatic or aromatic radicals.

The products according to the invention are characterised in that, in the general formula (I), the symbol R' represents a hydrogen atom or a radical which can easily be removed by an enzymatic method and which has the general formula:

in which R″ represents a hydrogen atom or an alkyl radical and R‴ represents an alkyl radical or the cyclohexyl radical, and α. the symbol R is chosen from amongst the following meanings:

(1) alkyl, L-2-amino-2-carboxyethyl or phenyl, (2) pyrid-2-yl, pyrid-3-yl or pyrid-4-yl and their N-oxides, (3) pyrimidin-2-yl, pyridazin-3-yl substituted in the 6-position (by an alkyl, methoxy, amino or acylamino radical) and optionally N-oxidised, or tetrazolo[4,5-b]pyridazin-6-yl, (4) 5,6-dioxo-1,4,5,6-tetrahydro-1,2,4-triazin-3-yl substituted in the 4-position, or 1,3,4-triazol-5-yl or 2-alkoxycarbonyl-1,3,4-triazol-5-yl substituted in the 1-position, by (a) an alkyl radical which is unsubstituted or substituted by an alkoxy, alkylthio, phenyl, formyl, carbamoyl, alkylcarbamoyl, dialkylcarbamoyl, acyl, alkoxycarbonyl or thiazolidin-2-yl radical, (b) an allyl, 2,3-dihydroxypropyl, 1,3-dihydroxyprop-2-yl, 2-formyl-2-hydroxyethyl, 3-formyloxy-2-hydroxypropyl, 2,3-bis-formyloxypropyl or 1,3-bis-formyloxyprop-2-yl radical, (c) an alkyl radical containing 2 to 4 carbon atoms, which is substituted by a hydroxyl or carbamoyloxy radical, an acyloxy radical (the acyl part of which can be substituted by an amino, alkylamino or dialkylamino radical), an alkylsulphinyl, alkylsulphonyl, amino, alkylamino, dialkylamino, sulphoamino, alkylsulphonylamino or sulphamoylamino radical, an acylamino radical (the acyl part of which is optionally substituted by hydroxyl, amino, alkylamino or dialkylamino) or an alkoxycarbonylamino, ureido, alkylureido or dialkylureido radical, (d) a radical corresponding to one of the general formulae:

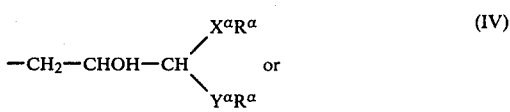

in which alk is an alkylene radical containing 1 to 4 carbon atoms, $X^\alpha$ and $Y^\alpha$ are identical and represent oxygen or sulphur atoms and $R^\alpha$ represents an alkyl radical, or alternatively $X^\alpha$ and $Y^\alpha$ are identical or different and represent oxygen or sulphur atoms and the radicals $R^\alpha$ together form an alkylene radical containing 2 or 3 carbon atoms, and $R^\beta$ represents a hydrogen atom or an alkyl radical containing 1 to 3 carbon atoms, or (e) an alkyl radical containing 2 to 5 carbon atoms, which is substituted by an alkoxyimino or hydroxyimino radical, (5) 1,4-dialkyl-5,6-dioxo-1,4,5,6-tetrahydro-1,2,4-triazin-3-yl, 1-alkyl-5,6-dioxo-1,4,5,6-tetrahydro-1,2,4-triazin-3-yl or 2-alkyl-5,6-dioxo-1,2,5,6-tetrahydro-1,2,4-triazin-3-yl, (6) 1,3,4-triazol-5-yl, 1,2,3-triazol-5-yl or 1-alkyl-1,2,4-triazol-5-yl which is unsubstituted or substituted in the 3-position by alkoxycarbonyl, (7) (a) 1,3,4-thiadiazol-5-yl which is unsubstituted or substituted by an alkyl, trifluoromethyl, alkoxy or alkylthio radical, a hydroxyalkylthio radical, the alkyl part of which contains 2 to 4 carbon atoms, or an alkylsulphonyl, hydroxyl, hydroxyalkyl, carboxyl, carboxyalkyl, amino, alkylamino, dialkylamino, aminoalkyl, alkylaminoalkyl, dialkylaminoalkyl, acylamino or acylaminoalkyl radical, or (b) 1,2,4-thiadiazol-5-yl substituted by an alkyl or alkoxy radical, (8) (a) 1,3,4-oxadiazol-5-yl which is unsubstituted or substituted by an alkyl, trifluoromethyl, phenyl, aminoalkyl, alkylaminoalkyl, dialkylaminoalkyl or acylaminoalkyl radical, or (b) oxazol-2-yl or 4-alkyloxazol-2-yl, and (9) tetrazol-5-yl which is unsubstituted or substituted in the 1-position by (a) an alkyl radical which is unsubstituted or substituted by alkoxy, sulpho, carboxyl, formyl or sulphamoyl, (b) an alkyl radical containing 2 to 4 carbon atoms, which is substituted by hydroxyl, amino, alkylamino, dialkylamino, acylamino, carboxyalkylamino, sulphamoylamino, sulphoamino, ureido, alkylureido or dialkylureido, (c) an alkyl radical containing 2 to 5 carbon atoms, which is substituted by hydroxyimino or alkoxyimino, (d) a phenyl, 2,3-dihydroxypropyl, 1,3-dihydroxyprop-2-yl, 2-formyl-2-hydroxyethyl, 3-formyloxy- 2-hydroxypropyl, 2,3-bis-formyloxypropyl or 1,3-bis-formyloxyprop-2-yl radical, or (e) a radical of the general formula:

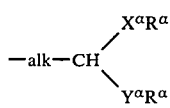  (IIIa)

in which alk, $X^\alpha$, $Y^\alpha$ and $R^\alpha$ are defined as above, or a radical of the general formula (IV), and the symbol R° represents a carboxyalkyl radical of the general formula:

  (VI)

in which the radicals $R^{iv}$ and $R^v$, which are identical or different, represent hydrogen atoms or alkyl radicals, or together form an alkylene radical containing 2 or 3 carbon atoms, or alternatively β. R is chosen from amongst:

1. 5,6-dioxo-1,4,5,6-tetrahydro-1,2,4-triazin-3-yl substituted in the 1-position, 5,6-dioxo-1,2,5,6-tetrahydro-1,2,4-triazin-3-yl substituted in the 2-position, or 1,2,4-triazol-5-yl or 3-alkoxycarbonyl-1,2,4-triazol-5-yl substituted in the 1-position, by (a) an alkyl radical substituted by an alkoxy, alkylthio, phenyl, formyl, carbamoyl, alkylcarbamoyl or dialkylcarbamoyl radical, a hydroxyalkylcarbamoyl radical (the alkyl part of which contains 2 to 4 carbon atoms) or an acyl, alkoxycarbonyl or thiazolidin-2-yl, radical, (b) an allyl, 2,3-dihydroxypropyl, 1,3-dihydroxyprop-2-yl, 2-formyl-2-hydroxyethyl, 3-formyloxy-2-hydroxypropyl, 2,3-bis-formyloxypropyl or 1,3-bis-formyloxyprop-2-yl radical, (c) an alkyl radical containing 2 to 4 carbon atoms, which is substituted by a hydroxyl or carbamoyloxy radical, an acyloxy radical (the acyl part of which can be substituted by an amino, alkylamino or dialkylamino radical), an alkylsulphinyl, alkylsulphonyl, amino, alkylamino, dialkylamino, sulphoamino, alkylsulphonylamino or sulphamoylamino radical, an acylamino radical (the acyl part of which is optionally substituted by hydroxyl, amino, alkylamino or dialkylamino) or an alkoxycarbonylamino, ureido, alkylureido or dialkylureido radical, (d) a radical corresponding to one of the general formulae (III), (IV) or (V) as defined above, or (e) an alkyl radical containing 2 to 5 carbon atoms, which is substituted by an alkoxyimino or hydroxyimino radical, 2. 5,6-dioxo-4-hydroxyalkylcarbamoylalkyl-1,4,5,6-tetrahydro-1,2,4-triazin-3-yl, the hydroxyalkyl portion of which contains 2 to 4 carbon atoms, and 3. 1-alkyl-5,6-dioxo-1,4,5,6-tetrahydro-1,2,4-triazin-3-yl substituted in the 4-position, 1-alkyl-5,6-dioxo-1,2,5,6-tetrahydro-1,2,4-triazin-3-yl substituted in the 2-position, 2-alkyl-5,6-dioxo-1,2,5,6-tetrahydro-1,2,4-triazin-3-yl substituted in the 1-position, or 4-alkyl-5,6-dioxo-1,4,5,6-tetrahydro-1,2,4-triazin-3-yl substituted in the 1-position, by a formylalkyl radical or by a radical of the general formula (IIIa), and R° represents a hydrogen atom, an alkyl, vinyl or cyanomethyl radical or a radical of the general formula (VI).

Unless otherwise mentioned, the alkyl or acyl portions or radicals mentioned in the present description contain 1 to 4 carbon atoms in a linear or branched chain.

The substituent in the 3-position of the products of the general formula (I) can be in the cis or trans form or as a mixture of the cis and trans forms.

In the following text, the trans stereoisomer is designated by E and the cis stereoisomer is designated by Z.

Furthermore, the group OR° can be in either the syn or anti position.

The syn form is represented by the formula:

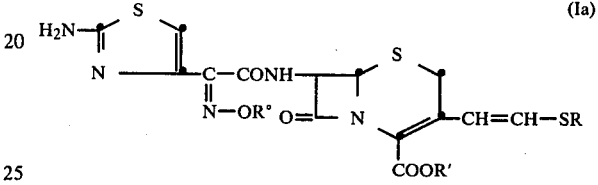  (Ia)

The anti form is represented by the formula:

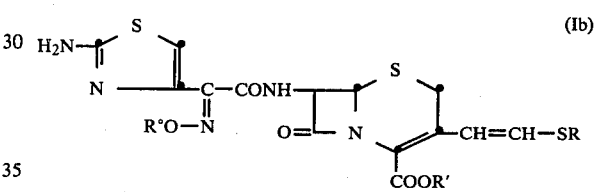  (Ib)

Likewise, if the radical R contains a hydroxyiminoalkyl or alkoxyiminoalkyl substituent, this group exhibits syn/anti isomerism.

If the radical R is a 1,4,5,6-tetrahydrotriazinyl radical substituted in the 1-position or 4-position or a 1,2,5,6-tetrahydrotriazinyl radical substituted in the 2-position, it is represented by the tautomeric forms:

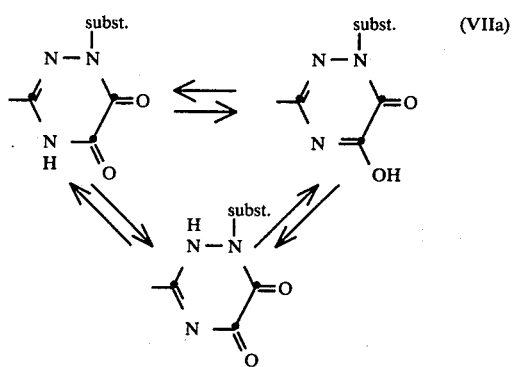  (VIIa)

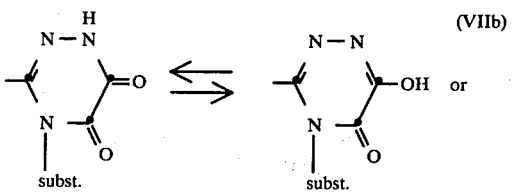  (VIIb)

-continued

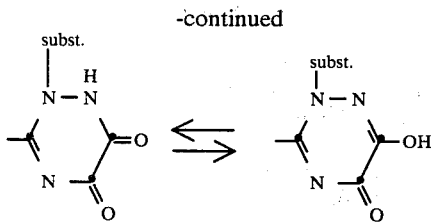
(VIIc)

Furthermore, if the symbols $R^{iv}$ and $R^v$ in the general formula (VI) are different, diastereoisomers exist.

It is understood that all the isomeric forms and mixtures thereof fall within the scope of the present invention.

If the radical R contains a formylalkyl substituent, it is in the form of the free aldehyde or the aldehyde hydrate. These forms are observed, in particular, under the conditions described below.

The nuclear magnetic resonance studies show, in particular, that if R is 5,6-dioxo-4-formylmethyl-1,4,5,6-tetrahydro-1,2,4-triazin-3-yl:

in an acid solvent such as (deuterated) formic or trifluoroacetic acid, in the presence or absence of (heavy) water, the product is mainly in the form of the free aldehyde;

in a basic solvent such as (heavy) water to which sodium bicarbonate has been added, it is mainly in the form of the aldehyde hydrate; and in a neutral solvent such as dimethyl sulphoxide ($d_6$), the free aldehyde form and the aldehyde hydrate form are present, the addition of water displacing the equilibrium in favouring the aldehyde hydrate form.

The products of the general formula (Ia) are the preferred products.

Amongst the meanings of the symbol R° above, the following may be mentioned in particular: hydrogen, methyl, ethyl, propyl, isopropyl, butyl, isobutyl, sec.-butyl, vinyl, cyanomethyl, carboxymethyl, 1-carboxyethyl, 2-carboxyprop-2-yl, 1-carboxycyclopropyl and 1-carboxycyclobutyl.

Amongst the meanings of the symbol R above, the following may be mentioned in particular: 1-methyl-1,3,4-thiadiazol-5-yl, 2-(2-acetamidoethyl)-1,3,4-thiadiazol-5-yl, 2-dimethylaminomethyl-1,3,4-thiadiazol-5-yl, 1-formylmethyl-1,2,4-triazol-5-yl, 1-formylmethyl-1,3,4-triazol-5-yl, 1-formylmethyl-2-methoxycarbonyl-1,3,4-triazol-5-yl, 1-methyltetrazol-5-yl, 1-(2-acetylaminoethyl)-tetrazol-5-yl, 1-formylmethyltetrazol-5-yl, 1-(2-hydroxyethyl)-tetrazol-5-yl, 1-(2-dimethylaminoethyl)tetrazol-5-yl, primidin-2-yl, pyrid-2-yl, pyrid-2-yl-N-oxide, pyrid-3-yl, pyrid-4-yl, 6-methylpyridazin-3-yl-1-oxide, 5,6-dioxo-1-methyl-1,4,5,6-tetrahydro-1,2,4-triazin-3-yl, 5,6-dioxo-2-methyl-1,2,5,6-tetrahydro-1,2,4-triazin-3-yl, 5,6-dioxo-4-methyl-1,4,5,6-tetrahydro-1,2,4-triazin-3-yl, 5,6-dioxo-1-ethyl-1,4,5,6-tetrahydro-1,2,4-triazin-3-yl, 5,6-dioxo-1-formylmethyl-1,4,5,6-tetrahydro-1,2,4-triazin-3-yl, 5,6-dioxo-2-formylmethyl-1,2,5,6-tetrahydro-1,2,4-triazin-3-yl, 5,6-dioxo-4-formylmethyl-1,4,5,6-tetrahydro-1,2,4-triazin-3-yl, 5,6-dioxo-1-(2-hydroxyethyl)-1,4,5,6-tetrahydro-1,2,4-triazin-3-yl, 5,6-dioxo-2-(2-hydroxyethyl)-1,2,5,6-tetrahydro-1,2,4-triazin-3-yl, 5,6-dioxo-4-(2-hydroxyethyl)-1,4,5,6-tetrahydro-1,2,4-triazin-3-yl, 5,6-dioxo-1-(2-methoxyethyl)-1,4,5,6-tetrahydro-1,2,4-triazin-3-yl, 5,6-dioxo-2-(2-methoxyethyl)-1,2,5,6-tetrahydro-1,2,4-triazin-3-yl, 5,6-dioxo-4-(2-methoxyethyl)-1,4,5,6-tetrahydro-1,2,4-triazin-3-yl, 5,6-dioxo-1-(2-methylthioethyl)-1,4,5,6-tetrahydro-1,2,4-triazin-3-yl, 5,6-dioxo-2-(2-methylthioethyl)-1,2,5,6-tetrahydro-1,2,4-triazin-3-yl, 5,6-dioxo-4-(2-methylthioethyl)-1,4,5,6-tetrahydro-1,2,4-triazin-3-yl, 1-(2-acetamidoethyl)-5,6-dioxo-1,4,5,6-tetrahydro-1,2,4-triazin-3-yl, 2-(2-acetamidoethyl)-5,6-dioxo-1,2,5,6-tetrahydro-1,2,4-triazin-3-yl, 4-(2-acetamidoethyl)-5,6-dioxo-1,4,5,6-tetrahydro-1,2,4-triazin-3-yl, 5,6-dioxo-1-(2-formyl-2-hydroxyethyl)-1,4,5,6-tetrahydro-1,2,4-triazin-3-yl, 5,6-dioxo-2-(2-formyl-2-hydroxyethyl)-1,2,5,6-tetrahydro-1,2,4-triazin-3-yl, 5,6-dioxo-4-(2-formyl-2-hydroxyethyl)-1,4,5,6-tetrahydro-1,2,4-triazin-3-yl, 1-(2,3-dihydroxypropyl)-5,6-dioxo-1,4,5,6-tetrahydro-1,2,4-triazin-3-yl, 4-(2,3-dihydroxypropyl)-5,6-dioxo-1,4,5,6-tetrahydro-1,2,4-triazin-3-yl, 5,6-dioxo-4-(2-methoxy-2-hydroxyethyl)-1,4,5,6-tetrahydro-1,2,4-triazin-3-yl, 5,6-dioxo-4-(2-ethoxy-2-hydroxyethyl)-1,4,5,6-tetrahydro-1,2,4-triazin-3-yl, 5,6-dioxo-4-(2-formyloxyethyl)-1,4,5,6-tetrahydro-1,2,4-triazin-3-yl, 4-(2-carbamoyloxyethyl)-5,6-dioxo-1,4,5,6-tetrahydro-1,2,4-triazin-3-yl, 4-allyl-5,6-dioxo-1,4,5,6-tetrahydro-1,2,4-triazin-3-yl, 1-allyl-5,6-dioxo-1,4,5,6-tetrahydro-1,2,4-triazin-3-yl, 2-allyl-5,6-dioxo-1,2,5,6-tetrahydro-1,2,4-triazin-3-yl, 5,6-dioxo-4-(2-glycylaminoethyl)-1,4,5,6-tetrahydro-1,2,4-triazin-3-yl, 5,6-dioxo-1-(2-glycylaminoethyl)-1,4,5,6-tetrahydro-1,2,4-triazin-3-yl, 5,6-dioxo-4-(2-methanesulphonylaminoethyl)-1,4,5,6-tetrahydro-1,2,4-triazin-3-yl, 5,6-dioxo-1-(2-methanesulphonylaminoethyl)-1,4,5,6-tetrahydro-1,2,4-triazin-3-yl, 5,6-dioxo-4-[2-(3-methylureido)-ethyl]-1,4,5,6-tetrahydro-1,2,4-triazin-3-yl, 5,6-dioxo-1-[2-(3-methylureido)-ethyl]-1,4,5,6-tetrahydro-1,2,4-triazin-3-yl, 4-carbamoylmethyl-5,6-dioxo-1,4,5,6-tetrahydro-1,2,4-triazin-3-yl, 4-dimethylcarbamoylmethyl-5,6-dioxo-1,4,5,6-tetrahydro-1,2,4-triazin-3-yl, 4-[N-(2-hydroxyethyl)-carbamoylmethyl]-5,6-dioxo-1,4,5,6-tetrahydro-1,2,4-triazin-3-yl, 5,6-dioxo-1-formylmethyl-4-methyl-1,4,5,6-tetrahydro-1,2,4-triazin-3-yl, 5,6-dioxo-2-formylmethyl-1-methyl-1,2,5,6-tetrahydro-1,2,4-triazin-3-yl, 5,6-dioxo-4-formylmethyl-1-methyl-1,4,5,6-tetrahydro-1,2,4-triazin-3-yl, 5,6-dioxo-1-formylmethyl-2-methyl-1,2,5,6-tetrahydro-1,2,4-triazin-3-yl, 5,6-dioxo-2-formylmethyl-1-methyl-1,2,5,6-tetrahydro-1,2,4-triazin-3-yl, 5,6-dioxo-1-ethyl-4-formylmethyl-1,4,5,6-tetrahydro-1,2,4-triazin-3-yl and 5,6-dioxo-4-ethyl-1-formylmethyl-1,4,5,6-tetrahydro-1,2,4-triazin-3-yl.

Amongst the meanings of the symbol R' above, hydrogen, pivaloyloxymethyl and acetoxymethyl may be mentioned in particular.

A. According to the invention, the products of the general formula (I) in which R is other than a triazinyl or triazolyl radical substituted by a group of the general formula (V) can be prepared by reacting an acid of the general formula:

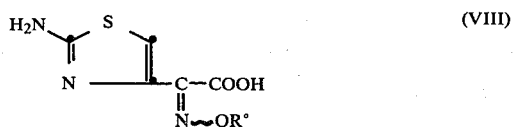
(VIII)

in which R° is defined as above and in which the amine group has been protected beforehand [and also the oxime or the carboxyalkyl radical if R° represents hydrogen or a radical of the general formula (VI)], or a reactive derivative of this acid, with a 7-aminocephalosporin of the general formula:

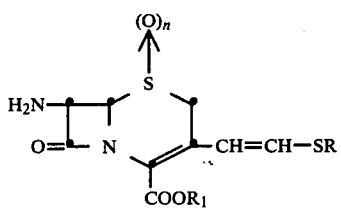

(IX)

[in which R is defined as above, except that it cannot represent a radical substituted by a group of the general formula (V), $R_1$ represents a hydrogen atom, a radical of the general formula (II) or a protective radical which can easily be removed, e.g. methoxymethyl, t-butyl, benzhydryl, nitrobenzyl or p-methoxybenzyl, and n represents 0 or 1], then reducing the sulphoxide obtained, if n=1, and then removing the protective radicals.

It is understood that the acid of the general formula (VIII) in the syn or anti form, or mixtures thereof, leads respectively to the products of the general formula (I) in the syn or anti form, or to mixtures thereof.

a. If the product of the general formula (VIII) is used in the acid form, the protection of the amino group is effected by any method which is in itself known for blocking an amine group without affecting the rest of the molecule. It is necessary to use a group which can easily be removed, such as a t-butoxycarbonyl, 2,2,2-trichloroethoxycarbonyl, chloroacetyl, trichloroacetyl, trityl, benzyl, dibenzyl, benzyloxycarbonyl, p-nitrobenzyloxycarbonyl, p-methoxybenzyloxycarbonyl, formyl or trifluoroacetyl group.

If R° represents a hydrogen atom, the protection of the oxime can be effected by any known method which does not affect the rest of the molecule. The trityl, tetrahydropyranyl or 2-methoxyprop-2-yl groups are used in particular.

If R° contains a carboxyl radical, it is necessary to protect this group by any known method which does not affect the rest of the molecule. A protective radical which can easily be removed, such as methoxymethyl, t-butyl, benzhydryl, benzyl, nitrobenzyl or p-methoxybenzyl, is used in particular.

In general, the condensation of the product of the general formula (VIII) in which the amine group has been protected beforehand, with the 7-aminocephalosporin of the general formula (IX) in which, R and n being defined as above, $R_1$ represents a radical of the general formula (II) or a protective radical which can easily be removed, such as methoxymethyl, t-butyl, benzhydryl, nitrobenzyl or p-methoxybenzyl, is carried out in an organic solvent such as dimethylformamide, acetonitrile, tetrahydrofuran, methylene chloride or chloroform, in the presence of a condensation agent such as a carbodiimide (e.g. dicyclohexylcarbodiimide), N,N'-carbonyldiimidazole or 2-ethoxy-1-ethoxycarbonyl-1,2-dihydroquinoline, at a temperature between −20° and 40° C., the oxide obtained if a 7-aminocephalosporin of the general formula (IX) in which n=1 has been used is reduced, and the protective groups of the amine group and, if necessary, of the acid groups and of the oxime are removed.

It is understood that the amino, alkylamino, carboxyl and hydroxyl groups which are present in some of the radicals R are or can be protected by any protective groups which are normally used for protecting amines, carboxylic acids or alcohols, and the use of which does not affect the rest of the molecule.

By way of examples:

the amino and alkylamino groups are protected by radicals such as t-butoxycarbonyl, 2,2,2-trichloroethoxycarbonyl, trichloroacetyl, trityl, benzyl, dibenzyl, benzyloxycrbonyl, p-nitrobenzyloxycarbonyl, p-methoxybenzyloxycarbonyl, chloroacetyl, formyl or trifluoroacetyl, the carboxyl groups can be protected by radicals such as methoxymethyl, t-butyl, benzhydryl, nitrobenzyl or p-methoxybenzyl, and the hydroxyl groups can be protected by radicals such as trityl, tetrahydropyranyl or 2-methoxyprop-2-yl, or alternatively in the form of a 2,2-dimethyldioxolan-4-yl-methyl or 2,2-dimethyldioxan-5-yl radical in the case of the protection of the 2,3-dihydroxypropyl or 1,3-dihydroxyprop-2-yl radicals.

It is also understood that if, in the general formula (IX), the radical R contains a hydroxyl, sulpho, sulphinyl or sulphonyl group, it is preferable to use a product in the formula of which n=0.

If it is desired to obtain a product of the general formula (I) in which R contains a formylalkyl or acylalkyl radical, this radical can be optionally protected as an acetal, in the form of a radical of the general formula (III), (IIIa) or (IV) as defined above.

The removal of the protective radical of R is carried out after the reduction of the oxide, before, simultaneously with or after the removal of the other protective radicals. The same applies to the other protective radicals present in the molecule.

The reduction of the S-oxide is carried out e.g. under the conditions described in German Patent Application No. 2,637,176. The removal of the various protective radicals can be carried out simultaneously or successively.

By way of example:

1. The removal of the amine-protecting groups is carried out:

in the case of a t-butoxycarbonyl, trityl, p-methoxybenzyloxycarbonyl or formyl radical: by treatment in an acid medium. Preferably, trifluoroacetic acid is used at a temperature between 0° and 20° C.; or alternatively formic acid, phosphoric acid or polyphosphoric acid pure or in the presence of water at between 20° and 60° C., or para-toluenesulphonic or methanesulphonic acid in acetone at the reflux temperature of the reaction mixture is used. Under these conditions, the product of the general formula (I) can be obtained in the form of the trifluoroacetate, the solvate with formic acid, the phosphate, the methanesulphonate or the para-toluenesulphonate, from which the amine group can be freed by any method which is in itself known for obtaining an amine from one of its salts without affecting the rest of the molecule. The reaction is carried out, in particular, by bringing the compound into contact with an ion exchange resin or by reaction with an organic base. In the case of a 2,2,2-trichloroethoxycarbonyl or p-nitrobenzyloxycarbonyl radical: by reduction (in particular treatment with zinc in acetic acid).

in the case of a chloroacetyl or trichloroacetyl radical: by applying the method described in the French Patent published under No. 2,243,199.

in the case of a benzyl, dibenzyl or benzyloxycarbonyl radical: by catalytic hydrogenation.

in the case of a trifluoroacetyl radical: by treatment in a basic medium.

2. The removal of the protective groups of the carboxyl radical is carried out:

in the case of a t-butyl, p-methoxybenzyl or benzhydryl group: by treatment in an acid medium, under the conditions described above for the removal of the amino-protecting trityl radical. In the case of the benzhydryl radical, the reaction can be carried out in the presence of anisole.

in the case of a methoxymethyl group: by treatment in a dilute acid medium.

in the case of a nitrobenzyl group: by reduction (in particular treatment with zinc in acetic acid or hydrogenolysis).

3. The removal of the protective groups of the oxime and/or of the hydroxyl radicals is carried out:

in the case of a trityl or tetrahydropyranyl group or the 2,2-dimethyldioxolan-4-yl-methyl or 2,2-dimethyldioxan-5-yl radicals: by acidolysis, e.g. with trifluoroacetic acid, aqueous or non-aqueous formic acid or paratoluenesulphonic acid. If aqueous or non-aqueous formic acid is used, the freeing of the hydroxyl radicals protected in the form of a cyclic acetal can lead at least partially to the corresponding formic acid monoesters or diesters, which can be separated off by chromatography, if necessary.

in the case of the 2-methoxyprop-2-yl group: in accordance with the method described in Belgian Pat. No. 875,379.

4. The freeing of the formylalkyl or acylalkyl radicals protected in the form of groups of the general formula (III), (IIIa) or (IV) (if it is desired to obtain a product of the general formula (I) in which R contains a formylalkyl or acylalkyl radical) is carried out:

in the presence of a sulphonic acid (e.g. methanesulphonic acid or para-toluenesulphonic acid), in an organic solvent (e.g. acetonitrile or acetone), if appropriate in the presence of water and if appropriate in the presence of a reagent which can be converted to an acetal, such as acetone, glyoxylic acid, benzaldehyde or pyruvic acid, at a temperature between 20° C. and the reflux temperature of the reaction mixture, or alternatively, if the radical R is a 5,6-dioxo-1,4,5,6-tetrahydro-1,2,4-triazin-3-yl or 5,6-dioxo-1,2,5,6-tetrahydro-1,2,4-triazin-3-yl radical, by reaction with pure or aqueous formic acid (preferably containing less than 10% of water), either in the presence or absence of silica, or by transacetalisation in the presence of a reagent which can be converted to an acetal, as defined above.

b. If a reactive derivative of the acid of the general formula (IX) is used, it is possible to use the anhydride, a mixed anhydride or a reactive ester of the general formula:

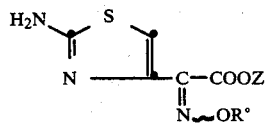
(X)

in which R° is defined as above and Z represents a succinimido, benzotriazol-1-yl, 4-nitrophenyl, 2,4-dinitrophenyl, pentachlorophenyl or phthalimido radical, the amine group of such derivatives and, if necessary, the radical R° having been protected beforehand (e.g. as described above under a). It is also possible to use reactive derivatives such as thioloester as defined below by the general formula (XV), or an acid halide. In the latter case, it is possible to react the hydrochloride of the acid chloride with the 7-aminocephalosporin of the general formula (IX).

If the anhydride, a mixed anhydride or an acid halide (which can all be prepared in situ) is used, the condensation is carried out in an inert organic solvent such as an ether (e.g. tetrahydrofuran or dioxane), a chlorinated solvent (e.g. chloroform or methylene chloride), an amide (e.g. dimethylformamide or dimethylacetamide) or a ketone (e.g. acetone), or in mixtures of the above solvents, in the presence of an acid acceptor such as an epoxide (e.g. propylene oxide) or such as a nitrogen-containing organic base like pyridine, dimethylaminopyridine, N-methylmorpholine or a trialkylamine (e.g. triethylamine), or in an aqueous-organic medium, in the presence of an alkaline condensation agent such as sodium bicarbonate, and the reaction is carried out at a temperature between −40° and +40° C., the S-oxide obtained is then reduced, if necessary, and the protective groups are replaced by hydrogen atoms, if appropriate.

If a reactive ester of the general formula (X) or a thioloester of the general formula (XV) is used, the reaction is generally carried out in the presence of a trialkylamine (triethylamine), in an organic solvent such as dimethylformamide, at a temperature between 0° and 40° C., the S-oxide obtained is then reduced, if necessary, and the protective groups are replaced by hydrogen atoms.

B. According to the invention, the products of the general formula (I) in which R, R° and R' are defined as above, except that R cannot contain a substituent of the general formula (V), can also be prepared by reacting a thiol (or one of its alkali metal or alkaline earth metal salts) of the general formula:

R—SH (XI)

{in which R, which is defined as above, is protected in the form of an acetal [as defined by the general formulae (III), (IIIa) or (IV)] if it is desired to obtain a cephalosporin of the general formula (I) in which R contains a formyl or acylalkyl radical} with a cephalosporin derivative (or, if necessary, with a mixture of the isomers of this derivative) of the general formula:

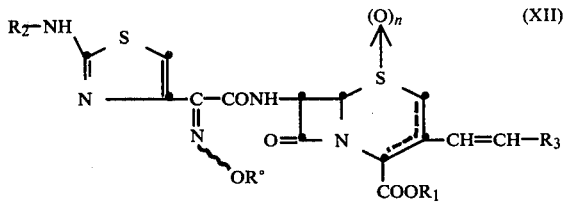
(XII)

in which, R°, R₁ and n being defined as above, if n=0, the product is in the form of a bicyclooct-2-ene or bicyclooct-3-ene, and if n=1, the product is in the form of a bicyclooct-2-ene (according to the nomenclature of Chemical Abstracts), the substituent on the carbon atom in the 3-position of the bicyclooctene exhibits E/Z stereoisomerism, R₂ represents a hydrogen atom or a protective radical of the amino group, as defined above under A., and R₃ represents a halogen atom chosen from amongst chlorine, bromine and iodine, or a radical of the general formula:

—O—SO₂—R'₃ (XIIIa)

or $$-O-CO-R''_3 \quad \text{(XIIIb)}$$

in which formulae $R'_3$ is an alkyl, trifluoromethyl or trichloromethyl radical or a phenyl radical optionally substituted by a halogen atom or by an alkyl or nitro radical, and $R''_3$ is defined in the same way as $R'_3$ or represents an acylmethyl, 2-acylethyl, 2-acylpropyl, alkoxycarbonylmethyl, 2-alkoxycarbonylethyl or 2-alkoxycarbonylpropyl radical, then reducing the oxide obtained (if $n=1$) and then removing the protective radicals, if appropriate.

It is understood that, if the radical R of the product of the general formula (XI) is capable of interfering with the reaction, it is preferable to protect this group under the conditions described above (in particular if R contains an amino, alkylamino, hydroxyl or carboxyl radical).

It is also understood that, if $R°$ represents hydrogen or a radical of the general formula (VI), it is preferable to protect the oxime or the carboxyl radical under the conditions described above.

It is also understood that, if the radical R is likely to interfere with the reduction reaction, it is preferable to use a product of the general formula (XII) in which $n=0$ (in particular if R comprises a hydroxyl, sulpho, sulphinyl or sulphonyl group).

The reaction is generally carried out in the presence of an organic base such as a pyridine or a tertiary organic base of the general formula:

$$X_1-N\begin{matrix}Y_1\\Z_1\end{matrix} \quad \text{(XIV)}$$

in which $X_1$, $Y_1$ and $Z_1$ represent alkyl or phenyl radicals or, if appropriate, two of them form a ring with the nitrogen atom to which they are attached. The organic base used is e.g. diisopropylethylamine or diethylphenylamine.

If an alkali metal salt or alkaline earth metal salt of the thiol of the general formula (XI) is reacted, it is not necessary to carry out the reaction in the presence of an organic base as defined above.

The reaction is advantageously carried out in an organic solvent such as dimethylformamide, tetrahydrofuran, ethanol, methanol or acetonitrile, or a mixture of the abovementioned solvents.

It is also possible to carry out the reaction in the presence of an alkali metal bicarbonate, in a solvent such as mentioned above, if appropriate in the presence of water.

The reaction is carried out at a temperature between $-20°$ C. and the reflux temperature of the reaction mixture, the chosen temperature varying according to the thiol employed. Likewise, the reaction time can vary from 5 minutes to 48 hours, according to the thiol employed.

If appropriate, the reaction is carried out under nitrogen.

Preferably, if it is desired to use a bicyclooct-3-ene of the general formula (XII), a product of this type in which $R_1$ is other than hydrogen is used.

The reduction of the oxide and the removal of the protective groups are carried out in accordance with the methods described above.

C. According to the invention, the products of the general formula (I) in which R, R° and R' are defined as above, R being other than a triazinyl or triazolyl radical substituted by a group of the general formula (V), can also be prepared by reacting a thioloester of the general formula:

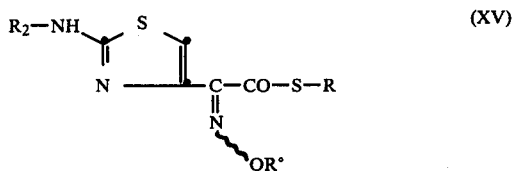

(XV)

in which R° and $R_2$ are defined as above (it being understood that, if R° contains a carboxyl radical, the latter is protected, and that, if R° represents a hydrogen atom, the oxime has been protected beforehand) and R is defined as above [it being understood that, if it contains an amino or alkylamino substituent, the latter is protected, if it contains a hydroxyl or carboxyl substituent, the latter is free or protected, and if it contains a formyl or acylalkyl substituent, the latter is protected in the form of an acetal as in the general formula (III), (IIIa) or (IV)], with a 7-aminocephalosporin of the general formula:

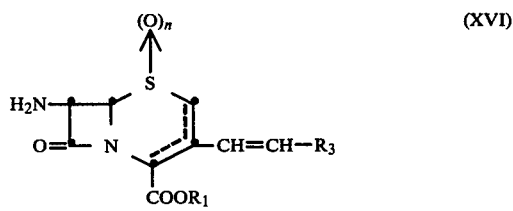

(XVI)

in which $R_1$, $R_3$ and n are defined as above and which exhibits the stereoisomerism defined above for the product of the general formula (XII), then reducing the sulphoxide obtained if $n=1$, and removing the protective radicals, if necessary.

As for process A., it is understood that the thioloesters in the syn or anti form, or mixtures thereof, lead respectively to the products of the general formula (I) in the syn or anti form, or to mixtures thereof.

Likewise, as for the processes described above, if R contains a hydroxyl, sulpho, sulphinyl or sulphonyl substituent, it is preferred to use a product of the general formula (XVI) in which $n=0$.

The protection and the removal of the protective radicals are carried out under the conditions described above.

The reaction of the thioloester with the 7-aminocephalosporin of the general formula (XVI) is generally carried out in the presence of an acid acceptor such as an organic base, more particularly in the presence of a pyridine or a tertiary organic base of the general formula (XIV), in particular triethylamine, N,N-diisopropyl-N-ethylamine, diethylphenylamine or N-methylmorpholine.

The reaction is advantageously carried out in an organic solvent such as an amide (e.g. dimethylformamide or dimethylacetamide), an ether (e.g. tetrahydrofuran or dioxane), a chlorinated solvent (e.g. chloroform or methylene chloride), a ketone (e.g. acetone) or a nitrile (e.g. acetonitrile), or alternatively in a mixture of these solvents. It is also possible to carry out the reaction in the presence of an alkali metal bicarbonate, in one of the abovementioned solvents, if appropriate in the presence of water.

The reaction is carried out at a temperature between ates, alkali metal salts of carboxylic acids (sodium formate or sodium acetate) or tertiary amines (triethylamine, trimethylamine or pyridine), at a temperature between −30° and 60° C.

If the reaction is carried out in the presence of a base, depending on the nature of the latter and the amount introduced, the intermediate of the general formula:

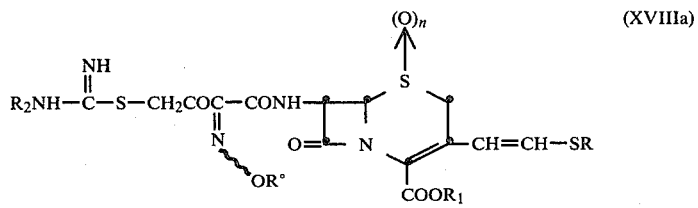

(XVIIIa)

−20° C. and the reflux temperature of the reaction mixture. If appropriate, it is carried out under nitrogen.

The reduction of the S-oxide is carried out under the conditions described above.

D. According to the invention, the products of the general formula (I) [in which R° and R' are defined as above, except that R° cannot represent the vinyl radical, and R is defined as above, except that it cannot represent a triazinyl or triazolyl radical substituted by a group of the general formula (V)] can be prepared by reacting a thiourea of the general formula:

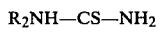 (XVII)

(in which $R_2$ is defined as above under B., except that it cannot represent chloroacetyl or trichloroacetyl) with a product of the general formula:

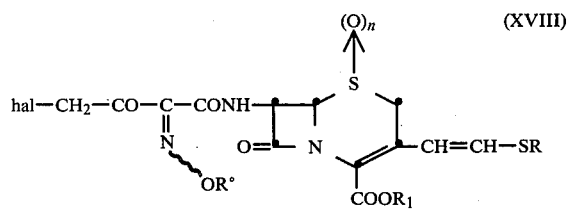

(XVIII)

in which R°, R, $R_1$ and n are defined as above and hal represents a chlorine or bromine atom, and then, if necessary, reducing the sulphoxide and removing the protective radicals.

The reaction is generally carried out in an aqueous, organic or aqueous-organic medium, e.g. in solvents or mixtures of solvents such as alcohols (methanol or ethanol), ketones (acetone), chlorinated solvents (chloroform or methylene chloride), nitriles (acetonitrile), amides (dimethylformamide or dimethylacetamide), ethers (tetrahydrofuran or dioxane), esters (ethyl acetate) or acids (acetic acid or formic acid), in the presence or absence of a base such as sodium hydroxide, potassium hyroxide, alkali metal carbonates, alkali metal bicarbonin which R°, R, $R_1$, $R_2$ and n are defined as above, may or may not be isolated, and this can then be cyclised in an acid medium.

It is understood that, if R° contains a carboxyl radical, the latter can be free or protected.

If it is desired to obtain a product of the general formula (I) in which R contains a formylalkyl or acylalkyl radical, this radical can be protected as an acetal, in the form of a radical of the general formula (III), (IIIa) or (IV), as defined above.

The reduction of the sulphoxide and the removal of the protective radicals are carried out under the conditions described above.

E. According to the invention, the products of the general formula (I) in which, R° and R' being defined as above, R represents a 5,6-dioxo-1,4,5,6-tetrahydro-1,2,4-triazin-3-yl radical substituted in the 1-position or 4-position, a 5,6-dioxo-1,2,5,6-tetrahydro-1,2,4-triazin-3-yl radical substituted in the 2-position, or a 1,3,4-triazol-5-yl, 2-alkoxycarbonyl-1,3,4-triazol-5-yl, 1,2,4-triazol-5-yl or 3-alkoxycarbonyl-1,2,4-triazol-5-yl radical substituted in the 1-position, by an alkyl radical containing 2 to 4 carbon atoms, which is substituted by a carbamoyloxy group or an acyloxy group (the acyl part of which is optionally substituted by an amino, alkylamino or dialkylamino radical), which are esters of the corresponding alcohol of the general formula (I) in which R° and R' are defined as above and R is a radical -Ⓡ-alk'-OH chosen from amongst 5,6-dioxo-1-(or 4-)-hydroxyalkyl-1,4,5,6-tetrahydro-1,2,4-triazin-3-yl, 5,6-dioxo-2-hydroxyalkyl-1,2,5,6-tetrahydro-1,2,4-triazin-3-yl, 1-hydroxyalkyl-1,3,4-triazol-B 5-yl, 2-alkoxycarbonyl-1-hydroxyalkyl-1,3,4-triazol-5-yl, 1-hydroxyalkyl-1,2,4-triazol-5-yl or 3-alkoxycarbonyl-1-hydroxyalkyl-1,2,4-triazol-5-yl, can be obtained by the carbamoylation or esterification of an alcohol of the general formula:

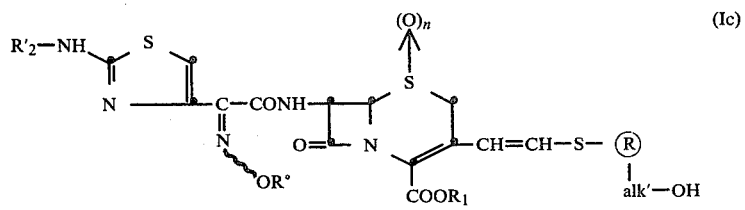

(Ic)

(in which R°, $R_1$, Ⓡ-alk'-OH and n are defined as above, it being understood that R° can be free or protected, and $R'_2$ is defined in the same way as $R_2$, except that it cannot represent hydrogen) by any method known for obtaining an ester or a carbamate from an alcohol without affecting the rest of the molecule, this being followed, if necessary, by the reduction of the sulphoxide obtained and the removal of the protective radicals.

The esterification is carried out at a temperature between −50° C. and the reflux temperature of the reaction mixture, in particular by condensation of the acid anhydride (or of another reactive derivative, e.g. a halide), in an inert organic solvent such as an ether (e.g. tetrahydrofuran), a chlorinated solvent (e.g. methylene chloride) or a mixture of these solvents, in the presence of a nitrogen-containing base such as pyridine, 4-dimethylaminopyridine or a trialkylamine (triethylamine), or of an alkaline condensation agent (e.g. sodium bicarbonate), this being followed, if necessary, by the reduction of the S-oxide obtained and the removal of the protective groups, in accordance with the methods described above.

If the acyloxy group contains one carbon atom and is substituted by amino (carbamoyloxy group), the reaction is carried out in particular with chlorosulphonyl or trichloroacetyl isocyanate, in an inert organic solvent, e.g. tetrahydrofuran or acetonitrile, at a temperature between −80° and 20° C., this being followed by the removal of the protective groups.

The products of the general formula (Ic) can be obtained in accordance with one or other of the processes described above.

F. According to the invention, the products of the general formula (I) in which, R° and R' being defined as above, R represents a 5,6-dioxo-1,4,5,6-tetrahydro-1,2,4-triazin-3-yl radical substituted in the 1-position or 4-position, a 5,6-dioxo-1,2,5,6-tetrahydro-1,2,4-triazin-3-yl radical substituted in the 2-position, or a 1,3,4-triazol-5-yl, 2-alkoxycarbonyl-1,3,4-triazol-5-yl, 1,2,4-triazol-5-yl or 3-alkoxycarbonyl-1,2,4-triazol-5-yl radical substituted in the 1-position, [by an alkyl radical containing 2 to 4 carbon atoms, which is substituted by a sulphoamino, alkylsulphonylamino or sulphamoylamino group, an acylamino group (the acyl part of which is optionally substituted by hydroxyl, amino, alkylamino or dialkylamino) or an alkoxycarbonylamino, ureido, alkylureido or dialkylureido group], or represents a 1,3,4-thiadiazol-5-yl radical substituted by an acylamino or acylaminoalkyl radical, or represents a 1,3,4-oxadiazol-5-yl radical substituted by an acylaminoalkyl radical, or represents a tetrazol-5-yl radical substituted in the 1-position by an alkyl radical containing 2 to 4 carbon atoms, which is substituted by an acylamino, sulphamoylamino, sulphoamino, ureido, alkylureido or dialkylureido group, which are all functional derivatives of the corresponding amine, can be obtained by treating an amine of the general formula:

4-position, a 5,6-dioxo-1,2,5,6-tetrahydro-1,2,4-triazin-3-yl radical substituted in the 2-position, or a 1,3,4-triazol-5-yl, 2-alkoxycarbonyl-1,3,4-triazol-5-yl, 1,2,4-triazol-5-yl or 3-alkoxycarbonyl-1,2,4-triazol-5-yl radical substituted in the 1-position, by an aminoalkyl radical, the alkyl part of which contains 2 to 4 carbon atoms, or a 1,3,4-thiadiazol-5-yl radical substituted by an amino or aminoalkyl radical, or a 1,3,4-oxadiazol-5-yl radical substituted by an aminoalkyl radical, or a tetrazol-5-yl radical substituted in the 1-position by an aminoalkyl radical, the alkyl part of which contains 2 to 4 carbon atoms, by any method which is in itself known for forming an amide, sulphamide, carbamate or urea group without affecting the rest of the molecule, and then, if necessary, reducing the sulphoxide and removing the protective groups.

It is understood that the products which contain a sulpho, sulphonyl or sulphamoyl group are preferably prepared from a product of the general formula (Id) in which $n=0$.

Furthermore, if it is desired to prepare a product in which the radical R contains an amino or hydroxyl group, it is necessary to protect these radicals in the reactant used. Likewise, if R° represents the hydrogen atom, it is necessary to protect the oxime. If R° contains a carboxyl radical, this group can be free or protected.

If it is desired to prepare a product of the general formula (I) in which the radical R contains an alkylsulphonylamino, sulphamoylamino, acylamino (substituted or unsubstituted), alkoxycarbonylamino or dialkylureido substituent, the reaction is advantageously carried out with respectively the corresponding chlorosulphonyl derivative, acid chloride, chloroformate or dialkylcarbamoyl chloride, under the conditions described above for the reaction of the chloride of the acid of the general formula (VIII) with the 7-aminocephalosporin of the general formula (IX).

If it is desired to prepare a product of the general formula (I) in which the radical R contains a sulphoamino, alkylsulphonylamino or acylamino (substituted or unsubstituted) substituent, the reaction can be carried out by means of the corresponding acid anhydride, under the conditions described above for reacting the product of the general formula (VIII) in the form of the anhydride.

If it is desired to obtain a product of the general formula (I) in which R contains an acylamino radical (substituted or unsubstituted), it is also possible to carry out the reaction with the corresponding acid, under the operating conditions described above for the use of the acid of the general formula (VIII).

If it is desired to obtain a product of the general formula (I) in which R contains a ureido or alkylureido radical, an alkali metal isocyanate or an alkyl isocyanate, respectively, is reacted with the corresponding

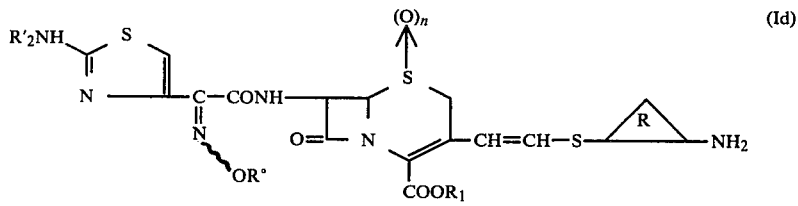

(Id)

in which R°, R₁, R'₂ and n are defined as above and -△R-NH₂ represents a 5,6-dioxo-1,4,5,6-tetrahydro-1,2,4-triazin-3-yl radical substituted in the 1-position or product of the general formula (Id), in an aqueous-organic or organic medium (e.g. in tetrahydrofuran), at a temperature between −20° and 60° C.

The reduction and the removal of the protective radicals are carried out under the conditions described above.

G. According to the present invention, the products of the general formula (I) in which R° and R' are defined as above and R represents a 5,6-dioxo-1,4,5,6-tetrahydro-1,2,4-triazin-3-yl radical substituted in the 1-position or 4-position, a 5,6-dioxo-1,2,5,6-tetrahydro-1,2,4-triazin-3-yl radical substituted in the 2-position, or a 1,3,4-triazol-5-yl, 2-alkoxycarbonyl-1,3,4-triazol-5-yl, 1,2,4-triazol-5-yl or 3-alkoxycarbonyl-1,2,4-triazol-5-yl radical substituted in the 1-position, by a thiazolidin-2-yl-alkyl radical, by a radical of the general formula (V) or by a hydroxyiminoalkyl or alkoxyiminoalkyl radical, the iminoalkyl part of which contains 2 to 5 carbon atoms, or represents a tetrazol-5-yl radical substituted in the 1-position by a hydroxyiminoalkyl or alkoxyiminoalkyl radical, the iminoalkyl part of which contains 2 to 5 carbon atoms, which are addition derivatives of the product of the general formula (I) in which R° and R" are defined as above and R is one of the heterocyclic rings mentioned above, substituted by a formylalkyl radical (or its hydrate form), can be obtained from an aldehyde of the general formula:

product of the general formula (Ie) in which $R_1$ and $R_2$ are hydrogen atoms is used, and $R_5$ contains a free carboxyl radical, the reaction is advantageously carried out in solvents such as pyridine, dimethyl sulphoxide or dimethylformamide.

If it is desired to prepare a product of the general formula (I) in which the radical R contains a substituent of the general formula (V), the reaction is carried out in an acid medium.

H. According to the present invention, the products of the general formula (I) in which R' represents a radical of the general formula (II), in which R" and R''' are defined as above, can also be obtained by esterifying a product of the general formula (I) in which R' represents a hydrogen atom and in which the amine group and, if necessary, the carboxyl radical present in R° have been protected beforehand, by any method which is in itself known for preparing an ester from an acid without affecting the rest of the molecule.

In general, an alkali metal salt or a tertiary amine salt of a product of the general formula (I), as defined above, in which the amine group and the acid group of R° have been protected beforehand and in which, if necessary, the radical R and the oxime are also protected, is reacted with a product of the general formula:

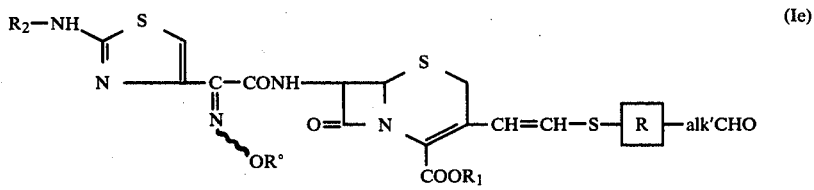

(Ie)

in which R°, $R_1$ and $R_2$ are defined as above (if R° contains a carboxyl radical, the latter is free or protected) and -[R]-alk'CHO represents a 5,6-dioxo-1-(or 4-)formylalkyl-1,4,5,6-tetrahydro-1,2,4-triazin-3-yl, 5,6-dioxo-2-formylalkyl-1,2,5,6-tetrahydro-1,2,4-triazin-3-yl, 1-formylalkyl-1,3,4-triazol-5-yl, 2-alkoxycarbonyl-1-formylalkyl-1,3,4-triazol-5-yl, 1-formylalkyl-1,2,4-triazol-5-yl, 3-alkoxycarbonyl-1-formylalkyl-1,2,4-triazol-5-yl or 1-formylalkyltetrazol-5-yl radical, by the addition respectively of cysteamine, an alcohol, hydroxylamine or an alkoxyamine, in accordance with the methods known for forming addition derivatives of carbonylated groups, this being followed, if necessary, by the removal of the protective radicals.

The reaction is generally carried out in an organic solvent, at a temperature between 20° C. and the reflux temperature of the reaction mixture.

The organic solvents are chosen according to the solubility of the products. If a product of the general formula (Ie) in which $R_1$ and $R_2$ are other than hydrogen is used, and if the carboxyl radical present in $R_5$ is protected, solvents such as tetrahydrofuran, acetonitrile, alcohols and ketones are advantageously used. If a

in which R" and R''' are defined as above and $Z_2$ represents a halogen atom, in an inert solvent such as dimethylformamide, at a temperature between 0° and 30° C.

I. According to the present invention, the products of the general formula (I) in which R° represents a radical of the general formula (VI) and R is other than a triazinyl or triazolyl radical substituted by a group of the general formula (V) can also be obtained by reacting a product of the general formula:

(in which $R^{iv}$ and $R^v$ are defined as above, $Z_3$ represents a halogen atom or a sulphate or sulphonate radical, and the acid group has been protected beforehand) with a product of the general formula:

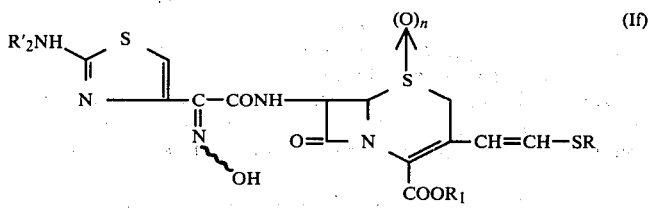

(If)

in which R, $R_1$, $R'_2$ and n are defined as above, and then, if necessary, reducing the sulphoxide obtained and removing the protective groups.

The acid group of the product of the general formula (VIa) can be protected by any protective group defined above for the protection of the carboxyl radicals.

It is understood that the amino or alkylamino groups which exist in some of the radicals R are protected and the formyl groups are free or protected.

The reaction is generally carried out in the presence of an inorganic or organic base (e.g. sodium hydroxide, potassium hydroxide, sodium hydride, potassium carbonate or a nitrogen-containing base such as triethylamine), in an organic solvent such as a chlorinated solvent (e.g. methylene chloride or dichloroethane), an ether (e.g. tetrahydrofuran or dioxane), a ketone (e.g. acetone) or an amide (e.g. dimethylformamide), if appropriate in the presence of water.

The reduction of the sulphoxide and the removal of the protective radicals are carried out under the conditions described above.

J. According to the present invention, the products of the general formula (I) in which R does not contain a substituent of the general formula (V) can also be prepared from a product (or from a mixture of the isomers of the product) of the general formula:

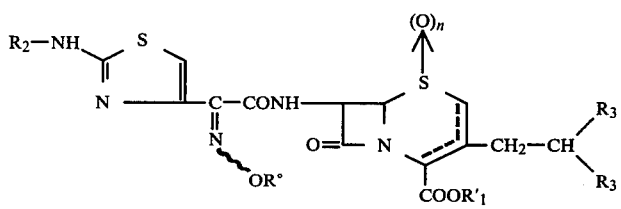

[in which, $R_2$ and n being defined as above, $R'_1$ is defined in the same way as $R_1$, except that it cannot represent hydrogen, and R° is a protected radical of the general formula (VI), an alkyl, vinyl or cyanomethyl radical or an oxime-protecting radical, if n=0, the product is in the form of a bicyclooct-2-ene or bicyclooct-3-ene, and if n=1, the product is in the form of a bicyclooct-2-ene, and $R_3$ represents a chlorine or bromine atom] by reaction with a thiol (or one of its alkali metal or alkaline earth metal salts) of the general formula (XI) in which R, which is defined as above, is optionally protected under the conditions defined in process B, this being followed, if appropriate, by the reduction of the sulphoxide obtained if n=1, and the removal of the protective groups.

The reaction is carried out under the conditions described above for the preparation of the products of the general formula (I) from a product of the general formula (XII) and a product of the general formula (XI). The conditions for protection (and freeing) of the various radicals are also the same as for process B.

The products of the general formula (XIX) can be prepared in accordance with the method described in German Patent Application No. 2,350,230.

The products of the general formula (VIII) in which R° represents a hydrogen atom or an alkyl radical can be prepared in accordance with the method described in Belgian Pat. No. 850,662.

The products of the general formula (VIII) in which R° represents a vinyl radical can be prepared in accordance with the method described in Belgian Pat. No. 869,079.

The products of the general formula (VIII) in which R° represents a cyanomethyl radical can be prepared in accordance with the method described in German Patent Application No. 2,812,625.

The products of the general formula (VIII) in which R° is a radical of the general formula (VI) can be prepared in accordance with the methods described in Belgian Pat. Nos. 864,810, 865,298, 876,541 and 876,542.

The products of the general formula (IX) can be obtained from a product of the general formula:

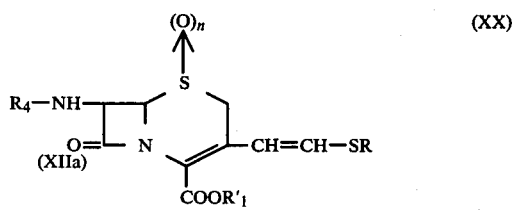

(XX)

(in which R and $R'_1$ are defined as above, except that they cannot represent a triazinyl or triazolyl radical substituted by a radical of the general formula (V), n is defined as above and $R_4$ represents a radical which can easily be removed) by removing the radical $R_4$ or, if appropriate, successively or simultaneously removing the radical $R_4$ and other protective radicals. It is not necessary to isolate the product of the general formula (IX) before it is used in the next stage of the synthesis.

The expression "radical $R_4$ which can easily be removed" is understood as meaning a benzhydryl or trityl radical, a 2,2,2-trichloroethyl radical, an acyl radical of the general formula:

$R_5$—CO—          (XXIa)

(in which R$_5$ is a hydrogen atom, an alkyl radical [optionally substituted by one or more halogen atoms or by a phenyl or phenoxy radical] or a phenyl radical) or a radical of the general formula:

$$R_6-O-CO- \qquad (XXIb)$$

[in which R$_6$ is an unsubstituted branched alkyl radical, a linear or branched alkyl radical {carrying one or more substituents chosen from amongst halogen atoms, a cyano, trialkylsilyl or phenyl radical or a phenyl radical substituted by one or more alkoxy, nitro or phenyl radicals} or a vinyl, allyl or quinolyl radical] or a nitrophenylthio radical. Furthermore, the radical R$_4$NH— can be replaced by a methyleneamino radical in which the methylene radical is substituted by dialkylamino group or an aryl group (the latter being optionally substituted by one or more methoxy or nitro radicals).

The following radicals may be mentioned as examples of radicals R$_4$ which can be used: formyl, acetyl, chloroacetyl, trichloroacetyl, phenylacetyl, phenoxyacetyl, benzoyl, t-butoxycarbonyl, 2-chloro-1,1-dimethylethoxycarbonyl, 2,2,2-trichloroethoxycarbonyl, 2,2,2-trichloro-1,1-dimethylethoxycarbonyl, 2-cyano-1,1-dimethylethoxycarbonyl, 2-trimethylsilylethoxycarbonyl, benzyloxycarbonyl, p-methoxybenzyloxycarbonyl, 3,5-dimethoxybenzyloxycarbonyl, p-nitrobenzyloxycarbonyl, diphenylmethoxycarbonyl, 2-(biphenyl-4-yl)-isopropoxycarbonyl, vinyloxycarbonyl, allyloxycarbonyl, 8-quinolyloxycarbonyl, o-nitrophenylthio and p-nitrophenylthio.

The following may be mentioned as examples of methyleneamino radicals: dimethylaminomethyleneamino, 3,4-dimethoxybenzylideneamino and 4-nitrobenzylideneamino.

The removal of the protective radical R$_4$ is carried out by any method known for freeing an amine group without affecting the rest of the molecule.

By way of example, the following methods may be mentioned:

If R$_4$ represents trityl, benzhydryl, trichloroacetyl, chloroacetyl, t-butoxycarbonyl, trichloroethoxycarbonyl, benzyloxycarbonyl, p-methoxybenzyloxycarbonyl or p-nitrobenzyloxycarbonyl: in accordance with the methods mentioned above for the freeing of the amino radical of the product of the general formula (I); in the case of the t-butoxycarbonyl radical, the reaction is advantageously carried out using p-toluene-sulphonic acid in acetonitrile, at a temperature between 0° and 50° C.;

if R$_4$ represents formyl, 2-chloro-1,1-dimethylethoxycarbonyl, 2-cyano-1,1-dimethylethoxycarbonyl, 3,5-dimethoxybenzyloxycarbonyl, diphenylmethoxycarbonyl, 2-(biphenyl-4-yl)-isopropoxycarbonyl, vinyloxycarbonyl, allyloxycarbonyl, 8-quinolyloxycarbonyl, o-nitrophenylthio or p-nitrophenylthio, and if R$_4$NH— is replaced by dimethylaminomethyleneamino, 3,4-dimethoxybenzylideneamino or 4-nitrobenzylideneamino: by hydrolysis in an acid medium;

if R$_4$ represents 2,2,2-trichloroethoxycarbonyl or 2,2,2-trichloro-1,1-dimethylethoxycarbonyl: by treatment with zinc in acetic acid;

if R$_4$ represents acetyl, benzoyl, phenylacetyl or phenoxyacetyl: in accordance with the method described in Belgian Pat. No. 758,800;

if R$_4$ represents trimethylsilylethoxycarbonyl: in accordance with the method described by H. GERLACH, Helv. Chim. Acta 60 (8), 3,039 (1977); or if R$_4$ represents p-nitrobenzyloxycarbonyl: by hydrogenolysis in the presence of palladium.

The products of the general formula (XX) can be obtained by reacting a thiol of the general formula (XI), as defined above, in which the radical R is optionally protected, or one of its alkali metal or alkaline earth metal salts, with a cephalosporin derivative (or, if necessary, with a mixture of isomers of a derivative) of the general formula:

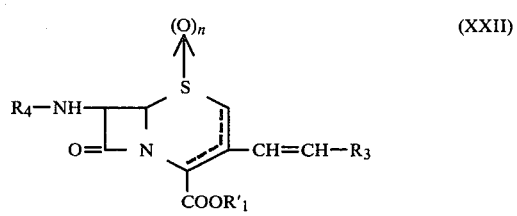

(XXII)

in which, R'$_1$, R$_3$, R$_4$ and n being defined as above, if n=0, the product is in the form of a bicyclooct-2-ene or bicyclooct-3-ene, and if n=1, the product is in the form of a bicyclooct-2-ene, and the substituent on the carbon atom in the 3-position of the bicyclooctene exhibits E/Z stereoisomerism.

The reaction is generally carried out under the conditions described above for the preparation of a 3-thiovinylcephalosporin of the general formula (I) from a thiol of the general formula (XI) and a product of the general formula (XII).

The thiols of the general formula (XI) (which can be used in their tautomeric form) can be prepared by applying one of the following methods, depending on the meaning of the radical R:

if R is a pyrid-3-yl radical: in accordance with the method described by H. M. WUEST and E. H. SAKAL, J. Amer. Chem. Soc., 73, 1,210 (1951), if R is a pyrid-3-yl-1-oxide radical: in accordance with the method described by B. BLANK et al., J. Med. Chem. 17, 1,065 (1974), if R is a pyrid-4-yl-1-oxide radical: in accordance with the method described by R. A. Y. JONES et al., J. Chem. Soc. 2,937 (1960), if R is a pyridazin-3-yl radical substituted by alkyl or methoxy and optionally N-oxidised: in accordance with the method described in Belgian Pat. No. 787,635, if R is a pyridazin-3-yl radical substituted by amino and optionally N-oxidised: in accordance with the method described in Belgian Pat. No. 579,291, if R is a pyridazin-3-yl radical substituted by acylamino and optionally N-oxidised: by applying the methods described by M. KUMAGAI and M. BANDO, Nippon Kagaku Zasshi, 84, 995 (1963), and by T. HORIE and T. UEDA, Chem. Pharm. Bull., 11, 114 (1963), if R is a tetrazolo[4,5-b]pyridazin-6-yl radical: in accordance with the method described in Belgian Pat. No. 804,251, if R is a 5,6-dioxo-1,4,5,6-tetrahydro-1,2,4-triazin-3-yl radical substituted in the 4-position, or a 2-alkoxycarbonyl-1,3,4-triazol-5-yl radical substituted in the 1-position, by a radical R$\gamma$ chosen from amongst:

(a) an allyl radical, an alkyl radical (containing 1 to 4 carbon atoms, which is itself optionally substituted by an alkoxy, alkylthio, phenyl, carbamoyl, alkylcarbamoyl, dialkylcarbamoyl, acyl, alkoxycarbonyl or thiazolidin-2-yl radical), (b) a 2,3-dihydroxypropyl or 1,3-dihydroxyprop-2-yl radical (optionally protected in the form of a cyclic acetal), (c) an alkyl radical [containing 2 to 4 carbon atoms, which is itself substituted by hydroxyl, carbamoyloxy, dialkylamino, alkylsulphinyl, alkylsulphonyl, alkylsulphonylamino, sulphamoylamino, acylamino (optionally substituted), alkoxycarbonylamino, ureido, alkylureido or dialkylureido], (d) a radical of the general formula (III) or (IV), or (e) a hydroxyiminoalkyl or alkoxyiminoalkyl radical, or if R is a 5,6-dioxo-1,4,5,6-tetrahydro-1,2,4-triazin-3-yl radical substituted in the 1-position, a 5,6-dioxo-1,2,5,6-tetrahydro-1,2,4-triazin-3-yl radical substituted in the 2-position, or a 3-alkoxycarbonyl-1,2,4-triazol-5-yl radical substituted in the 1-position, by a radical $R^\gamma$ as defined above (except that it cannot represent an unsubstituted alkyl radical) or by a hydroxyalkylcarbamoylalkyl radical, the hydroxyalkyl portion of which contains 2 to 4 carbon atoms, or if R is a 5,6-dioxo-4-hydroxyalkylcarbamoylalkyl-1,4,5,6-tetrahydro-1,2,4-triazin-3-yl radical, the hydroxyalkyl portion of which contains 2 to 4 carbon atoms: by reacting an alkyl oxalate or an alkyl monooxalate halide with a thiosemicarbazide of the general formula:

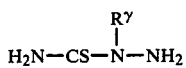

(in which formulae $R^\gamma$ is defined as above and $R^{\gamma 1}$ represents a hydroxyalkylcarbamoylalkyl radical or a radical $R^\gamma$).

The reaction is carried out in the presence of an alkali metal alcoholate, e.g. sodium ethylate or methylate or potassium t-butylate, by applying the method described by M. PESSON and M. ANTOINE, Bull. Soc. Chim. France 1,590 (1970).

It is not absolutely necessary to purify the product obtained (or to free the protected radicals) in order to use it for the preparation of the products of the general formula (I).

The thiosemicarbazides of the general formulae (XXIIIa) to (XXIIIc) can be prepared in accordance with one of the methods described by K. A. JENSEN et al., Acta Chem. Scand., 22, 1 (1968), or by applying the method described by Y. KAZAKOV and J. Y. POTOVSKII, Doklady Acad. Nauk. SSSR 134, 824 (1960), it being understood that, if $R^\gamma$ contains an amino radical, the latter is protected.

The protection of the amino radical and the removal of the protective radical are carried out in accordance with the usual methods which do not affect the rest of the molecule. The t-butoxycarbonyl group, which can be removed by acid hydrolysis, is used in particular.

If R is a 1,3,4-triazol-5-yl radical substituted in the 1-position by:

an alkyl, allyl or alkoxyalkyl radical, an alkyl radical (1 to 4 carbon atoms) which is itself substituted as defined above under (a), except that it cannot be substituted by a thiazolidin-2-yl radical, a radical as defined above under (c), or an alkoxyiminoalkyl radical: by applying one of the methods described by M. PESSON and M. ANTOINE, Bull. Soc. Chim. France 1,590 (1970).

If R is a 1,3,4-triazol-5-yl radical substituted in the 1-position by thiazolidin-2-yl-alkyl or hydroxyiminoalkyl: by reacting respectively cysteamine or hydroxylamine with a 1-dialkoxyalkyl-5-mercapto-1,3,4-triazole which can be obtained, by applying the method described by M. KANAOKA, J. Pharm. Soc. Japan, 75, 1,149 (1955), from a 4-dialkoxyalkylthiosemicarbazide.

If R is a 1,3,4-triazol-5-yl radical substituted in the 1-position by 2,3-dihydroxypropyl or 1,3-dihydroxyprop-2-yl (which are optionally protected in the form of a cyclic acetal), or represents a radical of the general formula (III) or (IV): by applying the method described by M. KANAOKA, J. Pharm. Soc. Japan, 75, 1,149 (1955).

If R is a 5,6-dioxo-1,4,5,6-tetrahydro-1,2,4-triazin-3-yl radical substituted in the 4-position, or a 2-alkoxycarbonyl-1,3,4-triazol-5-yl or 1,3,4-triazol-5-yl radical substituted in the 1-position, by acyloxyalkyl (optionally substituted): by respectively acylating 5,6-dioxo-4-hydroxyalkyl-3-mercapto-1,4,5,6-tetrahydro-1,2,4-triazine, 2-alkoxycarbonyl-1-hydroxyalkyl-5-mercapto-1,3,4-triazole or 1-hydroxyalkyl-5-mercapto-1,3,4-triazole, the mercapto radical of which has been protected beforehand [e.g. according to C. G. KRUSE et al., Tet. Lett. 1,725 (1976)], by any method known for acylating an alcohol without affecting the rest of the molecule, and then freeing the mercapto group in an acid medium.

If R is a 5,6-dioxo-1,4,5,6-tetrahydro-1,2,4-triazin-3-yl radical substituted in the 4-position, or a 2-alkoxycarbonyl-1,3,4-triazol-5-yl or 1,3,4-triazol-5-yl radical substituted in the 1-position, by aminoalkyl or alkylaminoalkyl: by freeing the amine group of the corresponding product, which amine group is protected e.g. by a t-butoxycarbonyl group.

If R is a 5,6-dioxo-1,4,5,6-tetrahydro-1,2,4-triazin-3-yl radical substituted in the 4-position, or a 2-alkoxycarbonyl-1,3,4-triazol-5-yl or 1,3,4-triazol-5-yl radical substituted in the 1-position, by sulphoaminoalkyl: from the corresponding product substituted by a t-butoxycarbonylaminoalkyl radical, by analogy with the method described in Belgian Pat. No. 847,237.

If R is a 1,4-dialkyl-5,6-dioxo-1,4,5,6-tetrahydro-1,2,4-triazin-3-yl or 1-alkyl-5,6-dioxo-1,4,5,6-tetrahydro-1,2,4-triazin-3-yl radical: in accordance with the method described in Belgian Pat. No. 830,455.

If R is a 2-alkyl-5,6-dioxo-1,2,5,6-tetrahydro-1,2,4-triazin-3-yl or 1-alkyl-3-alkoxycarbonyl-1,2,4-triazol-5-yl radical: in accordance with the method described by M. PESSON and M. ANTOINE, C.R. Acad. Sci., Ser C, 267, 25, 1,726 (1968).

If R is a 1,2,3-triazol-5-yl radical: in accordance with the method described in French Patent Application 2,215,942.

If R is a 1,3,4-triazol-5-yl radical: in accordance with the method described by M. KANAOKA, J. Pharm. Soc. Jap. 75, 1,149 (1955).

If R is a 1,3,4-thiadiazol-5-yl radical optionally substituted by alkyl, alkoxy, alkylthio, alkylsulphonyl, amino, alkylamino, dialkylamino or acylamino: in accordance with the methods described in Belgian Pat. No. 830,821.

If R is a 1,3,4-thiadiazol-5-yl radical substituted by hydroxyalkyl, aminoalkyl, alkylaminoalkyl or dialkylaminoalkyl: in accordance with the method described in German Patent Application No. 2,446,254.

If R is a 1,3,4-thiadiazol-5-yl radical substituted by a carboxyalkyl radical: by applying the method described in German Patent Application No. 1,953,861.

If R is a 1,3,4-thiadiazol-5-yl radical substituted by a trifluoromethyl radical: in accordance with the method described in German Patent Application No. 2,162,575.

If R is a 1,3,4-thiadiazol-5-yl radical substituted by a carboxyl radical: in accordance with the method described in Japanese Patent Application No. 77/48,666.

If R is a 1,3,4-thiadiazol-5-yl radical substituted by an acylaminoalkyl radical: in accordance with the method described in Japanese Patent Application No. 76/80,857.

If R is a 1,3,4-thiadiazol-5-yl radical substituted by a hydroxyalkylthio radical: by applying the method described by G. NANNINI, Arz. Forsch. 27 (2), 343 (1977).

If R is a 1,2,4-thiadiazol-5-yl radical substituted by alkyl or alkoxy: in accordance with the method described in German Patent Application No. 2,806,226 or according to Chem. Ber. 90, 184 (1957).

If R is a 1,3,4-oxadiazol-5-yl radical as defined in the formula (I) under α.8a): by applying the method described by E. HOGGARTH, J. Chem. Soc. 4,811 (1952).

If R is an oxazol-2-yl or 4-alkyloxazol-2-yl radical: by applying the method previously described by C. BRADSHER, J. Org. Chem. 32, 2,079 (1967).

If R is a tetrazol-5-yl radical optionally substituted in the 1-position by alkyl, hydroxyalkyl or phenyl: in accordance with the methods described in Belgian Pat. No. 830,821.

If R is a tetrazol-5-yl radical substituted in the 1-position by alkoxyalkyl: by adding sodium azide to an isothiocyanatoalkoxyalkyl compound, the reaction being carried out in an organic solvent such as ethanol, at the reflux temperature of the reaction mixture.

The isothiocyanatoalkoxyalkyl compound can be obtained by applying the method described by E. Schmidt et al., Chem. Ber. 73,286 (1940).

If R is a tetrazol-5-yl radical substituted in the 1-position by a carboxyalkyl radical: in accordance with the method described in Belgian Pat. No. 858,112.

If R is a tetrazol-5-yl radical substituted in the 1-position by a sulphoalkyl radical: in accordance with the method described in Belgian Pat. No. 856,498 or described by D. A. BERGES et al., J. Het. Chem. 15, 981 (1978).

If R is a tetrazol-5-yl radical substituted in the 1-position by an aminoalkyl, alkylaminoalkyl or dialkylaminoalkyl radical: by applying the method described in German Patent Application No. 2,738,711.

If R is a tetrazol-5-yl radical substituted in the 1-position by a sulphamoylalkyl, sulphamoylaminoalkyl or sulphoaminoalkyl radical: in accordance with the method described in Belgian Pat. No. 856,636.

If R is a tetrazol-5-yl radical substituted by an acylaminoalkyl radical, or a 1,3,4-thiadiazol-5-yl radical substituted by hydroxyl: in accordance with the method described in U.S. Pat. No. 4,117,123.

If R is a tetrazol-5-yl radical substituted in the 1-position by a ureidoalkyl, alkylureidoalkyl or dialkylureidoalkyl radical: from the corresponding product substituted by aminoalkyl (the mercapto radical of which has been protected beforehand), by treatment with an alkali metal isocyanate, with an alkyl isocyanate or with a dialkylcarbamoyl halide, and then freeing of the mercapto group under the conditions described in Belgian Pat. No. 847,237.

If R is a tetrazol-5-yl radical substituted in the 1-position by a carboxyalkylaminoalkyl radical: in accordance with the method described in German Patent Application No. 2,715,597.

If R is a tetrazol-5-yl radical substituted in the 1-position by a 2,3-dihydroxypropyl radical: in accordance with the method described in U.S. Pat. No. 4,064,242.

If R is a tetrazol-5-yl radical substituted in the 1-position by a 1,3-dihydroxyprop-2-yl radical: by adding sodium azide to a 2,2-dimethyl-1,3-dioxolan-5-yl isothiocyanate (and then freeing the hydroxyl groups, if appropriate).

If R is a tetrazol-5-yl radical substituted in the 1-position by a radical of the general formula (IIIa) or (IV) as defined as above, or a radical defined above under α.9c): by reacting sodium azide with the corresponding isothiocyanate, by analogy with the method described by R. E. ORTH, J. Pharm. Sci. 52 (9), 909 (1963), it being understood that, in the case where R contains a hydroxyl or hydroxyiminoalkyl substituent, the alcohol or the oxime are optionally protected, e.g. by a tetrahydropyranyl group.

If R is a 1,2,4-triazol-5-yl radical substituted in the 1-position by:

an allyl or alkoxyalkyl radical, an alkyl radical (1 to 4 carbon atoms) which is itself substituted as defined above under (a), except that it cannot be substituted by a thiazolidin-2-yl radical, a hydroxyalkylcarbamoylalkyl radical, the hydroxyalkyl part of which contains 2 to 4 carbon atoms, a radical as defined above under (c), or an alkoxyiminoalkyl radical: by analogy with the methods described by M. PESSON and M. ANTOINE, Bull. Soc. Chim. France, 1,599 (1970), or C.R. Acad. Sci., Ser C, 267, 25, 1,726 (1968).

If R is a 1,2,4-triazol-5-yl radical substituted in the 1-position by thiazolidin-2-yl-alkyl or by hydroxyiminoalkyl: by reacting respectively cysteamine or hydroxylamine with a 1-dialkoxyalkyl-5-mercapto-1,2,4-triazole which can be obtained by analogy with the method described by M. KANAOKA, J. Pharm. Soc. Japan, 75, 1,149 (1955), from a 4-dialkoxyalkylthiosemicarbazide.

If R is a 1,2,4-triazol-5-yl radical substituted in the 1-position by 2,3-dihydroxypropyl or 1,3-dihydroxyprop-2-yl (which are optionally protected in the form of a cyclic acetal) or by a radical of the general formula (III) or (IV): by analogy with the method described by M. KANAOKA, J. Pharm. Soc. Japan, 75, 1,149 (1955).

If R is a 5,6-dioxo-1,4,5,6-tetrahydro-1,2,4-triazin-3-yl radical substituted in the 1-position, a 5,6-dioxo-1,2,5,6-tetrahydro-1,2,4-triazin-3-yl radical substituted in the 2-position, or a 3-alkoxycarbonyl-1,2,4-triazol-5-yl or 1,2,4-triazol-5-yl radical substituted in the 1-position, by acyloxyalkyl (optionally substituted): by respectively acylating 5,6-dioxo-1-hydroxyalkyl-3-mercapto-1,4,5,6-tetrahydro-1,2,4-triazine, 5,6-dioxo-2-hydroxyalkyl-3-mercapto-1,2,5,6-tetrahydro-1,2,4-triazine, 3-alkoxycarbonyl-1-hydroxyalkyl-5-mercapto-1,2,4-triazole or 1-hydroxyalkyl-5-mercapto-1,2,4-triazole, the mercapto radical of which has been protected beforehand [e.g. according to C. G. KRUSE et al., Tet. Lett. 1,725 (1976)], by any method known for acylating an alcohol without affecting the rest of the molecule, and then freeing the mercapto group in an acid medium.

If R is a 5,6-dioxo-1,4,5,6-tetrahydro-1,2,4-triazin-3-yl radical substituted in the 1-position, a 5,6-dioxo-1,2,5,6-tetrahydro-1,2,4-triazin-3-yl radical substituted in the 2-position, or a 3-alkoxycarbonyl-1,2,4-triazol-5-yl or 1,2,4-triazol-5-yl radical substituted in the 1-position, by aminoalkyl or alkylaminoalkyl: by freeing the amine group of the corresponding product, which amine group is protected e.g. by a t-butoxycarbonyl group.

If R is a 5,6-dioxo-1,4,5,6-tetrahydro-1,2,4-triazin-3-yl radical substituted in the 1-position, a 5,6-dioxo-1,2,5,6-tetrahydro-1,2,4-triazin-3-yl radical substituted in the 2-position, or a 3-alkoxycarbonyl-1,2,4-triazol-5-yl or 1,2,4-triazol-5-yl radical substituted in the 1-position, by sulphoaminoalkyl: from the corresponding product substituted by a t-butoxycarbonylaminoalkyl radial, by analogy with the method described in Belgian Pat. No. 847,237.

If R is a 1-alkyl-5,6-dioxo-1,4,5,6-tetrahydro-1,2,4-triazin-3-yl radical substituted in the 4-position, a 1-alkyl-5,6-dioxo-1,2,5,6-tetrahydro-1,2,4-triazin-3-yl radical substituted in the 2-position, a 2-alkyl-5,6-dioxo-1,2,5,6-tetrahydro-1,2,4-triazin-3-yl radical substituted in the 1-position, or a 4-alkyl-5,6-dioxo-1,4,5,6-tetrahydro-1,2,4-triazin-3-yl radical substituted in the 1-position, by a formylalkyl radical or by a radical of the general formula (IIIa): by reacting an alkyl oxalate with a thiosemicarbazide, by analogy with the method described by M. PESSON and M. ANTOINE, C.R. Acad. Sci. 267, 15C, 904 (1968), or C.R. Acad. Sci. 267, 25, 1,726 (1968).

The products of the general formula (XII) or (XXII) can be prepared either by reacting an activated derivative of the acids $R'_3SO_3H$ and $R''_3COOH$ of the general formula:

[in these formulae, $R'_3$ and $R''_3$ are defined as above the Hal represents a halogen atom], or by reacting a halogenating agent, with a product (or a mixture of the isomers) of the general formula:

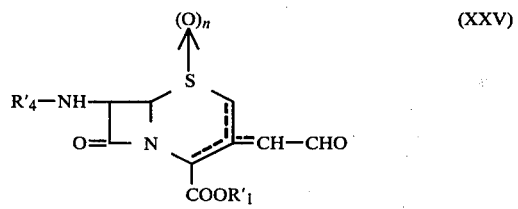

[in which, n and $R'_1$ being defined as above, if n=0, the product is in the form of a bicyclooct-2-ene or bicyclooct-3-ene or a 3-oxoethylidenebicyclooctane, and if n=1, the product is in the form of a bicyclooct-2-ene or 3-oxoethylidenebicyclooctane, and $R'_4$ represents a radical of the general formula:

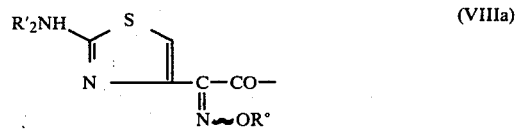

in which $R°$ is defined as in the general formula (I) and $R'_2$ is defined in the same way as $R_2$, except that it cannot represent hydrogen, or alternatively $R'_4$ represents a radical $R_4$ as defined above], and then, if appropriate, reducing the sulphoxide obtained and, if appropriate, removing the protective radicals of the amine group and of the acid groups (if it is desired to obtain a product of the general formula (XII) in which $R_1$ and/or $R_2$ are hydrogen).

It is understood that, if $R'_4$ is a radical of the general formula (VIIIa) in which $R°$ is a hydrogen atom, it is necessary to protect the oxime. The protection and the freeing are carried out in accordance with the methods described above.

Likewise, if $R°$ contains a carboxy radical, it is preferable to protect this group. In particular, if it is desired to obtain a product of the general formula (XII) or (XXII) in which $R_3$ is a halogen atom, a product of the general formula (XXV) in which the carboxyl group which can be present in $R'_4$ is protected, is used.

The reaction is generally carried out in the presence of a tertiary base as defined by the general formula (XIV), e.g. triethylamine or N,N-dimethylaniline, in a chlorinated organic solvent (e.g. methylene chloride), in an ester (ethyl acetate), in an ether (e.g. dioxane or tetrahydrofuran), in an amide (e.g. dimethylacetamide or dimethylformamide), in acetonitrile or N-methylpyrrolidone, or in a mixture of these solvents, or directly in a basic solvent such as pyridine, or alternatively, if $R_3$ is other than a halogen atom, the reaction can be carried out in an aqueous-organic medium, in the presence of an alkaline condensation agent (e.g. an alkali metal bicarbonate, sodium hydroxide or potassium hydroxide), at a temperature between −78° C. and the reflux temperature of the reaction mixture.

If appropriate, the reaction is carried out under nitrogen.

It is not absolutely necessary to have purified the intermediate of the general formula (XXV) in order to carry out this reaction.

If necessary, the removal of the protective radicals of the amine group and of the acid group is carried out in accordance with the methods described above for the preparation of the product of the general formula (I).

If it is desired to prepare a product of the general formula (XII) or (XXII) in which $R_3$ is a halogen atom, the halogenating agent can be chosen from amongst halogen derivatives of phosphorus, in particular:

halogen addition compounds of triarylphosphite, or phosphorus trichloride, phosphorus oxychloride, phosphorus pentachloride, dichlorotriphenylphosphorane or catechyltrichlorophosphorane if $R_3$ is a chlorine atom, or phosphorus tribromide, phosphorus oxybromide, phosphorus pentabromide or catechyltribromophosphorane if $R_3$ is a bromine atom.

If phosphorus trichloride (or tribromide) is used, this reagent is reacted with a product of the general formula (XXV) in which n=0.

Catechyltrichlorophosphorane (or catechyltribromophosphorane), which can be prepared in situ, can be obtained in accordance with the method described by H. GROSS and U. KARSCH, J. Prakt. Chem., 29, 315 (1965).

The halogen addition compounds of triarylphosphite, which can be formed in situ, are described by H. N. RYDON and B. L. TONGE, J. Chem. Soc., 3,043 (1956), by J. MICHALSKI et al., J. Org. Chem., 45, 3,122 (1980), or in Belgian Pat. No. 881,424, and can be prepared in accordance with the methods mentioned in these documents.

The preparation of the halogen derivatives of the general formula (XII) or (XXII) is carried out in an anhydrous medium.

If it is desired to prepare a product of the general formula (XII) or (XXII) in which $R_3$ is a chlorine or bromine atom, depending on the operating conditions, it is possible to isolate the dihalogen intermediate of the general formula:

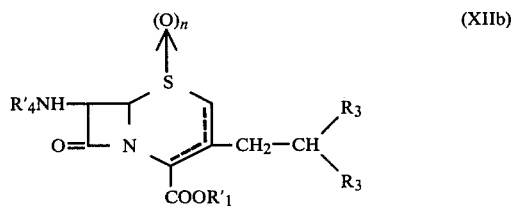
(XIIb)

[in which, n, $R'_4$, $R'_1$ and $R_3$ being defined as above, the product exhibits the same isomerism as the products of the general formula (XIIa)], which is then dehydrohalogenated.

If it is desired to isolate the dihalogen intermediate, the reaction is carried out with a halogenating agent, in an organic solvent such as a chlorinated solvent (e.g. methylene chloride, chloroform, carbon tetrachloride or 1,2-dichloroethane), an ether (e.g. ethyl ether, propylene oxide, tetrahydrofuran or dioxane), an amide (e.g. dimethylacetamide, dimethylpropionamide, dimethylformamide, N-acetylmorpholine, N-acetylpiperidine or N-methylpyrrolidone) or a mixture of these solvents, at a temperature which is slightly lower than for the preparation of the corresponding halogenovinyl derivative, i.e. between $-78°$ and $30°$ C.

It is also possible to carry out the reaction in the presence of a base such as pyridine, in one of the above solvents, at a temperature between $-78°$ and $0°$ C.

The dehydrohalogenation is carried out in the presence of a tertiary base as defined above, an aromatic amine (e.g. pyridine, picoline or quinoline) or an inorganic base (such as sodium hydroxide, potassium hydroxide, an alkali metal carbonate or bicarbonate or an alkaline earth metal carbonate), in an organic or aqueous-organic medium, in the abovementioned solvents, at a temperature between $-20°$ C. and the reflux temperature of the reaction medium.

It is not absolutely necessary to have purified the dihalogen intermediate in order to carry out the dehydrohalogenation thereof.

The products of the general formula (XXV) in which $R'_4$ is other than a radical of the general formula (VIIIa) and n is equal to 0 can be obtained by hydrolysing an enamine (or a mixture of isomeric enamines) of the general formula:

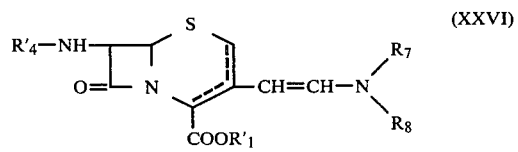
(XXVI)

in which, $R'_1$ and $R'_4$ being defined as above, the product is in the form of a bicyclooct-2-ene or bicyclooct-3-ene, and the substituent on the carbon atom in the 3-position of the bicyclooctene exhibits E/Z stereoisomerism, and $R_7$ and $R_8$, which are identical or different, represent alkyl radicals (optionally substituted by a hydroxyl, alkoxy, amino, alkylamino or dialkylamino radical) or phenyl radicals, or together form, with the nitrogen atom to which they are attached, a saturated heterocyclic ring of 5 or 6 ring members, optionally containing another hetero-atom chosen from amongst nitrogen, oxygen or sulphur, and optionally substituted by an alkyl radical.

Preferably, an enamine of the general formula (XXVI) in which $R_7$ and $R_8$ each represent a methyl radical is hydrolysed.

The reaction is generally carried out in an organic acid (e.g. formic acid or acetic acid) or a mineral acid (e.g. hydrochloric acid or sulphuric acid), in the presence or absence of a solvent, in an aqueous or organic medium, at a temperature between $-20°$ C. and the reflux temperature of the reaction mixture. If the reaction is carried out in an organic medium, the hydrolysis is performed by adding water to the reaction mixture, this being followed, if appropriate, by treatment with an inorganic base (e.g. an alkali metal bicarbonate) or an organic base (e.g. a tertiary amine or pyridine).

If the reaction is carried out in the presence of a solvent, it is not necessary for the solvent to be miscible with the acid aqueous phase. Contact is then effected by vigorous stirring.

Amongst the solvents which can be used, there may be mentioned chlorinated solvents, ethyl acetate, tetrahydrofuran, acetonitrile, dimethylformamide and alcohols. It is not absolutely necessary to have purified the intermediate of the general formula (XXVI) in order to carry out this reaction.

The products of the general formula (XXV) in which $R'_4$ is a radical of the general formula (VIIa) and n is equal to 0 can be obtained by hydrolysing an enamine (or a mixture of isomeric enamines) of the general formula:

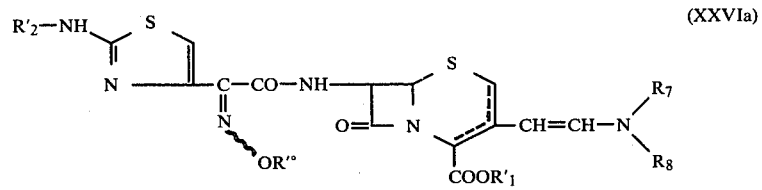
(XXVIa)

which is in the form of a bicyclooct-2-ene or bicyclooct-3-ene and in which the substituent on the carbon atom in the 3-position of the bicyclooctene exhibits E/Z stereoisomerism, $R'_1$ and $R'_2$ are defined as above, $R'^\circ$ represents a hydrogen atom, an alkyl, vinyl or cyanomethyl radical or a protected radical of the general formula (VI), and $R_7$ and $R_8$ are defined as in the general formula The reaction is carried out under the conditions indicated above for the hydrolysis of the enamine of the general formula (XXVI).

If it is desired to prepare a product of the general formula (XXV) containing a radical of the general formula (VI), it is necessary to use an enamine of the general formula (XXVIa) in which the protective radicals of the acid groups (of $R'^\circ$ and $-COOR'_1$) are different and can be removed selectively.

The removal of the protective radical of the acid group of the radical of the general formula (VI) is then carried out under the conditions described above.

The products of the general formula (XXV) in which n is equal to 1 can be obtained by oxidising the products of the general formula (XXV) in which n is equal to 0, by applying the method described in German Patent Application No. 2,637,176.

Likewise, the products of the general formulae (IX), (XII), (XIIa), (XIIb), (XVI), (XVIII) or (XXII) in which n is equal to 1 can be obtained respectively by oxidising the products of the general formulae (IX), (XII), (XIIa), (XIIb), (XVI) (XVIII) or (XXII) in which n is equal to 0, by applying the method described in German Patent Application No. 2,637,176.

The products of the general formula (XXVI) or (XXVIa) in which $R_7$ and $R_8$ are defined as above, except that they cannot represent alkyl substituted by hydroxyl, amino or alkylamino, can be obtained by reacting a product, optionally prepared in situ, of the general formula:

(XXVII)

[in which $R_7$ and $R_8$ are defined as above and $R_9$ and $R_{10}$, which are identical or different, either represent groups of the general formula:

$X_2R_{11}$  (XXVIIa)

in which $X_2$ is an oxygen atom and $R_{11}$ represents an alkyl or phenyl radical, or represent in one case a radical of the general formula (XXVIIa) in which $X_2$ represents an oxygen or sulfur atom and $R_{11}$ is alkyl or phenyl, and in the other case an amino radical of the general formula:

(XXVIIb)

in which $R_{12}$ and $R_{13}$ are defined in the same way as $R_7$ and $R_8$, or also $R_9$ and $R_{10}$ represent in each case a radical of the general formula (XXVIIb)] with a cephalosporin derivative of the general formula:

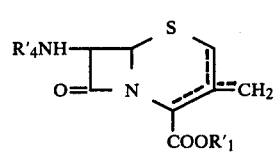
(XXVIII)

in which, $R'_1$ and $R'_4$ being defined as above, the product is in the form of a 3-methylbicyclooct-2-ene or 3-methylbicyclooct-3-ene or a 3-methylenebicyclooctane.

If a product of the general formula (XXVII) in which the radical (XXVIIb) is different from $-NR_7R_8$ is used, it is preferable to choose this product so that the amine $HNR_{12}R_{13}$ is more volatile than $HNR_7R_8$.

The reaction is generally carried out in an organic solvent such as dimethylformamide, hexamethylphosphorotriamide, dimethylacetamide, acetonitrile, ethyl acetate, dioxane, or a chlorinated solvent (e.g. 1,2-dichloroethane), or in a mixture of such solvents, at a temperature between 20° C. and the reflux temperature of the reaction mixture.

It is understood that, if $R^{10}$ is a hydrogen atom, it is preferable for the oxime to be protected under the conditions described above.

The products of the general formula (XXVI) in which $R'_1$ and $R'_4$ are defined as above and $R_7$ and $R_8$ represent alkyl radicals substituted by hydroxyl, amino or alkylamino can be obtained by trans-enamination from a product of the general formula (XXVI) in which $R_7$ and $R_8$ represent alkyl radicals, preferably methyl radicals.

The reaction is carried out by reacting an amine of the general formula:

(XXIX)

(in which $R'_7$ and $R'_8$, which are identical or different, represent alkyl radicals substituted by hydroxyl, amino or alkylamino) with the product of the general formula (XXVI), under the conditions described above for the reaction of a product of the general formula (XXVII) with a derivative of the general formula (XXVIII).

The products of the general formula (XXVII) can be prepared in accordance with the methods described by H. BREDERECK et al., Chem. Ber. 101,41 (1968), Chem. Ber. 101, 3,058 (1968) and Chem. Ber. 106, 3,725 (1973).

The cephalosporin derivatives of the general formula (XXVIII) in which $R'_4$ is a radical of general formula (VIIIa) can be prepared from the products of the general formula:

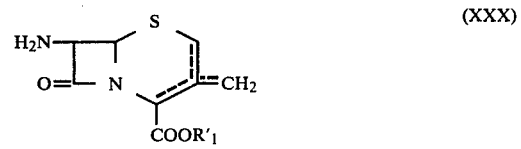
(XXX)

in which $R'_1$ is defined as above, by reaction with an acid of the general formula (VIII) or one of its reactive derivatives, under the conditions described above for the preparation of the products of the general formula (I).

The protective groups $R'_1$ and $R'_4$ of the product of the general formula (XXVIII) {or (XXX) in the case of $R'_1$} can be introduced into a 7-amino-cephalosporin of the general formula:

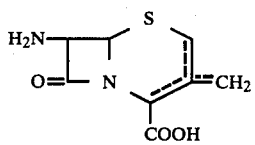 (XXXI)

in which the position of the double bond is defined as above, in accordance with methods which are known or are described in the literature:

If $R'_4$ is a formyl radical: according to J. C. SHEEHAN et al., J. Amer. Chem. Soc. 80 1156 (1958).

If $R'_4$ is acetyl, chloroacetyl, trichloroacetyl, phenylacetyl, phenoxyacetyl or benzoyl: according to E. H. FLYNN, Cephalosporins and Penicillins, Academic Press (1972).

If $R'_4$ is a tert.-butoxycarbonyl radical: according to L. MORODER et al., Hoppe Seyler's Z. Physiol. Chem. 357, 1651 (1976).

If $R'_4$ is 2,2,2-trichloro-1,1-dimethyl-ethoxycarbonyl: according to J. UGI et al., Angew. Chem. Int. Ed. Engl. 17(5), 361 (1978).

If $R'_4$ is 2,2,2-trichloro-ethoxycarbonyl, 2-chloro-1,1-dimethyl-ethoxycarbonyl, 2-cyano-1,1-dimethylethoxycarbonyl, 2-trimethylsilyl-ethoxycarbonyl, benzyloxycarbonyl, p-methoxybenzyloxycarbonyl, 3,5-dimethoxybenzyloxycarbonyl, p-nitrobenzyloxycarbonyl or vinyloxycarbonyl: by the action of a chloroformate in an aqueous organic medium in the presence of an alkali metal bicarbonate, or in accordance with Belgian Pat. No. 788,885.

If $R'_4$ is diphenylmethoxycarbonyl: by the action of the corresponding azidoformate in an aqueous organic medium, in the presence of an alkali metal bicarbonate.

If $R'_4$ is 2-(biphenyl-4-yl)-isopropoxycarbonyl: by analogy with the method described in Helv. Chim. Acta, 51, 924 (1968).

If $R'_4$ is quinol-8-yloxycarbonyl or allyloxycarbonyl: by the action of the corresponding carbonate in a basic aqueous organic medium.

If $R'_4$ is o-nitrophenylthio or p-nitrophenylthio: by analogy with the method described by L. ZERVAS et al., J. Amer. Chem. Soc. 85, 3660 (1963).

If $R'_4NH$— is replaced by dimethylaminomethyleneimino: by analogy with the method described by J. F. FITT, J. Org. Chem. 42(15), 2639 (1977).

If $R'_4NH$— is replaced by 4-nitro-benzylideneimino or 3,4-dimethoxy-benzylideneimino: according to the method described by R. A. FIRESTONE, Tetrahedron Lett., 375 (1972).

If $R'_1$ is methoxymethyl: according to S. SEKI et al., Tetrahedron Lett., 33, 2915 (1977).

If $R'_1$ is tert.-butyl: according to R. J. STEDMAN, J. Med. Chem., 9, 444 (1966).

If $R'_1$ is benzhydryl: according to Netherlands Patent Application 73/03,263.

If $R'_1$ is p-nitrobenzyl or p-methoxybenzyl: according to R. R. CHAUVETTE et al., J. Org. Chem. 38(17), 2994 (1973).

The cephalosporin derivatives of the general formulae (XXVIII) and (XXX) in which $R'_1$ represents a radical of the general formula (II) can be obtained by esterifying the corresponding acids in accordance with the method described above for the preparation of a product of the general formula (I) in which $R_1$ is a radical of the general formula (II) from a product of the general formula (I) in which $R_1$ is a hydrogen atom.

The products of the general formula (XII) can also be obtained by reacting an acid of the general formula (VIII) in which the amine group and, if necessary, the acid group of R° have been protected beforehand, or by reacting its reactive derivatives, with a product of the general formula (XVI) in which, $R_1$, $R_3$ and n being defined as above, if n=0, the product is in the form of a bicyclooct-2-ene or bicyclooct-3-ene, and if n=1, the product is in the form of a bicyclooct-2-ene, and the substituent on the carbon atom in the 3-position of the bicyclooctene exhibits E/Z stereoisomerism, or, if necessary, with a mixture of the isomers of this product, then, if appropriate, reducing the oxide obtained and then, if appropriate, removing the protective radicals.

The reaction is carried out under the conditions described above for the reaction of an acid of the general formula (VIII) with a 7-aminocephalosporin of the general formula (IX).

If necessary, the reduction of the oxide and also the removal of the protective radicals can be carried out under the conditions described for the preparation of the product of the general formula (I).

The product of the general formula (XVI) can be obtained by removing the protective radical $R_4$ of a product of the general formula (XIII) or, if appropriate, by simultaneously removing the radicals $R_4$ and $R'_1$ if it is desired to obtain a product of the general formula (XVI) in which $R_1$ is hydrogen.

The reaction is generally carried out under the conditions described above for the preparation of a product of the general formula (IX) from a product of the general formula (XX).

The products of the general formula (XII) in which R° is other than vinyl can also be prepared from a product of the general formula:

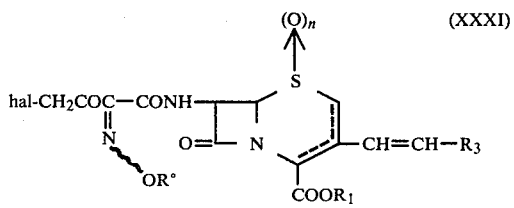 (XXXI)

[in which R°, $R_1$, $R_3$ and n are defined as above, except that R° cannot represent a vinyl radical, and hal is defined as in the general formula (XVIII)] by analogy with the method described for the preparation of the products of the general formula (I) in process D.

The products of the general formula (XXXI) can be prepared from a product of the general formula (XVI) by applying the methods described below for the preparation of products of the general formula (XVIII).

The thioloesters of the general formula (XV) can be prepared by reacting an acid or a reactive derivative of an acid of the general formula:

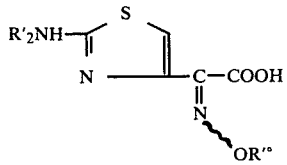

[in which R'° represents an alkyl, vinyl or cyanomethyl radical, a protected radical of the general formula (VI) or a protective radical, and in which R'$_2$ is defined in the same way as R$_2$, except that it cannot represent the hydrogen atom (or can represent the hydrogen atom if the reactive derivative is the acid chloride)] with a thiol of the general formula (XI) [in which R is defined as in the formula (XV)] or with one of its alkali metal or alkaline earth metal salts, and then removing the protective radical R'$_2$ of the amino radical, if it is desired to obtain a product in which R$_2$ is a hydrogen atom, and, if appropriate, removing the other protective radicals.

If it is desired to obtain a product of the general formula (XV) in which R° is a hydrogen atom, the protection of the oxime can be effected by any known method which does not affect the rest of the molecule. The trityl group is used in particular.

Furthermore, if it is desired to obtain a product of the general formula (XV) in which R contains a carboxyl or sulpho radical, it is preferable to react a reactive derivative of the acid of the general formula (VIIIb) with the corresponding thiol.

If it is desired to obtain a product in which R contains a hydroxyl radical, it is preferable to protect this radical beforehand, e.g. by a trityl group.

It is advantageous not to remove these protective groups until after the reaction of thioloesters of the general formula (XV) with the products of the general formula (XVI) or (IX).

a. If the product of the general formula (VIIIb) is used in the acid form, the condensation is generally carried out in an organic solvent such as dimethylformamide, acetonitrile, tetrahydrofuran, methylene chloride, chloroform or ethyl acetate, in the presence of a condensation agent such as carbodiimide (e.g. dicyclohexylcarbodiimide), N,N'-carbonyldiimidazole or 2-ethoxy-1-ethoxycarbonyl-1,2-dihydroquinoline, at a temperature between −20° and 40° C., and the protective groups are then removed, if appropriate.

b. If a reactive derivative of the acid of the general formula (VIIIb) is used, it is possible to use the anhydride, a mixed anhydride, an acid halide or a reactive ester of the general formula:

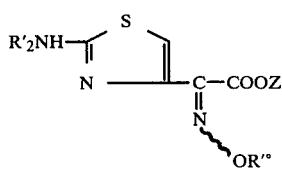

in which R'° and R'$_2$ are defined as above and Z represents a radical such as succinimido, benzotriazol-1-yl, 4-nitrophenyl, 2,4-dinitrophenyl, pentachlorophenyl or phthalimido.

c. If it is desired to obtain a product of the general formula (XV) in which R$_2$ is a hydrogen atom, it is also possible to use an acid halide, e.g. the acid chloride, by reacting the hydrochloride of the chloride of the acid of the general formula (VIII) with the thiol or with one of its salts.

If the anhydride, a mixed anhydride or an acid halide (which can all be prepared in situ) is used, the condensation is carried out in an inert organic solvent such as an ether (e.g. tetrahydrofuran or dioxane), a chlorinated solvent (e.g. chloroform or methylene chloride), an amide (e.g. dimethylformamide or dimethylacetamide) or a ketone (e.g. acetone), or in mixtures of the above solvents, in the presence of an acid acceptor such as an epoxide (e.g. propylene oxide) or such as a nitrogen-containing organic base like pyridine, N-methylmorpholine or a trialkylamine (e.g. triethylamine), or in an aqueous-organic medium, in the presence of an alkaline condensation agent such as sodium bicarbonate, and the reaction is carried out at a temperature between −40° and +40° C., and the protective group or groups are then removed, if appropriate.

If a reactive ester of the general formula (Xa) is used, the reaction is generally carried out in the presence of a trialkylamine (e.g. triethylamine), in an organic solvent such as dimethylformamide, at a temperature between 0° and 60° C., and the protective group or groups are then removed, if appropriate.

By way of example, the freeing of the various protected radicals can be carried out under the following conditions:

if it is desired to obtain a product of the general formula (XV) in which R$_2$ is hydrogen, the t-butoxycarbonyl protective radical of the aminothiazole is removed by treatment in an anhydrous acid medium. In this case, the product is obtained either in the form of a salt or in the form of a solvate with the acid employed. Preferably, trifluoroacetic acid is used, the reaction being carried out at between 0° and 20° C. It is also possible to remove the benzyl protective radical of the aminothiazole by catalytic hydrogenation.

if it is desired to obtain a product of the general formula (XV) in which the radical R comprises a hydroxyl group and/or in which R° is a hydrogen atom, the trityl group or groups are removed by acidolysis with anhydrous trifluoroacetic acid. The removal is carried out before, simultaneously with or after the removal of the protective radical of the aminothiazole.

According to the invention, the thioloesters of the general formula (XV) in which R contains a carbamoyloxyalkyl radical or an acyloxyalkyl radical (the acyl part of which is optionally substituted by a protected amino or alkylamino radical or a dialkylamino radical) can also be prepared from the corresponding thioloester of the general formula (XV) in which R contains a hydroxyalkyl radical and in which the radical R$_2$ and the radical R° are other than the hydrogen atom, by any method known for obtaining a carbamate or an ester from an alcohol without affecting the rest of the molecule.

The reaction is generally carried out in accordance with the methods described for the preparation of products of the general formula (I), containing such substituents, from a product of the general formula (Ic).

The products of the general formula (XVIII) in which R° is other than the hydrogen atom can be obtained by reacting an acid halide of the general formula:

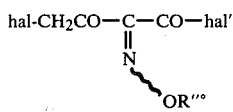 (XXXII)

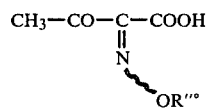 (XXXIV)

in which hal is defined as above, R′′′° is defined in the same way as R′° above for the general formula (VIIIb), except that it cannot represent a vinyl radical, and hal′ represents chlorine or bromine, with a 7-aminocephalosporin of the general formula (IX), and then, if appropriate, reducing the sulphoxide obtained (if n=1) and removing the protective radicals.

The reaction is generally carried out in an aqueous-organic medium, e.g. water/ether (tetrahydrofuran or dioxane), water/ketone (acetone) or water/chlorinated solvent (chloroform or methylene chloride), in the presence of an alkaline condensation agent such as an alkali metal bicarbonate (e.g. sodium bicarbonate), at a temperature between −40° and 40° C.

The reaction can also be carried out by analogy with the method described in French Patent Application No. 2,399,418.

It is understood that, if the radical R of the 7-aminocephalosporin contains an amino or alkylamino radical, the latter is protected, and if the radical R contains a hydroxyl, carboxyl, formyl or acylalkyl radical, the latter is free or protected.

The protection and the removal of the protective radicals are carried out under the conditions described above.

The products of the general formula (XXXII) can be obtained by halogenating a product of the general formula:

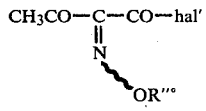 (XXXIII)

in which R′′′° and hal′ are defined as above, by any method which is in itself known for preparing halogen derivatives and which does affect the rest of the molecule.

If it is desired to obtain a product of the general formula (XXXII) in which hal represents a bromine atom, bromine is reacted in the presence of a catalyst, i.e. an acid catalyst such as hydrobromic acid, hydrochloric acid or sulphonic acids (methanesulphonic acid, anhydrous p-toluenesulphonic acid or benzenesulphonic acid), or in the presence of ultra-violet light.

If it is desired to obtain a product of the general formula (XXXII) in which hal is a chlorine atom, chlorine is reacted in the presence of a catalyst such as mentioned above or sulphuryl chloride.

The halogenation is carried out in an organic solvent such as chlorinated solvents (e.g. methylene chloride, chloroform, carbon tetrachloride, dichloroethane or trichloroethane) or ethers (e.g. ethyl ether or dioxane), or in a mixture of these solvents, at a temperature between −40° C. and the reflux temperature of the reaction mixture.

The products of the general formula (XXXIII) can be prepared by reacting a halogenating agent with the acid, a salt of the acid or a silyl ester of the acid of the general formula:

in which R′′′° is defined as above, in the presence of a product of the general formula:

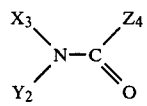 (XIVa)

in which $X_3$, $Y_2$ and $Z_4$ are identical or different and represent alkyl or phenyl radicals, or 2 of them together form, with the atoms to which they are attached, a heterocyclic ring of 5 or 6 ring members, optionally containing another hetero-atom chosen from amongst oxygen, nitrogen or sulphur, or alternatively $X_3$ and $Y_2$ represent alkyl radicals such as defined above and $Z_4$ represents a hydrogen atom or dialkylamino radical.

The halogenating agent can be chosen from amongst phosphorus pentachloride, phosphorus oxychloride, oxalyl chloride or phosgene if it is desired to obtain the acid chloride, or alternatively from amongst phosphorus pentabromide, phosphorus oxybromide or thionyl bromide if it is desired to obtain the acid bromide.

Amongst the products of the general formula (XIVa), dimethylacetamide, diethylacetamide, dimethylpropionamide, diethylpropionamide, dimethylformamide, N-acetylmorpholine, N-acetylpiperidine, N-acetyl-n-methylaniline, N-methylpyrrolidone or tetramethylurea is advantageously used.

If a salt of the acid of the general formula (XXXIV) is reacted, an alkali metal salt or a tertiary amine salt (e.g. the triethylamine salt) is preferably used.

If a silyl ester is reacted, a trimethylsilyl or t-butyldimethylsilyl ester is advantageously used. If appropriate, this ester can be prepared by applying the method described by A. WISSNER et al., J. Org. Chem., 43 (20), 3,972 (1978), or it can be formed in situ.

The halogenation of the acid of the general formula (XXXIV) is generally carried out in an organic solvent such as a chlorinated solvent (e.g. methylene chloride or chloroform), in an ester (e.g. ethyl acetate), in an aromatic hydrocarbon (e.g. toluene or xylene) or in an ether (e.g. ethyl ether, isopropyl ether or tetrahydrofuran), at a temperature between −70° and +30° C.

It is understood that the acids of the general formula (XXXIV) in the syn form lead to the acid halides in the syn form, and that the acids of the general formula (XXXIV) in the anti form lead to the acid halides of the general formula (XXXIII) in the anti form.

The acids of the general formula (XXXIV) in which R′′′° is other than a radical of the general formula (VI) can be obtained by the acid hydrolysis or the saponification of an ester of the general formula:

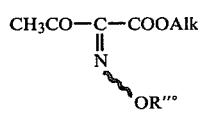 (XXXV)

in which R′′′° is defined as above and Alk represents an alkyl radical.

The reaction is generally carried out in the presence of sodium hydroxide, in ethanol, at the reflux temperature of the reaction mixture.

The esters of the general formula (XXXV) can be prepared by applying the method described by R. BUCOURT et al., Tetrahedron 34, 2,233 (1978).

The acids of the general formula (XXXIV) in which R'''° is a protected radical of the general formula (VI) can be prepared by reacting a product of the general formula (VIa), in which the acid group is protected, with a product of the general formula:

$$CH_3CO-\underset{\underset{OH}{\underset{\|}{N}}}{C}-COOR''_1 \quad (XXXVI)$$

in which R''$_1$ is an acid-protecting radical as defined above for R$_1$, and then removing the protective radical R''$_1$.

The reaction is generally carried out in the presence of an inorganic or organic base (e.g. sodium hydroxide, potassium hydroxide, sodium hydride, potassium carbonate or a nitrogen-containing base such as triethylamine), in an organic solvent such as a chlorinated solvent (e.g. methylene chloride or dichloroethane), an ether (e.g. tetrahydrofuran or dioxane), a ketone (e.g. acetone) or an amide (e.g. dimethylformamide).

It is necessary for the acid-protecting radicals R''$_1$ and the protective group of the radical of the general formula (VIa) to be different and to be removable selectively.

The removal of the protective radical R''$_1$ is carried out under the conditions described above.

The products of the general formula (XVIII) in which R° represents a hydrogen atom can be obtained from a product of the general formula:

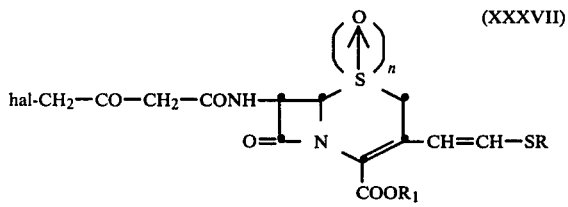

(XXXVII)

in which R, R$_1$, hal and n are defined as above, by analogy with the method described in French Patent Application No. 2,399,418, this being followed, if appropriate, by the reduction of the sulphoxide and the removal of the protective radicals.

It is understood that, if the radical R of the product of the general formula (XXXVII) contains an amino, alkylamino or formyl radical, the latter is protected, and if the radical R contains a hydroxyl, carboxyl or acylalkyl substituent, the latter is free or protected.

If necessary, the reduction of the sulphoxide and the removal of the protective radicals are carried out under the conditions described above.

The products of the general formula (XXXVII) can be obtained from a 7-aminocephalosporin of the general formula (IX) by reaction with a product of the general formula:

$$hal-CH_2-COCH_2-CO-hal \quad (XXXVIII)$$

in which hal is defined as above, (which product can be formed in situ), the reaction being carried out under the conditions described above for the condensation of a product of the general formula (XXXII) with a product of the general formula (IX), or by analogy with the method described in French Patent Application No. 2,399,418.

The products of the general formula (XXXVIII), which can be formed in situ, are prepared as described in the above French Application.

The isomers of the products of the general formulae (I), (IX), (XII), (XV), (XVI), (XVIII), (XX), (XXII), (XXV), (XXVI), (XXVIII) or (XXXI) can be separated by chromatography or crystallisation.

The new products according to the invention can be converted to addition salts with acids. According to the processes of the present invention, the products can be obtained in the form of the trifluoroacetate, the solvate with formic acid or water, phosphate, methanesulphonate, or the para-toluenesulphonate. The products of the general formula (I), in which R is defined according to the present invention, which are obtained in the form of these salts, can be freed and converted to salts of other acids in accordance with the usual methods.

The products according to the present invention can also be converted to metal salts or to addition salts with nitrogen-containing bases in accordance with the methods which are in themselves known. These salts can be obtained by reacting a metal base (e.g. an alkali metal base or alkaline earth metal base), ammonia or an amine with a product according to the invention, in a suitable solvent such as alcohol, an ether or water, or by means of an exchange reaction with a salt of an organic acid.

The salt formed precipitates, after concentration, if necessary, of its solution, and is separated off by filtration or decantation. It can also be obtained by lyophilising its solution.

As examples of pharmaceutically acceptable salts, there may be mentioned the addition salts with mineral acids (hydrochlorides, hydrobromides, sulphates, nitrates or phosphates) or organic acids (succinates, fumarates, maleates or p-toluenesulphonates), the salts with alkali metals (sodium, potassium or lithium) or with alkaline earth metals (magnesium or calcium), the ammonium salt or the salts of nitrogen-containing bases (ethanolamine, diethanolamine, trimethylamine, triethylamine, methylamine, propylamine, diisopropylamine, N,N-dimethylethanolamine, benzylamine, dicyclohexylamine, N-benzyl-β-phenethylamine, N,N'-dibenzylethylenediamine, diphenylenediamine, benzhydrylamine, quinine, choline, arginine, lysine, leucine or dibenzylamine).

The new products according to the present invention can be purified, if appropriate, by physical methods such as crystallisation or chromatography.

The new cephalosporin derivatives according to the present invention and their pharmaceutically acceptable salts possess particularly valuable anti-bacterial properties. They show a remarkable in vitro and in vivo activity against Gram-positive and Gram-negative germs.

In vitro, the products of the general formula (I) have shown themselves to be active at a concentration of between 0.5 and 10 μg/cc against staphylococcus strains sensitive to penicillin G (Staphylococcus aureus Smith) and at a concentration of between 0.01 and 2 μg/cc against Escherichia coli, NIHJ strain. Furthermore, the compounds of formula I defined under α have shown themselves to be active at a concentration of between 2 and 125 µg/cc against Pseudomonas aeruginosa.

In vivo, the products of the general formula (I) have shown themselves to be active at a daily dose of between 0.5 and 15 mg/kg, administered subcutaneously, against experimental infections caused in mice by Staphylococcus aureus Smith (sensitive to penicillin G), and at daily doses of between 0.01 and 10 mg/kg, administered subcutaneously, against experimental infections caused in mice by Escherichia coli (NIHJ strain).

Furthermore, the $LD_{50}$ of the products of the general formula (I) is between 1 g/kg and doses of more than 2.5 g/kg, administered subcutaneously to mice.

Of especial interest are the compounds of formula (I) in which R' represents a hydrogen atom and either R° represents a carboxyalkyl radical of the general formula (VI) and R represents pyrimidin-2-yl, 5,6-dioxo-1,4,5,6-tetrahydro-1,2,4-triazin-3-yl substituted in the 4-position by a formylalkyl or 2,3-dihydroxypropyl radical, 1-formylalkyl-4-alkyl-5,6-dioxo-1,4,5,6-tetrahydro-1,2,4-triazin-3-yl or a 1-alkyl-tetrazol-5-yl radical, or R° represents an alkyl radical or a carboxyalkyl radical of the general formula (VI) and R represents 5,6-dioxo-4-hydroxyalkylcarbamoylalkyl-1,4,5,6-tetrahydro-1,2,4-triazin-3-yl, 1-alkyl-4-formylalkyl-5,6-dioxo-1,4,5,6-tetrahydro-1,2,4-triazin-3-yl, or 1-formylalkyl-4-alkyl-5,6-dioxo-1,4,5,6-tetrahydro-1,2,4-triazin-3-yl.

Among these compounds those which are more specially active are the compounds of formula (I) in which R' represents hydrogen and either R° represents a radical of general formula (VI) in which $R^{iv}$ and $R^v$ are hydrogen atoms, or methyl radicals or together form a trimethylene radical, and R represents a 5,6-dioxo-1,4,5,6-tetrahydro-1,2,4-triazin-3-yl radical substituted in the 4-position by formylmethyl or 2,3-dihydroxypropyl or a 1-formylalkyl-4-alkyl-5,6-dioxo-1,4,5,6-tetrahydro-1,2,4-triazin-3-yl radical, or R° represents methyl or a radical of general formula (VI) as defined above, and R represents 5,6-dioxo-4-hydroxyalkylcarbamoylmethyl-1,4,5,6-tetrahydro-1,2,4-triazin-3-yl, 1-alkyl-4-formylalkyl-5,6-dioxo-1,4,5,6-tetrahydro-1,2,4-triazin-3-yl, or 1-formylalkyl-4-alkyl-5,6-dioxo-1,4,5,6-tetrahydro-1,2,4-triazin-3-yl, and more particularly the compounds of formula (I) in which R' represents hydrogen and either R° represents a radical of the general formula (VI) as defined above, and R represents 5,6-dioxo-4-formylmethyl-1,4,5,6-tetrahydro-1,2,4-triazin-3-yl, or R° represents methyl or a radical of the general formula (VI) as defined above, and R represents 5,6-dioxo-4-hydroxyethylcarbamoylmethyl-1,4,5,6-tetrahydro-1,2,4-triazin-3-yl, 1-methyl-4-formylmethyl-5,6-dioxo-1,4,5,6-tetrahydro-1,2,4-triazin-3-yl, or 1-formylmethyl-4-methyl-5,6-dioxo-1,4,5,6-tetrahydro-1,2,4-triazin-3-yl.

The following Examples, which are given without implying a limitation, show how the invention can be put into practice.

In these examples, the products are designated according to the nomenclature of Chemical Abstracts. It is understood that all the products according to the present invention exhibit the stereochemistry given by the partial general formula:

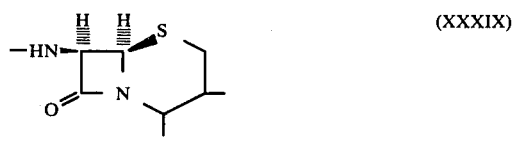

(XXXIX)

EXAMPLE 1

A mixture of the E form of the syn isomer of 2-benzhydryloxycarbonyl-7-[2-t-butoxycarbonylmethoxyimino-2-(2-tritylaminothiazol-4-yl)-acetamido]-8-oxo-3-(2-tosyloxyvinyl)-5-thia-1-azabicyclo[4.2.0]oct-2-ene-5-oxide (product 1a) (16.56 g), dimethylformamide (135 cc), 4-(2,2-dimethoxyethyl)-5,6-dioxo-3-thioxo-perhydro-1,2,4-triazine (3.67 g) and N,N-diisopropylethylamine (2.75 cc) is stirred at 50° C., under nitrogen, for 6 hours. It is diluted with ethyl acetate (600 cc), washed with water (2×150 cc) and a saturated solution of sodium chloride (2×150 cc), dried over sodium sulphate and filtered and the filtrate is concentrated to dryness at 20° C. under 20 mm Hg (2.7 kPa). The product is fixed to Merck silica gel (0.06–0.2) (50 g) and the powder is deposited on a column of silica gel (350 g) (diameter of the column: 4 cm, height: 75 cm). Elution is carried out with a 50/50 (by volume) cyclohexane/ethyl acetate mixture (3.2 liters) and a 25/75 (by volume) mixture (12 liters), 500 cc fractions being collected. Fractions 7 to 29 are concentrated to dryness at 20° C. under 20 mm Hg (2.7 kPa) and the E form of the syn isomer of 2-benzhydryloxycarbonyl-7-[2-t-butoxycarbonylmethoxyimino-2-(2-tritylaminothiazol-4-yl)-acetamido]-3-{2-[4-(2,2-dimethoxyethyl)-5,6-dioxo-1,4,5,6-tetrahydro-1,2,4-triazin-3-yl]-thiovinyl}-8-oxo-5-thia-1-azabicyclo[4.2.0]oct-2-ene-5-oxide (12.8 g) is collected in the form of a hard cream-coloured foam (product 1b).

Infra-red spectrum ($CHBr_3$), characteristic bands ($cm^{-1}$): 1,800, 1,720, 1,690, 1,590, 1,520, 1,495, 1,450, 1,370, 1,080, 1,065, 1,040, 945, 755, 700.

Proton NMR spectrum (350 MHz, $d_6$-DMSO, δ in ppm, J in Hz): 1.40 (s, 9H, —C(CH$_3$)$_3$); 3.24 (s, 6H, (—OCH$_3$)$_2$); 3.60 and 4.25 (2d, J=18, 2H, —SCH$_2$—); 3.95 (d, J=6, 2H, >NCH$_2$—); 4.52 (s, 2H, =NOCH$_2$—); 4.54 (t, J=6, 1H, —CH(OCH$_3$)$_2$); 5.08 (d, J=4, 1H, H in the 6-position); 5.91 (dd, J=4 and 9, 1H, H in the 7-position); 6.82 (s, 1H, H of the thiazole); 6.97 (s, 1H, —COOCH<); 6.96 and 7.0 (2d, J=16, 2H, —CH=CH—); 8.68 (d, J=9, 1H, —CONH—); 8.74 (s, 1H, —NHC(C$_6$H$_5$)$_3$; 12.35 (s, 1H, =NNHCO— or

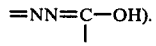

A solution of product (1b) (12.7 g) in methylene chloride (100 cc) and N,N-dimethylacetamide (4.34 cc) is treated with phosphorus trichloride (1.91 cc), at −5° C., for 1 hour 15 minutes, whilst stirring. The mixture is diluted with ethyl acetate (600 cc), washed with a 2% strength solution of sodium bicarbonate (2×200 cc) and a semi-saturated solution of sodium chloride (2×200 cc), dried over sodium sulphate and filtered and the filtrate is concentrated to dryness at 30° C. under 20 mm Hg (2.7 kPa). The product, dissolved in methylene chloride (50 cc), is fixed to Merck silica gel (0.06–0.2) (25 g)

and the powder obtained is deposited on a column of silica gel (175 g) (diameter of the column: 3 cm, height: 60 cm). Elution is carried out with a 60/40 (by volume) cyclohexane/ethyl acetate mixture (1.2 liters) and then with a 40/60 (by volume) mixture (2.8 liters), 100 cc fractions being collected. Fractions 13 to 28 are combined and evaporated to dryness at 20° C. under 20 mm Hg (2.7 kPa) and this yields the E form of the syn isomer of 2-benzhydryloxycarbonyl-7-[2-t-butoxycarbonyl methoxyimino-2-(2-tritylaminothiazol-4-yl)-acetamido]-3-{2-[4-(2,2-dimethoxyethyl)-5,6-dioxo-1,4,5,6-tetrahydro-1,2,4-traizin-3-yl]-thiovinyl}-8-oxo-5-thia-1-azabicyclo[4.2.0]oct-2-ene (9.45 g) in the form of a hard gellow-orange foam (product 1c).

Infra-red spectrum (CHBr$_3$), characteristic bands (cm$^{-1}$): 3,280, 1,800, 1,725, 1,690, 1,590, 1,530, 1,495, 1,440, 1,370, 1,160, 1,080, 945, 755, 700.

Proton NMR spectrum (350 MHz, d$_6$-DMSO, δ in ppm, J in Hz): 1.45 (s, 9H, —C(CH$_3$)$_3$); 3.25 (s, 6H, (—OCH$_3$)$_2$); 3.63 and 3.81 (2d, J=18, 2H, —SCH$_2$—); 3.95 (d, J=6, 2H, >NCH$_2$—); 4.52 (s, 2H, =NOCH$_2$—); 4.57 (t, J=6, 1H, —C$\underline{H}$(OCH$_3$)$_2$); 5.24 (d, J=4, 1H, H in the 6-position); 5.78 (dd, J=4 and 9, 1H, H in the 7-position); 6.78 (s, 1H, H of the thiazole); 6.95 (s, 1H, —COOCH<); 6.93 and 7.0 (2d, J=16, 2H, —CH=CH—); 8.80 (s, 1H, —N$\underline{H}$C(C$_6$H$_5$)$_3$); 9.50 (d, J=9, 1H, —CONH—); 12.62 (s, 1H, =NNHCO— or

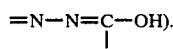

A solution of product (1c) (9.4 g) in trifluoroacetic acid (95 cc) is stirred at 20° C. for 25 minutes and concentrated to dryness at 20° C. under 0.05 mm Hg (0.007 kPa). The residue is triturated in diethyl ether (200 cc), the suspension is filtered and a yellow powder (6.7 g) is obtained. The product thus obtained is dissolved in pure formic acid (190 cc) and the solution is heated at 50° C. for 40 minutes and concentrated to dryness at 30° C. under 0.05 mm Hg (0.007 kPa). The residue is taken up in acetone (200 cc), the solution is concentrated to dryness at 20° C. under 30 mm Hg (4 kPa) and the operation is repeated a second time. The solid obtained is treated with acetone (300 cc) under reflux for 15 minutes, the mixture is filtered hot and, after drying, this yields the E form of the syn isomer of 7-[2-(2-aminothiazol-4-yl)-2-carboxymethoxyiminoacetamido]-2-carboxy-3-[2-(5,6-dioxo-4-formylmethyl-1,4,5,6-tetrahydro-1,2,4-triazin-3-yl)-thiovinyl]-8-oxo-5-thia-1-azabicyclo[4.2.0]oct-2-ene (product 1) (4.45 g) in the form of a yellow powder.

Infra-red spectrum (KBr), characteristic bands (cm$^{-1}$): 3,600, 2,200, 1,775, 1,815, 1,680, 1,635, 1,585, 1,195, 945, 800, 720.

Proton NMR spectrum (350 MHz, CF$_3$COOD, δ in ppm, J in Hz); 3.88 (s broad, 2H, —SCH$_2$—); 5.12 (s, 2H, =NOCH$_2$—); 5.21 (s, 2H, —CH$_2$CHO); 5.39 (d, J=4, 1H, H in the 6-position); 6.10 (d, J=4, 1H, H in the 7-position); 7.24 and 7.75 (2d, J=16, 2H, —CH=CH—); 7.52 (s, 1H, H of the thiazole); 9.77 (s, 1H, —CHO).

The product (1a) can be prepared in the following manner:

4-Dimethylaminopyridine (0.2 g) is added, whilst stirring, to a mixture, cooled to 5° C., of the E form of 7-amino-2-benzhydryloxycarbonyl-8-oxo-3-(2-tosyloxyvinyl)-5-thia-1-azabicyclo[4.2.0]oct-2-ene-5-oxide (product 1d) (23.14 g) in methylene chloride (400 cc), and of the syn isomer of 2-t-butoxycarbonylmethoxyimino-2-(2-tritylaminothiazol-4-yl)-acetic acid (prepared in accordance with the process described in Belgian Pat. No. 865,298) (26.10 g) in dimethylformamide (100 cc), and a solution of N,N'-dicyclohexylcarbodiimide (9.90 g) is added dropwise in the course of 17 minutes. The mixture is stirred for 1½ hours at 5° C. and 1½ hours at 20° C., acetic acid (2 cc) is added and the mixture is stirred for 15 minutes at 20° C. and concentrated to dryness at 20° C. under 20 mm Hg (2.7 kPa). The residue is taken up in ethyl acetate (200 cc), the solution is filtered, the organic phase is washed with water (2×250 cc), a 2% strength aqueous solution of sodium bicarbonate (2×250 cc) and a semi-saturated solution of sodium chloride (2×250 cc), dried over sodium sulphate and filtered, the filtrate is concentrated to dryness at 25° C. under 20 mm Hg (2.7 kPa), the residue is taken up in tetrahydrofuran (20 cc), the solution is left at 3° C. for 12 hours and filtered and the filtrate is concentrated to dryness at 20° C. under 20 mm Hg (2.7 kPa). The product is fixed to Merck silica gel (0.06–0.2) (200 g) and the powder is deposited on a column of silica gel (800 g) (diameter of the column: 6 cm, height: 77 cm). Elution is carried out with an 80/20 (by volume) cyclohexane/ethyl acetate mixture (3 liters), a 70/30 mixture (6 liters) and a 60/40 mixture (9 liters), 600 cc fractions being collected. Fractions 19 to 26 are concentrated to dryness at 20° C. under 20 mm Hg and a product (1a) (27.96 g) is collected in the form of a hard yellow foam.

Infra-red spectrum (CHBr$_3$), characteristic bands (cm$^{-1}$): 1,780, 1,725, 1,680, 1,495, 1,450, 1,370, 1,190, 1,180, 815, 740.

Proton NMR spectrum (350 MHz, CDCl$_3$, δ in ppm, J in Hz): 1.45 (s, 9H, —C(CH$_3$)$_3$); 2.45 (s, 3H, —CH$_3$ of the tosyl); 3.14 and 3.73 (2d, J=18, 2H, —S—CH$_2$—); 4.57 (d, J=5, 1H, —H in the 6-position); 4.72 (AB-type, J=16, 2H, =NOCH$_2$COO—); 6.02 (dd, J=5 and 9, 1H, —H in the 7-position); 6.75 (s, 1H, H of the thiazole); 6.90 and 7.05 (2d, J=12, 2H, —CH=CH—S—); 6.90 (s, 1H, —COO—C$\underline{H}$(C$_6$H$_5$)$_2$); 7.02 (s broad, 1H, —N-$\underline{H}$—C(C$_6$H$_5$)$_3$); 8.25 (d, J=9, 1H, —CO—NH—).

The product (1d) can be obtained in the following manner:

A solution of the E form of 2-benzhydryloxycarbonyl-7-t-butoxycarbonylamino-8-oxo-3-(2-tosyloxyvinyl)-5-thia-1-azabicyclo[4.2.0]oct-2-ene-5-oxide (product 1e) (54.3 g) and hydrated p-toluenesulphonic acid (30.4 g) in acetonitrile (1.4 liters) is stirred at 35° C. for 2 hours. It is concentrated to dryness at 30° C. under 20 mm Hg (2.7 kPa), the residue is taken up in ethyl acetate (1 liter) and the solution is washed with a semi-saturated solution of sodium bicarbonate (2×500 cc) and a semi-saturated solution of sodium chloride (2×500 cc), dried over sodium sulphate and concentrated to dryness at 20° C. under 20 mm Hg (2.7 kPa). The residue is triturated in ether (200 cc). This yields a product (1d) (28.13 g) in the form of a light brown powder.

Rf=0.32, silica gel chromatography plate [methylene chloride/methanol: 85/15 (by volume)].

The product (1e) can be prepared in the following manner:

A solution of 85% pure m-chloroperbenzoic acid (55.22 g) in methylene chloride (600 cc) is added dropwise, in the course of 2 hours, to a solution, cooled to −10° C., of 2-benzhydryloxycarbonyl-7-t-butoxycarbonylamino-8-oxo-3-(2-tosyloxyvinyl)-5-thia-1-azabicyclo[4.2.0]-oct-2-ene (or oct-3-ene) (product 1f, a mixture of the E and Z forms) (180.56 g), in methylene chloride (1.4 liters). The mixture is washed with a 5% strength solution of sodium bicarbonate (1.5 liters and water (2×1.5 liters), dried over sodium sulphate and concentrated at 20° C., under reduced pressure (20 mm Hg), to a volume of 300 cc. This solution is chromatographed on a column of Merck silica gel (0.05-0.2) (3 kg) (diameter of the column: 9.2 cm, height: 145 cm). Elution is carried out successively with the following cyclohexane/ethyl acetate mixtures: 80/20 (by volume) (15 liters) and 70/30 (by volume) (32 liters), 600 cc fractions being collected. Fractions 27 and 28 are collected and concentrated to dryness and this yields the Z form of the product (1e) (5.56 g).

Infra-red spectrum (CHBr$_3$), characteristic bands (cm$^{-1}$): 3,420, 1,800, 1,720, 1,505, 1,380, 1,370, 1,195, 1,180, 1,050, 1,010, 730.

Proton NMR spectrum (350 MHz, CDCl$_3$, δ in ppm, J in Hz): 1.49 (s, 9H, —C(CH$_3$)$_3$); 2.44 (s, 3H —CH$_3$); 3.36 and 4.04 (2d, J=19, 2H, —SCH$_2$—); 4.44 (d, J=4.5, 1H, H in the 6-position); 5.73 (d, J=9, 1H, —CONH—); 5.81 (dd, J=4.5 and 9, 1H, H in the 7-position); 6.42 (d, J=7, 1H, —C$\underline{H}$=CHOSO$_2$—); 6.46 (d, J=7, 1H, =CHOSO$_2$—); 6.89 (s, 1H, —COOCH<); 7.77 (d, J=9, 2H, H in the ortho-position of the tosyl).

In fractions 29 to 34, a mixture of the Z and E forms (26 g) is obtained.

Finally, in fractions 35 to 58, the E form of the product (1e) (43 g) is obtained:

Infra-red spectrum (CHBr$_3$), characteristic bands (cm$^{-1}$): 3,420, 1,800, 1,720, 1,505, 1,380, 1,370, 1,195, 1,180, 1,075, 935, 745.

Proton NMR spectrum (350 MHz, CDCl$_3$, δ in ppm, J in Hz): 1.48 (s, 9H, (CH$_3$)$_3$C—); 2.46 (s, 3H, —CH$_3$); 3.16 and 3.81 (2d, J=18, 2H, —SCH$_2$—); 4.46 (d, J=4.5, 1H, H in the 6-position); 5.73 (d, J=9, 1H, —CONH—); 5.8 (dd, J=9 and 4.5, 1H, H in the 7-position); 6.83 (d, J=13, 1H, —C$\underline{H}$=CHOSO$_2$—); 6.83 (s, 1H, —COOCH<); 7.08 (d, J=13, 1H, =CHOSO$_2$—); 7.73 (d, J=9, 2H, H in the ortho-position of the tosyl).

The product (1f), which is a mixture of the E and Z forms, can be obtained in the following manner:

A solution of formic acid (50 cc) in water (500 cc) is added to a solution of 2-benzhydryloxycarbonyl-7-t-butoxycarbonylamino-3-(2-dimethylaminovinyl)-8-oxo-5-thia-1-azabicyclo[4.2.0]oct-2-ene (E form) (product 1g) (113.7 g) in tetrahydrofuran (1 liter). The homogeneous solution is stirred at 20° C. for 20 minutes and then concentrated to a quarter of its volume under reduced pressure (20 mm Hg) at 20° C. The concentrate is taken up in ethyl acetate (2 liters), washed with a 5% strength solution of sodium bicarbonate (2×500 cc), water (2×500 cc) and a saturated solution of sodium chloride (2×500 cc), dried over sodium sulphate and filtered and the filtrate is evaporated to dryness at 20° C. under reduced pressure (20 mm Hg). A crude product (112.4 g) is collected and this is treated, in solution in anhydrous pyridine (250 cc), at 5° C., with tosyl chloride (57.2 g). After 30 minutes at 5° C. and 1 hour at 20° C., the solution is poured into a water/crushed ice mixture (1 liter). The aqueous phase is separated off and the insoluble material is washed with distilled water (300 cc). The pasty product is dissolved in ethyl acetate (200 cc) and the solution is washed with 1 N hydrochloric acid (2×750 cc), a 5% strength solution of sodium bicarbonate (2×750 cc) and water (4×750 cc), dried over sodium sulphate and concentrated to dryness under reduced pressure (20 mm Hg) at 20° C. This yields a product (121 g), mainly consisting of a product (1f) (a mixture of the E and Z forms), in the form of a crude, hard brown foam.

The product (1g) is prepared as described below in Example 11 for the product (11i).

EXAMPLE 2

The procedure of Examle 1 is followed, but the E form of the syn isomer of 2-benzhydryloxycarbonyl-7-[2-t-butoxycarbonylmethoxyimino-2-(2-tritylaminothiazol-4-yl)-acetamido]-8-oxo-3-(2-tosyloxyvinyl)-5-thia-1-azabicyclo[4.2.0]oct-2-ene-5-oxide (product 2a) (11.04 g), dimethylformamide (50 cc), 4-(2,2-dimethyldioxolan-3-yl) methyl-5,6-dioxo-3-thioxo-perhydro-1,2,4-triazine (2.72 g) and N,N-diisopropylethylamine (1.84 cc) are used as the starting materials. The reaction product is chromatographed on a column of Merck silica gel (0.04-0.06) (diameter of the column: 6 cm, height: 30 cm), elution being carried out with a 20/80 (by volume) cyclohexane/ethyl acetate mixture (4 liters), ethyl acetate (2 liters) and a 90/10 (by volume) ethyl acetate/methanol mixture (2 liters), under a pressure of 40 kPa, and 125 cc fractions being collected. Fractions 14 to 48 are evaporated to dryness at 20° C. under 20 mm Hg (2.7 kPa) and this yields the E form of the syn isomer of 2-benzhydryloxycarbonyl-7-[2-t-butoxycarbonylmethoxyimino-2-(2-tritylaminothiazol-4-yl)-acetamido]-3-{2-[4-(2,2-dimethyldioxolan-3-yl)-methyl-5,6-dioxo-1,4,5,6-tetrahydro-1,2,4-triazin-3-yl]-thiovinyl}-8-oxo-5-thia-1-azabicyclo[4.2.0]-oct-2-ene-5-oxide (product 2b) (2.41 g) in the form of a hard, light brown foam.

Infra-red spectrum (CHBr$_3$), characteristic bands (cm$^{-1}$): 3,380, 3,240, 1,800, 1,720, 1,680, 1,590, 1,525, 1,495, 1,450, 1,370, 1,070, 1,045, 940, 750, 700.

Proton NMR spectrum (350 MHz, CDCl$_3$, δ in ppm, J in Hz): 1.40 (s, 9H, —C(CH$_3$)$_3$); 1.30 and 1.45 (2s, 6H, (—CH$_3$)$_2$); 3.32 and 4.10 (2d, J=18, 2H, —S—CH$_2$—); 3.70 to 4.00 (m, 2H, —CH$_2$—O—); 4 to 4.2 (m, 2H, >N—CH$_2$—); 4.40 (m, 1H,

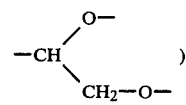

);

4.68 (b, 3H, =N—O—CH$_2$—+—H in the 6-position); 5.87 (m, 1H, —H in the 7-position); 6.71 (s, 1H, —H of the thiazole); 6.82 (d, J=16, 1H, —C$\underline{H}$=CH—S—); 6.95 (s, 1H, —COO—C$\underline{H}$(C$_6$H$_5$)$_2$); 7.64 (b, 1H, —N$\underline{H}$—C(C$_6$H$_5$)$_3$); 8.28 (d, J=9, —CO—NH—); 11.90 (s broad, 1H, =N—NH—CO— or

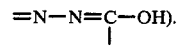

).

A solution of product (2b) (2.38 g) in methylene chloride (15 cc) and N,N-dimethylacetamide (0.8 cc) is treated with phosphorus trichloride (0.35 cc) in a similar manner to Example 1. The residue obtained after the treatment is chromatographed on a column of Merck silica gel (0.04-0.06) (diameter of the column: 4 cm, height: 20 cm). Elution is carried out with a 35/65 (by volume) cyclohexane/ethyl acetate mixture (2 liters)

under a pressure of 40 kPa, 125 cc fractions being collected. Fractions 4 to 10 are concentrated to dryness at 25° C. under 20 mm Hg (2.7 kPa) and the E form of the syn isomer of 2-benzhydryloxycarbonyl-7-[2-t-butoxycarbonylmethoxyimino-2-(2-tritylaminothiazol-4-yl)-acetamido]-3-{2-[4-(2,2-dimethyldioxolan-3-yl)-methyl-5,6-dioxo-1,4,5,6-tetrahydro-1,2,4-triazin-3-yl]-thiovinyl}-8-oxo-5-thia-1-azabicyclo[4.2.0]oct-2-ene (product 2c) (1.17 g) is collected in the form of a hard yellow foam.

Infra-red spectrum (CHBr$_3$), characteristic bands (cm$^{-1}$): 3,390+3,260, 1,790, 1,725, 1,680, 1,585, 1,530, 1,495, 1,450, 1,370, 1,070, 1,045, 940, 760, 740, 700.

Proton NMR spectrum (350 MHz, CDCl$_3$, δ in ppm, J in Hz): 1.42 (s, 9H, —C(CH$_3$)$_3$); 1.32 and 1.45 (2s, 6H, (—CH$_3$)$_2$); 3.58 and 3.62 (2d, J=18, 2H, —S—CH$_2$—); 3.77 and 3.95 (2 m, 2H, —CH$_2$—O—); 4.13 (m, 2H, >N—CH$_2$—); 4.43 (m, 1H,

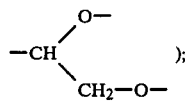);

4.70 and 4.78 (2d, J=16, 2H, =N—OCH$_2$—); 5.10 (d, J=14, 1H, —H in the 6-position); 5,86 (dd, J=4 and 9, 1H, —H in the 7-position); 6.78* (2d, J=16, 1H, —C$\underline{H}$=CH—S—); 6.82 (s, 1H, H of the thiazole); 6.96 (s, 1H, —COO—CH(C$_6$H$_5$)$_2$); 8.78 (d, J=9, 1H, —CO—NH—); 11.02 (s broad, 1H, =N—NH—CO— or

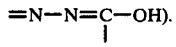

(* probable presence of two conformational isomers).

A solution of product (2c) (1.15 g) in trifluoroacetic acid (11.5 cc) is left at 20° C. for 20 minutes and concentrated to dryness at 20° C. under 0.05 mm Hg (0.007 kPa), the residue is triturated in diethyl ether (30 cc) and the mixture is filtered. The yellow solid obtained is dissolved in a mixture of formic acid (25 cc) and water (5 cc) and the solution is stirred at 50° C. for 45 minutes and concentrated to dryness at 20° C. under 0.05 mm Hg (0.007 kPa). The residue is taken up in acetone (3×100 cc), each solution being concentrated to dryness at 25° C. under 30 mm Hg (4 kPa), the solid obtained is then heated under reflux in acetone (40 cc) and the mixture is filtered hot. The E form of the syn isomer of 7-[2-(2-aminothiazol-4-yl)-2-carboxymethoxyiminoacetamido]-2-carboxy-3-{2-[4-(2,3-dihydroxypropyl)-5,6-dioxo-1,4,5,6-tetrahydro-1,2,4-triazin-3-yl]-thiovinyl}-8-oxo-5-thia-1-azabicyclo[4.2.0]oct-2-ene (product 2) (0.61 g) is collected in the form of a yellow powder. The NMR spectrum shows the presence, in this product, of the formic acid ester of one or other of the alcohol groups.

Infra-red spectrum (KBr), characteristic bands (cm$^{-1}$): 3,600–2,200, 1,775, 1,715, 1,685, 1,635, 1,590, 1,380, 1,200, 945.

Proton NMR spectrum (350 MHz, d$_6$-DMSO, δ in ppm, J in Hz): characteristic peaks: 4.62 (s, =N—O—CH$_2$—); 5.25 (d, J=4, —H in the 6-position); 5.85 (dd, J=4 and 9, H in the 7-position); 6.83 (s, H of the thiazole); 9.55 (d, J=9, —CO—NH—); 12.62 (s, =N—NH—CO— or

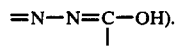

4-(2,2-Dimethyldioxolan-4-yl-methyl)-5,6-dioxo-3-thioxo-perhydro-1,2,4-triazine can be prepared in the following manner:

A solution of sodium (1.12 g) in anhydrous methanol (50 cc) is prepared, 4-(2,2-dimethyldioxolan-4-yl-methyl) thiosemicarbazide (10 g) is added at 25° C., under nitrogen and whilst stirring, diethyl oxalate (6.6 cc) is then added dropwise in the course of 10 minutes and the mixture is heated under reflux for 2 hours. It is left to cool to 20° C., diluted with diethyl ether (1 liter) and filtered and a white solid (3.7 g) is collected after drying. The product is taken up in methylene chloride (200 cc) and the solution is stirred in the presence of 1 N hydrochloric acid (10 cc). The organic phase is decanted, washed with a saturated aqueous solution of sodium chloride (2×50 cc), dried over sodium sulphate and concentrated to dryness at 20° C. under 20 mm Hg (2.7 kPa). The residual oil is taken up in methylene chloride (50 cc), crystallisation is initiated by scratching and the mixture is left at 4° C. for 3 hours. After filtration and drying, 4-(2,2-dimethyldioxolan-4-yl-methyl)-5,6-dioxo-3-thioxo-perhydro-1,2,4-triazine (1.5 g) is collected in the form of white crystals.

Infra-red spectrum (KBr), characteristic bands (cm$^{-1}$): 3,600–3,100, 1,680, 1,575, 1,535, 1,210, 1,060.

Proton NMR spectrum (80 MHz, d$_6$-DMSO, δ in ppm, J in Hz): 1.30 and 1.42 (2s, 6H, >C(CH$_3$)$_2$); 3.95 (m, 2H, —CH$_2$O—);

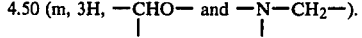

4-(2,2-Dimethyldioxolan-4-yl-methyl)-thiosemicarbazide can be prepared in the following manner:

A mixture of methyl N-(2,2-dimethyldioxolan-4-yl-methyl)-dithiocarbamate prepared according to U.S. Pat. No. 4,064,242 (23.6 g), absolute ethanol (500 cc) and hydrazine hydrate (5.6 g) is heated under reflux for 2 hours 30 minutes. It is concentrated to dryness at 20° C. under 20 mm Hg (2.7 kPa) and the residue is taken up in diethyl ether (100 cc). After filtration and drying, 4-(2,2-dimethyldioxolan-4-yl-methyl)-thiosemicarbazide (15.2 g) is collected in the form of a cream-coloured solid melting at 145° C.

Infra-red spectrum (KBr), characteristic bands (cm$^{-1}$): 3,340, 3,200, 1,630, 1,555, 1,510, 1,380, 1,370, 1,240, 1,210, 1,060.

Proton NMR spectrum (80 MHz, CDCl$_3$, δ in ppm, J in Hz): 1.38 and 1.48 (2s, 6H, >C(CH$_3$)$_2$); 3.72 (dd, J=5 and 6, 2H, —CH$_2$N<); 3.90 (s, 2H, —NH$_2$); 4.10 (dd, J=6 and 7, 2H, —CH$_2$O—); 4.38 (m, 1H, >CHO—); 7.78 (t, J=5, 1H, —CH$_2$N$\underline{H}$—);

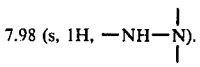

EXAMPLE 3

The procedure of Example 1 is followed, but the E form of the syn isomer of 2-benzhydryloxycarbonyl-7-

[2-t-butoxycarbonylmethoxyimino-2-(2-tritylamino-thiazol-4-yl)-acetamido]-8-oxo-3-(2-tosyloxyvinyl)-5-thia-1-azabicyclo[4.2.0]oct-2-ene-5-oxide (product 3a) (7.18 g), dimethylformamide (65 cc), 1-methyl-5-mercaptotetrazole (0.91 g) and N,N-diisopropylethylamine (1.36 cc) are used as the starting materials. After this treatment, the product obtained is chromatographed on a column of Merck silica gel (0.06–0.2) (150 g) (diameter of the column: 3 cm, height: 48 cm). Elution is carried out with an 80/20 (by volume) cyclohexane/ethyl acetate mixture (500 cc), a 60/40 mixture (1 liter) and a 40/60 mixture (2 liters), 125 cc fractions being collected. Fractions 17 to 26 are concentrated to dryness at 25° C. under 25 mm Hg (3.3 kPa) and this yields the E form of the syn isomer of 2-benzhydryloxycarbonyl-7-[2-t-butoxycarbonylmethoxyimino-2-(2-tritylaminothiazol-4-yl)-acetamido]-3-[2-(1-methyltetrazol-5-yl)-thiovinyl]-8-oxo-5-thia-1-azabicyclo[4.2.0]oct-2-ene-5-oxide (product 3b) (5.01 g) in the form of a hard cream-coloured foam.

Infra-red spectrum (CHBr$_3$), characteristic bands (cm$^{-1}$): 1,800, 1,730, 1,685, 1,520, 1,495, 1,450, 1,215, 1,155, 1,095, 1,045, 945, 750, 700.

Proton NMR spectrum (350 MHz, d$_6$-DMSO, δ in ppm, J in Hz): 1.42 (s, 9H, —C(CH$_3$)$_3$); 3.64 and 4.30 (2d, J=18, 2H, —SCH$_2$—); 3.98 (s, 3H, >NCH$_3$); 4.53 (s, 2H, =NOCH$_2$—); 5.07 (d, J=4, 1H, H in the 6-position); 5.93 (dd, J=4 and 9, 1H, H in the 7-position); 6.83 (s, 1H, H of the thiazole); 7.07 (d, J=16, 1H, —CH=CHS—); 8.65 (d, J=9, 1H, —CONH—); 8.71 (s, 1H, —NHC(C$_6$H$_5$)$_3$).

The procedure of Example 1 is followed, using a solution of product (3b) (4.72 g) in methylene chloride (45 cc) and dimetylacetamide (1.8 cc), and phosphorus trichloride (0.79 cc), as the starting materials. After this treatment, the product is chromatographed on a column of Merck silica gel (0.06–0.2) (100 g) (diameter of the column: 3 cm, height: 33.6 cm), elution being carried out with an 80/20 (by volume) cyclohexane/ethyl acetate mixture (250 cc), a 70/30 mixture (500 cc) and a 60/40 mixture (1.5 liters). By evaporating fractions 3 to 8, the E form of the syn isomer of 2-benzhydryloxycarbonyl-7-[2-t-butoxycarbonylmethoxyimino-2-(2-tritylaminothiazol-4-yl)-acetamido]-3-[2-(1-methyltetrazol-5-yl)-thiovinyl]-8-oxo-5-thia-1-azabicyclo[4.2.0]oct-2-ene (product 3c) (3.45 g) is obtained in the form of a hard yellow foam.

Infra-red spectrum (CHBr$_3$), characteristic bands (cm$^{-1}$): 1,790, 1,730, 1,690, 1,525, 1,495, 1,450, 1,370, 1,290, 1,160, 945, 750, 700.

Proton NMR spectrum (350 MHz, d$_6$-DMSO, δ in ppm, J in Hz): 1.44 (s, 9H, —C(CH$_3$)$_3$; 3.64 and 3.87 (2d, J=18, 2H, —SCH$_2$—); 3.98 (s, 3H, >N—CH$_3$); 4.50 (s, 2H, =NOCH$_2$—); 5.22 (d, J=4, 1H, H in the 6-position); 5.78 (dd, J=4 and 9, 1H, H in the 7-position); 6.77 (s, 1H, H of the thiazole); 6.94 (s, 1H, —COOCH<); 7.0 and 7.08 (2d, J=16, 2H, —CH=CH—); 8.78 (s, 1H, —NHC(C$_6$H$_5$)$_3$); 9.48 (d, J=9, 1H, —CONH—).

Water (10 cc) is added to a solution of product (3c) (3.2 g) in pure formic acid (32 cc) and the mixture is heated at 50° C. for 30 minutes. It is then diluted with water (22 cc) and filtered and the filtrate is concentrated to dryness at 30° C. under 0.05 mm Hg (0.007 kPa). The residue is taken up in ethanol (3×150 cc), each solution being evaporated to dryness at 20° C. under 20 mm Hg (2.7 kPa), the solid obtained is triturated in ethanol (50 cc) and the mixture is filtered. The yellow solid obtained is dissolved in trifluoroacetic acid (11 cc) and the solution is left for 20 minutes at 20° C. and concentrated to dryness at 30° C. under 0.05 mm Hg (0.007 kPa). The residue is taken up in diethyl ether (100 cc), the solution is filtered and the E form of the syn isomer of 7-[2-(2-aminothiazol-4-yl)-2-carboxymethoxyiminoacetamido]-2-carboxy-3-[2-(1-methyltetrazol-5-yl)-thiovinyl]-8-oxo-5-thia-1-azabicyclo[4.2.0]oct-2-ene (product 3) (1.26 g) is obtained in the form of the trifluoroacetate.

Infra-red spectrum (KBr), characteristic bands (cm$^{-1}$): 3,600, 2,200, 1,770, 1,715, 1,675, 1,635, 1,560, 1,200, 945, 805, 720.

Proton NMR spectrum (350 MHz, d$_6$-DMSO, δ in ppm, J in Hz): 3.60 and 3.68 (2d, J=18, 2H, —SCH$_2$—); 4.0 (s, 3H, >N—CH$_3$); 4.59 (s, 2H, =NOCH$_2$—); 5.20 (d, J=4, 1H, H in the 6-position); 5.82 (dd, J=4 and 9, 1H, H in the 7-position); 6.82 (s, 1H, H of the thiazole); 6.98 and 7.11 (2d, J=16, 2H, —CH=CH—); 9.52 (d, J=9, 1H, —CONH—).

EXAMPLE 4

A solution of the E form of the syn isomer of 2-benzhydryloxycarbonyl-7-[2-t-butoxycarbonylmethoxyimino-2-(2-tritylaminothiazol-4-yl)-acetamido]-8-oxo-3-[2-(pyrimidin-2-yl)-thiovinyl]-5-thia-1-azabicyclo[4.2.0]-oct-2-ene (product 4a) (1.2 g) in trifluoroacetic acid (15 cc) is stirred for 15 minutes at 23° C. The solution is evaporated under reduced pressure (0.5 mm Hg; 0.07 kPa) and ether (50 cc) is added. The solidified product is filtered off and the cake is washed with ether and dried at 20° C. under reduced pressure (0.2 mm Hg; 0.03 kPa). The solid obtained is dissolved in formic acid (15 cc), water (5 cc) is added and the mixture is heated for 15 minutes at 50° C. It is concentrated under reduced pressure (0.5 mm Hg; 0.07 kPa) and the residue is taken up in acetone (3×50 cc), each solution being evaporated to dryness at 20° C. under reduced pressure (30 mm Hg; 4 kPa). The solid obtained is triturated in anhydrous ethyl ether (20 cc) for 1 hour, whilst stirring, the mixture is filtered and the material on the filter is washed with ether (6×20 cc) and dried at 20° C. under reduced pressure (0.2 mm Hg; 0.03 kPa) for 15 hours. This yields the E form of the syn isomer of 7-[2-(2-aminothiazol-4-yl)-2-carboxymethoxyiminoacetamido]-2-carboxy-3-[2-(pyrimidin-2-yl)-thiovinyl]-8-oxo-5-thia-1-aza-bicyclo[4.2.0]oct-2-ene (product 4) (0.55 g).

Infra-red spectrum (KBr), characteristic bands (cm$^{-1}$): 3,300 to 3,200, 3,150, 2,100, 1,775, 1,730, 1,680, 1,635, 1,565, 1,550, 1,380, 1,040, 945.

Proton NMR spectrum (350 MHz, d$_6$-DMSO, δ in ppm, J in Hz): 3.75 and 3.94 (2d, J=18, 2H, —SCH$_2$—); 4.63 (s, 2H, =NOCH$_2$—); 5.26 (d, J=4, 1H, H in the 6-position); 5.83 (dd, J=4 and 9, 1H, H in the 7-position); 6.86 (s, 1H, H of the thiazole); 7.21 to 7.53 (2d, J=16, 2H, —CH=CH—); 7.33 (t, J=5, 1H, H in the 4-position of the pyrimidine); 8.72 (d, J=5, 2H, H in the 3-position and 5-position of the pyrimidine); 9.58 (d, J=9, 1H, —CONH—).

By following the procedure of Example 1, using a solution of the E form of the syn isomer of 2-benzhydryloxycarbonyl-7-[2-t-butoxycarbonylmethoxyimino-2-(2-tritylaminothiazol-4-yl)-acetamido]-8-oxo-3-[2-(pyrimidin-2-yl)-thiovinyl]-5-thia-1-azabicyclo[4.2.0]oct-2-ene-5-oxide (product 4b) (1.80 g) in dry methylene chloride (20 cc) and dimethylacetamide (0.85 cc), in the presence of phosphorus trichloride (0.40 cc), as the starting materials, followed by chromatography on a column of Merck silica (0.06–0.2) (30 g) (diameter of the column: 2 cm, height: 20 cm), elution being carried out with a cyclohexane/ethyl acetate mixture (60/40) in 20 cc fractions, and by concentration of fractions 12 to 22 under reduced pressure (30 mm Hg; 4 kPa), product (4a) (1.20 g) is obtained in the form of a hard yellow foam.

Infra-red spectrum (KBr), characteristic bands (cm$^{-1}$): 3,300, 3,060, 3,030, 2,980, 2,920, 1,780, 1,725, 1,690, 1,560, 1,550, 1,525, 1,450, 1,380, 1,300, 1,245, 1,150, 1,090, 940, 745, 700.

Proton NMR spectrum (350 MHz, d$_6$-DMSO, δ in ppm, J in Hz): 1.47 (s, 9H, —C(CH$_3$)$_3$); 3.77 and 3.95 (2d, J=18, 2H, —SCH$_2$—); 4.57 (s, 2H, =NOCH$_2$—); 5.28 (d, J=4, 1H, H in the 6-position); 5.82 (dd, J=9, 1H, H in the 7-position); 6.83 (s, 1H, H of the thiazole); 6.98 (s, 1H, —COOCH<); 7.08 and 7.62 (2d, J=16, 2H, —CH=CH—); 7.25 to 7.55 (aromatic protons); 8.73 (d, J=5, 2H, H in the 3-position and 5-position of the pyrimidine); 8.82 (s, 1H, —N<u>H</u>—C(C$_6$H$_5$)$_3$); 9.58 (d, J=9, 1H, —CONH—).

2-Mercaptopyrimidine (0.162 g) and then diisopropylethylamine (0.23 cc) are added, under nitrogen, in the course of 2 hours, at 20° C., to a solution of the E form of the syn isomer of 2-benzhydryloxycarbonyl-7-[2-t-butoxycarbonylmethoxyimino-2-(2-tritylaminothiazol-4-yl)-acetamido]-8-oxo-3-(2-tosyloxyvinyl)-5-thia-1-azabicyclo[4.2.0]oct-2-ene-5-oxide (product 4c) (1.40 g) in dry dimethylformamide (15 cc). Ethyl acetate (100 cc) is added and this organic solution is washed with water (4×100 cc) and then with a solution of sodium chloride (containing 180 g per liter (2×100 cc). The organic extract is dried over magnesium sulphate and concentrated under reduced pressure (20 mm Hg; 2.7 kPa) and the residue is dried under reduced pressure (0.2 mm Hg; 0.03 kPa) for 15 hours at 20° C. This yields a product (4b) (1.40 g) in the form of a hard yellow foam.

Infra-red spectrum (KBr), characteristic bands, (cm$^{-1}$): 3,300, 1,800, 1,730, 1,690, 1,600, 1,590, 1,565, 1,550, 1,525, 1,495, 1,450, 1,380, 1,065, 945.

EXAMPLE 5

The procedure described in Example 1 is followed, using the E form of the syn isomer of 2-benzhydryloxycarbonyl-7-{2-[(2-t-butoxycarbonylprop-2-yl)-oxyimino]-2-(2-tritylaminothiazol-4-yl)-acetamido}-8-oxo-3-(2-tosyloxyvinyl)-5-thia-1-azabicyclo[4,2,0]oct-2-ene-5-oxide (product 5a) (6.79 g), dimethylformamide (60 cc), 4-(2,2-dimethoxyethyl)-5,6-dioxo-3-thioxo-perhydro-1,2,4-triazine (1.68 g) and N,N-diisopropylethylamine (1.25 cc) as the starting materials. The residue obtained after this treatment is chromatographed on a column of Merck silica gel (0.06–0.2) (125 g) (diameter of the column): 3 cm, height: 43 cm). Elution is carried out with a 50/50 (by volume) cyclohexane/ethyl acetate mixture (1.5 liters) and ethyl acetate (1 liter), 100 cc fractions being collected. Fractions 16 to 21 are concentrated to dryness at 25° C. under 20 mm Hg (2.7 kPa) and this yields the E form of the syn isomer of 2-benzhydryloxycarbonyl-7-{2-[(2-t-butoxycarbonylprop-2-yl)-oxyimino]-2-(2-tritylaminothiazol-4-yl)-acetamido}-3-{2-[4-(2,2-dimethoxyethyl)-5,6-dioxo-1,4,5,6-tetrahydro-1,2,4-triazin-3-yl]-thiovinyl}-8-oxo-5-thia-1-azabicyclo[4.2.0]oct-2-ene-5-oxide (product 5b) (5.5 g) in the form of a hard brown foam.

Infra-red spectrum (CHBr$_3$), characteristic bands (cm$^{-1}$): 1,800, 1,720, 1,690, 1,585, 1,510, 1,495, 1,445, 1,370, 1,080, 1,060, 1,040, 940, 750, 700.

Proton NMR spectrum (350 MHz, DMSOd$_6$, δ in ppm, J in Hz): 1.35 (s, 9H, —C(CH$_3$)$_3$); 1.44 and 1.45 (2s, 6H, =N—O—C(CH$_3$)$_2$—); 3.32 (s, 6H, (—OCH$_3$)$_2$); 3.65 and 4.36 (2d, J=18, 2H, —S—CH$_2$—); 3.95 (d, J=5, 2H, >N—CH$_2$—); 4.56 (t, J=5, 1H,

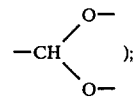);

5.09 (d, J=5, 1H, —H in the 6-position); 5.95 (dd, J=5 and 9, 1H, —H in the 7-position); 6.78 (s, 1H, —H of the thiazole); 7 (s, 1H, —COO—C<u>H</u>(C$_6$H$_5$)$_2$); 7.02 and 7.1 (2d, J=16, 2H, —CH=CH—S—); 8.23 (d, J=9, 1H, —CO—NH—); 8.73 (s, 1H, —N<u>H</u>—C(C$_6$H$_5$)$_3$); 12.65 (s, 1H, =N—NH—CO— or

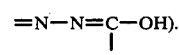

The procedure described in Example 1 is followed, using a solution of product (5b) (5.37 g) in methylene chloride (45 cc) and N,N-dimethylacetamide (1.79 cc), and phosphorus trichloride (0.79 cc), as the starting materials. The residue obtained after the treatment is chromatographed on a column of Merck silica gel (0.06–0.2) (80 g) (diameter of the column: 2 cm, height: 20 cm), elution being carried out with a 40/60 (by volume) cyclohexane/ethyl acetate mixture (250 cc) and a 30/70 mixture (1.5 liters), and 100 cc fractions being collected. Fractions 5 to 14 are concentrated to dryness at 25° C. under 20 mm Hg and this yields the E form of the syn isomer of 2-benzhydryloxycarbonyl-7-{2-[(2-t-butoxycarbonylprop-2-yl)-oxyimino]-2-(-2-tritylaminothiazol-4-yl)acetamido}-3-{2-[4-(2,2-dimethoxyethyl)-5,6-dioxo-1,4,5,6-tetrahydro-1,2,4-triazin-3-yl]-thiovinyl}-8-oxo-5-thia-1-azabicyclo[4.2.0]oct-2-ene (product 5c) (4.02 g) in the form of a hard, light brown foam.

Infra-red spectrum (KBr), characteristic bands (cm$^{-1}$): 1,790, 1,720, 1,690, 1,585, 1,520, 1,495, 1,450, 1,370, 1,080, 940, 750, 700.

Proton NMR spectrum (350 MHz, DMSOd$_6$, δ in ppm, J in Hz): 1.37 (s, 9H, —C(CH$_3$)$_3$); 1.42 (s, 6H, =N—O—C(C<u>H$_3$</u>)$_2$—); 3.31 (s, 6H, (—OCH$_3$)$_2$); 3.64 and 3.89 (2d, J=18, 2H, —S—CH$_2$—); 3.95 (d, J=5, 2H, >N—CH$_2$—); 4.56 (t, J=5, 1H,

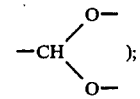);

5.26 (d, J=4, 1H, —H in the 6-position); 5.77 (dd, J=4 and 9, 1H, —H in the 7-position); 6.71 (s, 1H, —H of the thiazole); 6.90 and 7.03 (2d, J=16, 2H, —CH=CH—S—); 6.97 (s, 1H, —COO—C<u>H</u>(C$_6$H$_5$)$_2$); 8.80 (s, 1H, —N<u>H</u>—C(C$_6$H$_5$)$_3$); 9.39 (d, J=9, 1H, —CO—NH—); 12.66 (s, 1H, =N—NH—CO— or

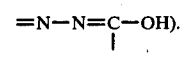

A solution of product (5c) (3.89 g) in trifluoroacetic acid (39 cc) is stirred at 20° C. for 20 minutes. It is concentrated to dryness at 20° C. under 0.05 mm Hg (0.007 kPa), the residue is taken up in diethyl ether (100 cc) and the mixture is stirred for 10 minutes and filtered. The solid obtained is treated at 50° C., for 45 minutes, with formic acid (80 cc), water (16 cc) is added and the mixture is kept at 50° C. for 30 minutes and concentrated to dryness at 20° C. under 0.05 mm Hg (0.007 kPa). The residue is taken up in acetone (3×150 cc), each solution being evaporated at 20° C. under 30 mm Hg (4 kPa), and the residue is heated under reflux in acetone (100 cc), whilst stirring. The mixture is filtered and the E form of the syn isomer of 7-{2-(2-aminothiazol-4-yl)-2-[(2-carboxyprop-2-yl)-oxyimino]-acetamido}-2-carboxy-3-[2-(5,6-dioxo-4-formylmethyl-1,4,5,6-tetrahydro-1,2,4-triazin-3-yl)-thiovinyl]-8-oxo-5-thia-1-azabicyclo[4.2.0]oct-2-ene (product 5) (2.15 g) is collected in the form of a yellow powder.

Infra-red spectrum (KBr), characteristic bands (cm$^{-1}$): 3,400, 3,300, 3,200, 2,200, 1,780, 1,720, 1,685, 1,585, 1,540, 1,000.

Proton NMR spectrum (350 MHz, CF$_3$COOD, δ in ppm, J in Hz): 1.85 and 1.86 (2s, 6H, —CH$_3$); 3.90 (s broad, 2H, —SCH$_2$—); 5.20 (s, 2H, —C$\underline{H}_2$CHO); 5.40 (d, J=4, 1H, H in the 6-position); 6.12 (d, J=4, 1H, H in the 7-position); 7.23 and 7.76 (2d, J=16, 2H, —CH═CH—); 7.50 (s, 1H, H of the thiazole); 9.73 (s, 1H, —CHO).

The product (5a) can be obtained in accordance with one or other of the following methods:

A. A solution of 90% pure m-chloroperbenzoic acid (0.464 g) in methylene chloride (10 cc) is added dropwise, in the course of 25 minutes, to a solution, cooled to 0° C., of the syn isomer of 2-benzhydryloxycarbonyl-7-{2-[(2-t-butoxycarbonylprop-2-yl)-oxyimino]-2-(2-tritylaminothiazol-4-yl)-acetamido}-8-oxo-3-(2-tosyloxyvinyl)-5-thia-1-azabicyclo[4.2.0]oct-2-ene (product 5d) (3 g) in methylene chloride (50 cc). The mixture is stirred for 1 hour at 0° C., diluted with ethyl acetate (500 cc), washed with a 2% strength solution of sodium bicarbonate (2×100 cc), water (2×100 cc) and a saturated aqueous solution of sodium chloride (100 cc), dried over sodium sulphate and filtered and the filtrate is concentrated to dryness at 20° C. under 20 mm Hg (2.7 kPa). The residue is chromatographed on a column of Merck silica gel (0.06–0.2) (60 g) (diameter of the column: 2 cm, height: 20 cm), elution being carried out with a cyclohexane/ethyl acetate mixture (70/30 by volume) (1 liter) and 60 cc fractions being collected. Fractions 5 to 14 are concentrated to dryness at 20° C. under 20 mm Hg (2.7 kPa) and a product (5a) (1.9 g) is collected in the form of a hard yellow foam.

Infra-red spectrum (CHBr$_3$), characteristic bands (cm$^{-1}$): 3,380, 1,800, 1,720, 1,680, 1,590, 1,580, 1,510, 1,490, 1,445, 1,375, 1,190, 1,175, 1,070, 730.

Proton NMR spectrum (350 MHz, d$_6$-DMSO, δ in ppm, J in Hz): 1.37 (s, 9H, —C(CH$_3$)$_3$); 1.45 and 1.46 (2s, 6H, —OC(CH$_3$)$_2$—); 2.44 (s, 3H, —CH$_3$ of the tosyl); 3.60 and 4.41 (2d, J=18, 2H, —SCH$_2$—); 5.06 (d, J=4, 1H, H in the 6-position); 5.96 (dd, J=4 and 9, 1H, H in the 7-position); 6.75 (d, J=13, 1H, —C$\underline{H}$═C-HS—); 6.73 (s, 1H, H of the thiazole); 6.93 (s, 1H, —COOCH—); 7.48 and 7.84 (AB-type, 2H, J=9); 8.16 (d, J=9, 1H, —CONH—); 8.73 (s, 1H, —N$\underline{H}$C(C$_6$H$_5$)$_3$).

Product (5d) can be obtained in the following manner:

p-Toluenesulphonyl chloride (1.31 g) is added to a solution, cooled to 5° C., of the syn isomer of 2-benzhydryloxycarbonyl-7-{2-[(2-t-butoxycarbonylprop-2-yl)-oxyimino]-2-(2-tritylaminothiazol-4-yl)-acetamido}-3-formylmethyl-8-oxo-5-thia-1-azabicyclo[4.2.0]oct-2-ene (product 5e) (4.45 g) in pyridine (50 cc). The temperature is left to rise to 20° C. in the course of 30 minutes, the mixture is stirred for 1 hour at 20° C. and poured into iced water (300 cc), the water is decanted and the insoluble pasty product is taken up in ethyl acetate (300 cc). The solution is washed with 1 N hydrochloric acid (100 cc), a saturated solution of sodium bicarbonate (100 cc) and a saturated solution of sodium chloride (100 cc), dried over sodium sulphate and filtered and the filtrate is concentrated to dryness at 20° C. under 20 mm Hg (2.7 kPa). The product thus obtained is used as such for the remainder of the synthesis. This product (1 g) is purified by chromatography on a column of silica gel (0.05–0.2) (20 g) (diameter of the column: 1.7 cm), elution being carried out with an 80/20 (by volume) mixture of cyclohexane and ethyl acetate, and 50 cc fractions being collected. Fractions 4 to 12, containing the pure product, are evaporated to dryness under reduced pressure (30 mm Hg; 4 kPa) at 30° C. to give a product (5d) (0.43 g), which is a mixture of the E and Z forms (in proportions—determined by NMR—of 75% of the E form and 25% of the Z form), in the form of a pale yellow solid.

Infra-red spectrum (CHBr$_3$), characteristic bands (cm$^{-1}$): 3,400, 3,260, 1,790, 1,720, 1,680, 1,630, 1,595, 1,580, 1,520, 1,490, 1,450, 1,380, 1,370, 1,190, 1,180, 1,070, 835, 750.

Proton NMR spectrum (350 MHz, CDCl$_3$, δ in ppm, J in Hz), mixture of E and Z isomers in the proportions 75/25: E form: 1.45 (s, 9H, —C(CH$_3$)$_3$); 1.62 and 1.67 (2s, 6H, ═N—O—C(CH$_3$)$_2$—); 2.48 (s, 3H, —CH$_3$ of the tosyl); 3.42 and 3.50 (2d, J=18, 2H, —S—CH$_2$—); 5.08 (d, J=4, 1H, —H in the 6-position); 6.00 (dd, J=4 and 9, 1H, —H in the 7-position); 6.78 (s, 1H, H of the thiazole); 6.88 (b, 1H, —N$\underline{H}$—C(C$_6$H$_5$)$_3$); 6.90 and 6.97 (2d, J=12, 2H, —CH═CH—S—); 6.92 (s, 1H, —COO—C$\underline{H}$(C$_6$H$_5$)$_2$; 8.20 (d, J=9, 1H, —CO—NH—). Z form: 6.20 and 6.47 (2d, J=7, —CH═CH—S—Z); 2.45 (s, —CH$_3$ of the tosyl).

The product (5e) can be obtained in the following manner:

A mixture of a solution of the E form of the syn isomer of 2-benzhydryloxycarbonyl-3-(2-dimethylaminovinyl)-7-{2-[(2-t-butoxycarbonylprop-2-yl)-oxyimino]-2-(2-tritylaminothiazol-4-yl)-acetamido}-8-oxo-5-thia-1-azabicyclo[4.2.0]oct-2-ene (product 5f) (6.45 g) in ethyl acetate (100 cc), and of 1 N hydrochloric acid (64 cc), is stirred for 1 hour at 20° C. The organic phase is decanted, washed with water (100 cc), a saturated aqueous solution of sodium bicarbonate (100 cc) and a saturated aqueous solution of sodium chloride (100 cc), dried over sodium sulphate and filtered and the filtrate is concentrated to dryness at 20° C. under 20 mm Hg (2.7 kPa). A crude product (5e) (4.95 g) is collected in the form of hard brown foam.

Infra-red spectrum (CHBr$_3$), characteristic bands (cm$^{-1}$): 3,400, 3,270, 2,720, 1,770, 1,725, 1,685, 1,525, 1,495, 1,450, 1,370, 755, 700.

Proton NMR spectrum (350 MHz, CDCl$_3$, δ in ppm, J in Hz): 1.45 (s, 9H, —C(CH$_3$)$_3$); 1.64 and 1.67 (2s 6H, (—CH$_3$)$_2$); 3.25 and 3.54 (2d, J=18, 2H, —SCH$_2$—); 3.50 and 3.73 (2d, J=16, 2H, —C$\underline{H}_2$CHO); 5.10 (d, J=4, 1H, H in the 6-position); 6.06 (dd, J=4 and 9, 1H, H in the 7-position); 6.77 (s, 1H, H of the thiazole); 6.90 (s, 1H, —COOCH<); 8.22 (d, J=9, 1H, —CONH—); 9.58 (s, 1H, —CHO).

The product (5f) can be obtained in the following manner:

t-Butoxy-bis-dimethylaminomethane (1.9 cc) is added, whilst stirring, to a solution, at 80° C., under nitrogen, of the syn isomer of 2-benzhydryloxycarbonyl-7-{2-[(2-t-butoxycarbonylprop-2-yl)-oxyimino]-2-(2-tritylaminothiazol-4-yl)-acetamido}-3-methyl-8-oxo-5-thia-1-azabicyclo[4.2.0]oct-2-ene (product 5g) (6 g) in dimethylformamide (64 cc), and the reaction is continued for 15 minutes. The mixture is then poured into a mixture of ethyl acetate (200 cc) and water (200 cc), the organic phase is decanted, washed with water (3×100 cc) and a saturated aqueous solution of sodium chloride (100 cc), dried over sodium sulphate and filtered and the filtrate is concentrated to dryness at 20° C. under 20 mm Hg (2.7 kPa). This yields a crude product (5f) (6.5 g) in the form of a hard brown foam.

A sample (2.2 g) is purified by chromatography on a column of Merck silica gel (0.04–0.06, diameter 4 cm., height 20 cm), eluting with a mixture of cyclohexane and ethyl acetate (65:35 by volume) under a pressure of 40 kPa, and collecting fractions of 50 cm$^3$. Fractions 14 to 24 are evaporated to dryness. 2-Benzhydryloxy carbonyl-3-(2-dimethylaminovinyl)-7-{2-[(2-t-butoxycarbonylprop-2-yl)oxyimino]-2-(2-tritylaminothiazol-4-yl)acetamido}-8-oxo-5-thia-1-azabicyclo[4.2.0]oct-2-ene, syn isomer, form E (1.2 g) is thus obtained.

Infra-red spectrum (CHBr$_3$), characteristic bands (cm$^{-1}$): 3,400, 3,280, 1,770, 1,720, 1,680, 1,610, 1,525, 1,490, 1,450, 1,370, 940, 750, 735.

Proton NMR spectrum (350 MHz, CDCl$_3$, δ in ppm, J in Hz): 1.45 (s, 9H, —C(CH$_3$)$_3$); 1.64 and 1.71 (2s, 6H, =N—O—C(CH$_3$)$_2$—); 2.93 (s, 6H, —N(CH$_3$)$_2$); 3.20 and 3.30 (2d, J=14, 2H, —S—CH$_2$—); 5.18 (d, J=4, 1H, —H in the 6-position); 5.71 (dd, J=4 and 9, 1H, —H in the 7-position); 6.61 and 0.82 (2d, J=14, 2H, —CH=CH—S—); 6.88 (s, 1H, H of the thiazole); 6.92 (s, 1H, —COO—CH(C$_6$H$_5$)$_2$); 6.92 (s broad, 1H, —NH—C(C$_6$H$_5$)$_3$); 8.28 (d, J=9, 1H, —CO—NH—).

2-Benzhydryloxycarbonyl-7-{2-[(2-t-butoxycarbonylprop-2-yl)oxyimino]-2-(2-tritylaminothiazol-4-yl)acetamido}-3-methyl-8-oxo-5-thia-1-aza-bicyclo[4.2.0]oct-2-ene, syn isomer can be prepared in the following manner: A solution of phosgene in chlorobenzene (40 cm$^3$ of 1.3 M) is added at −10° C. over 30 minutes and with stirring to a solution of 2-(2-t-butoxycarbonyl-prop-2-yloxyimino)-2-(2-tritylaminothiazol-4-yl) acetic acid (25.58 g., prepared as described in Belgian Pat. No. 876541) in a mixture of dichloromethane (250 cm$^3$) and dimethylacetamide (13.9 cm$^3$). The mixture is then stirred for a further 3 hours at −10° C., after which a solution of 7-amino-2-benzhydryloxycarbonyl-3-methyl-8-oxo-5-thia-1-aza-bicyclo[4.2.0]oct-2-ene (16.29 g) in dichloromethane (250 cm$^3$) is added drop by drop in 1 hour 15 minutes. After 1 hour 15 minutes at −10° C., the mixture is washed with 2% aqueous sodium bicarbonate solution (200 cm$^3$) and water (200 cm$^3$), dried over anhydrous sodium sulphate, and evaporated to dryness at 30° C., under 20 mmHg (2.7 kPa). The residue is chromatographed on a column of Merck silica gel (0.05–0.2, 200 g, diameter of column 4 cm). Elution is effected with a mixture of cyclohexane and ethyl acetate (70:30 by volume) taking fractions of 120 cm$^3$. Fractions 6 to 10 are concentrated to dryness at 30° C. under 20 mmHg (2.7 kPa). 2-Benzhydryloxycarbonyl-7-[2-(2-t-butoxycarbonyl-prop-2-yloxyimino)-2-(2-tritylamino-thiazol-4-yl)acetamido]-3-methyl-8-oxo-5-thia-1-aza-bicyclo[4.2.0]oct-2-ene, syn isomer (8.5 g) is thus obtained as a yellow foam. The infra-red spectrum (in CHBr$_3$) shows characteristic bands at: 3400, 3270, 1790, 1725, 1685, 1525, 1500, 1450, 1380, 1370, 760 and 740.

B. The syn isomer of 2-[(2-t-butoxycarbonylprop-2-yl)-oxyimino]-2-(2-tritylaminothiazol-4-yl)-acetic acid (prepared in accordance with the process described in Belgian Pat. No. 876,541) (11.66 g) and 4-dimethylaminopyridine (0.1 g) are added to a solution of the E form of 7-amino-2-benzhydryloxycarbonyl-8-oxo-3-(2-tosyloxyvinyl)-5-thia-1-azabicyclo[4.2.0]oct-2-ene-5-oxide (product 5h) (9.84 g) in methylene chloride (170 cc). Dimethylformamide (50 cc) is added in order to obtain a limpid solution, the latter is cooled to between 0° C. and 5° C. and a solution of N,N'-dicyclohexylcarbodiimide (4.21 g) in methylene chloride (50 cc) is added in the course of 15 minutes, whilst stirring. The mixture is stirred for 2 hours at 5° C. and 2 hours at 20° C. and concentrated at 20° C. under 20 mm Hg (2.7 kPa). The residue is taken up in ethyl acetate (150 cc), the solution is filtered, the filtrate is washed with water (3×100 cc), a semi-saturated aqueous solution of sodium bicarbonate (2×100 cc) and a semi-saturated solution of sodium chloride (2×100 cc), dried over sodium sulphate and filtered and the filtrate is concentrated to dryness at 20° C. under 20 mm Hg (2.7 kPa). The residue is chromatographed on a column of Merck silica gel (0.06–0.2) (400 g) (diameter of the column: 4 cm, height: 76 cm), elution being carried out with an 80/20 (by volume) cyclohexane/ethyl acetate mixture (1 liter) and a 70/30 mixture (4 liters), and 250 cc fractions being collected. Fractions 6 to 11 are concentrated to dryness at 20° C. under 20 mm Hg (2.7 kPa) and a product (5a) (6.95 g) is collected in the form of a hard yellow foam, the characteristics of which are identical to those of the product (5a) obtained under A.

The preparation of product (5h) has been described above in Example 1 as product (1d).

EXAMPLE 6

The procedure described in Example 1 is followed, but the E form of the syn isomer of 2-benzhydryl oxycarbonyl-7-{2-[(2-t-butoxycarbonylprop-2-yl)-oxyimino]-2-(2-tritylaminothiazol-4-yl)-acetamido}-8-oxo-3-(2-tosyloxyvinyl)-5-thia-1-azabicyclo[4.2.0]oct-2-ene-5-oxide (product 6a) (3.2 g), dimethylformamide (28 cc), 5-mercapto-1-methyltetrazole (0.37 g) and N,N-diisopropylethylamine (0.574 cc) are used as the starting materials. The residue obtained after the treatment is chromatographed on a column of Merck silica gel (0.06–0.2) (70 g) (diameter of the column: 2.3 cm, height: 25 cm). Elution is carried out with a 50/50 (by volume) cyclohexane/ethyl acetate mixture (1 liter, 60 cc fractions being collected. Fractions 6 to 10 are concentrated to dryness at 20° C. under 20 mm Hg (2.7 kPa) and this yields the E form of the syn isomer of 2-benzhydryloxycarbonyl-7-{2-[(2-t-butoxycarbonylprop-2-yl)-oxyimino]-2-(2-tritylaminothiazol-4-yl)-acetamido}-3-[2-(1-methyltetrazol-5-yl)-thiovinyl]-8-oxo-5-thia-1-azabicyclo[4.2.0]oct-2-ene-5-oxide (product 6b) (1.9 g) in the form of a hard brown foam.

Infra-red spectrum (KBr), characteristic bands (cm$^{-1}$): 1,800, 1,730, 1,680, 1,515, 1,495, 1,450, 1,370, 1,045, 940, 750, 700.

Proton NMR spectrum (350 MHz, CDCl$_3$, δ in ppm, J in Hz): 1.44 (s, 9H, —C(CH$_3$)$_3$); 1.58 and 1.60 (2s, 6H, (—CH$_3$)$_2$); 3.93 (s, 3H, >N—CH$_3$); 3.28 and 4.04 (2d, J=18, 2H, —SCH$_2$—); 4.65 (d, J=4, 1H, H in the 6-position); 6.24 (dd, J=4 and 9, 1H, H in the 7-position); 6.76 (s, 1H, H of the thiazole); 6.91 (s, 1H, —COO—CH<); 7.0 and 7.59 (2d, J=16, 2H, —CH=CH—); 7.9 (d, J=9, 1H, —CONH—).

The procedure described in Example 1 is followed, but a solution of product (6b) (1.9 g) in methylene chloride (17 cc) and dimethylacetamide (0.63 cc), and phosphorus trichloride (0.297 cc), are used as the starting materials. The residue (obtained after the treatment as in Example 1) is chromatographed on a column of Merck silica gel (0.06-0.2) (40 g) (diameter of the column: 1.75 cm, height: 20 cm). Elution is carried out with a 50/50 (by volume) cyclohexane/ethyl acetate mixture (1 liter), 60 cc fractions being collected. Fractions 4 to 6 are concentrated to dryness and this yields the E from of the syn isomer of 2-benzhydryloxycarbonyl-7-{2-[(2-t-butoxycarbonylprop-2-yl)-oxyimino]-2-(2-tritylaminothiazol-4-yl)-acetamido}-3-[2-(1-methyltetrazol-5-yl)-thiovinyl]-8-oxo-5-thia-1-azabicyclo[4.2.0]oct-2-ene (product 6c) (0.83 g) in the form of a hard cream-coloured foam.

Infra-red spectrum (KBr), characteristic bands (cm$^{-1}$): 1,790, 1,720, 1,685, 1,520, 1,490, 1,445, 1,370, 750, 700.

Proton NMR spectrum (350 MHz, CDCl$_3$, δ in ppm, J in Hz): 1.43 (s, 9H, —C(CH$_3$)$_3$); 1.62 and 1.66 (2s, 6H, =N—O—C(CH$_3$)$_2$—); 3.6 and 3.7 (2d, J=18, 2H, —S—CH$_2$—); 3.96 (s, 3H, >N—CH$_3$); 5.12 (d, J=4, 1H, —H in the 6-position); 6.05 (dd, J=4 and 9, 1H, —H in the 7-position); 6.75 (s, 1H, —H of the thiazole); 6.9 (s broad, 1H, —NH—C(C$_6$H$_5$)$_3$); 6.95 (s, 1H, —COO—CH(C$_6$H$_5$)$_2$); 7.04 (d, J=16, 1H, —CH=CH—S—); 8.23 (d, J=9, 1H, —CO—NH—).

A solution of product (6c) (0.82 g) in trifluoroacetic acid (10 cc) is stirred at 20° C. for 30 minutes. It is concentrated to dryness at 20° C. under 0.05 mm Hg (0.007 kPa), the residue is taken up in a mixture of formic acid (10 cc) and water (5 cc) and the solution is stirred at 60° C. for 30 minutes and concentrated to dryness at 20° C. under 0.05 mm Hg (0.007 kPa). The residue is taken up in ethanol (3×100 cc), each solution being evaporated to dryness at 20° C. under 30 mm Hg (4 kPa). The solid obtained is dissolved at 60° C. in ethanol (8 cc), diethyl ether (50 cc) is added and the mixture is filtered. The E form of the syn isomer of 7-{2-(2-aminothiazol-4-yl)-2-[(2-carboxyprop-2-yl)-oxyimino]-acetamido}-2-carboxy-3-[2-(1-methyltetrazol-5-yl)-thiovinyl]-8-oxo-5-thia-1-azabicyclo[4.2.0]oct-2-ene (product 6) (0.34 g) is collected in the form of a yellow powder.

Infra-red spectrum (KBr), characteristic bands (cm$^{-1}$): 3,600-2,200, 1,775, 1,675, 1,630, 1,530, 1,385, 990, 950, 700.

Proton NMR spectrum (350 MHz, d$_6$-DMSO, δ in ppm, J in Hz): 1.48 (s, 6H, (—CH$_3$)$_2$); 3.63 and 3.89 (2d, J=18, 2H, —SCH$_2$—); 4.03 (s, 3H, >N—CH$_3$); 5.23 (d, J=4, 1H, H in the 6-position); 5.88 (dd, J=4 and 9, 1H, H in the 7-position); 6.73 (s, 1H, H of the thiazole); 6.97 and 7.10 (2d, J=16, 2H, —CH=CH—); 7.18 (s, 2H, —NH$_2$); 9.42 (d, J=9, —CONH—).

EXAMPLE 7

By following the procedure described in Example 1, but using the E form of the syn isomer of 2-benzhydryloxycarbonyl-7-[2-(1-t-butoxycarbonylcyclobutoxyimino)-2-(2-tritylaminothiazol-4-yl)-acetamido]-8-oxo-3-(2-tosyloxyvinyl)-5-thia-1-azabicyclo[4.2.0]oct-2-ene-5-oxide (product 7a) (2.69 g), dimethylformamide (30 cc), 4-(2,2-dimethoxyethyl)-5,6-dioxo-3-thioxo-perhydro-1,2,4-triazine (0.57 g) and N,N-diisopropylethylamine (0.43 cc) as the starting materials, followed by treatment and chromatography on Merck silica gel (0.06-0.2) [eluent: 40/60 (by volume) cyclohexane/ethyl acetate], the E form of the syn isomer of 2-benzhydryloxycarbonyl-7-[2-(1-t-butoxycarbonylcyclobutoxyimino)-2-(2-tritylaminothiazol-4-yl) acetamido]-3-{2-[4-(2,2-dimethoxyethyl)-5,6-dioxo-1,4,5,6-tetrahydro-1,2,4-triazin-3-yl]-thiovinyl}-8-oxo-5-thia-1-azabicyclo[4.2.0]oct-2-ene-5-oxide (product 7b) (2.5 g) is obtained in the form of a hard yellow foam.

Infra-red spectrum (CHBr$_3$), characteristic bands (cm$^{-1}$): 3,360, 3,240, 1,800, 1,720, 1,680, 1,585, 1,520, 1,490, 1,450, 1,080, 970, 940, 750, 735.

Proton NMR spectrum (350 MHz, CDCl$_3$, δ in ppm, J in Hz): 1.4 (s, 9H, —C(CH$_3$)$_3$); 1.85 to 2.15 (m, 2H, —CH$_2$—CH$_2$—CH$_2$—); 2.3 to 2.8 (m, 4H, —CH$_2$—CH$_2$—CH$_2$—); 3.42 to 3.43 (2s, 6H, (—OCH$_3$)$_2$); 3.48 and 4.19 (2d, J=18, 2H, —S—CH$_2$—); 3.9 to 4.1 (m, 2H, >N—CH$_2$—); 4.66 (t, J=5, 1H,

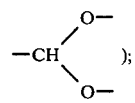

4.84 (d, J=4, 1H, —H in the 6-position); 5.85 (dd, J=4 and 9, 1H, —H in the 7-position); 6.63 (s, 1H, —H of the thiazole); 6.95 (s, 1H, —COO—CH(C$_6$H$_5$)$_2$); 7.08 (d, J=16, —CH=CH—S—); 7.7 (b, 1H, —NH—C(C$_6$H$_5$)$_3$); 7.96 (d, J=9, 1H, —CO—NH—); 12.35 (b, 1H, =N—NH—CO— or

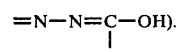

By following the procedure described in Example 1, but using product (7b) (2.37 g), methylene chloride (40 cc), dimethylacetamide (1.55 cc) and phosphorus trichloride (0.695 cc) as the starting materials, followed by treatment and chromatography on Merck silica gel (0.06-0.2) [eluent: 30/70 (by volume) cyclohexane/ethyl acetate], the E forms of the syn isomer of 2-benzhydryloxycarbonyl7-[2-(1-t-butoxycarbonylcyclobutoxyimino)-2-(2-tritylaminothiazol-4-yl)-acetamido]-3-{2-[4-(2,2-dimethoxyethyl)-5,6-dioxo-1,4,5,6-tetrahydro-1,2,4,-triazin-3-yl)]thiovinyl}-8-oxo-5-thia-1-azabicyclo[4.2.0]oct-2-ene (product 7c) (1.5 g) is obtained in the form of a cream-coloured powder.

Infra-red spectrum (CHBr$_3$), characteristic bands (cm$^{-1}$): 3,390, 3,280, 2,840, 1,790, 1,720, 1,695, 1,590, 1,520, 1,495, 1,450, 1,370, 1,080, 950, 750, 700.

Proton NMR spectrum (350 MHz, CDCl$_3$, δ in ppm, J in Hz): 1.48 (s, 9H, —C(CH$_3$)$_3$); 2 to 2.10 (m, 2H, —CH$_2$—CH$_2$—CH$_2$—); 2.50 to 2.7 (m, 4H, —CH$_2$—CH$_2$—CH$_2$—); 3.45 (s, 6H, (—OCH$_3$)$_2$); 3.61 (limiting AB-type, 2H, —S—CH$_2$—); 4.03 (d, J=6, 2H, >N—CH$_2$—); 4.69 (t, J=6, 1H,

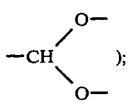

5.13 (d, J=4, 1H, —H in the 6-position); 5.98 (dd, J=4 and 9, 1H, —H in the 7-position); 6.79 (s, 1H, H of the thiazole); 6.83 (d, J=15, 1H, —C$\underline{H}$═CH—S—); 6.98 (s, 1H, —COO—C$\underline{H}$(C$_6$H$_5$)$_2$); 8.60 (d, J=9, 1H, —CO—NH—); 10.70 (b broad, 1H, ═N—NH—CO— or

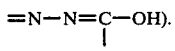

A solution of product (7c) (1.5 g) in trifluoroacetic acid (15 cc) is stirred at 20° C. for 30 minutes and concentrated to dryness at 20° C. under 0.05 mm Hg (0.007 kPa), the residue is triturated in diethyl ether (50 cc) and the mixture is filtered. The cream-coloured solid obtained is heated for 15 minutes, at 50° C., in a mixture of formic acid (15 cc) and water (7 cc), the resulting mixture is concentrated to dryness at 30° C. under 0.05 mm Hg (0.007 kPa) and the residue is taken up in acetone (3×20 cc), each solution being concentrated to dryness at 20° C. under 20 mm Hg (2.7 kPa). The residue is heated under reflux in acetone (20 cc), the mixture is filtered and the E form of the syn isomer of 7-[2-(2-aminothiazol-4-yl)-2-(1-carboxycyclobutoxyimino)acetamido]-2-carboxy-3-[2-(5,6-dioxo-4-formylmethyl-1,4,5,6-tetrahydro-1,2,4-triazin-3-yl)-thiovinyl]-8-oxo-5-thia-1-azabicyclo[4.2.0]oct-2-ene (product 7) (0.75 g) is collected in the form of a yellow powder.

Infra-red spectrum (KBr), characteristic bands (cm$^{-1}$): 3,400, 3,300, 3,220, 3,100, 2,200, 1,780, 1,715, 1,685, 1,585, 1,535, 1,055, 945.

Proton NMR spectrum (350 MHz, CF$_3$COOD, δ in ppm, J in Hz): 2.20 to 2.32 (m, 2H, —CH$_2$—C$\underline{H}$$_2$—CH$_2$—); 2.65 to 2.95 (m, 4H, —C$\underline{H}$$_2$—CH$_2$—C$\underline{H}$$_2$—); 3.90 (s broad, 2H, —S—CH$_2$—); 5.20 (s, 2H, >N—CH$_2$—); 5.40 (d, J=4, 1H, —H in the 6-position); 6.14 (d, J=4, 1H, —H) in the 7-position); 7.24 and 7.75 (2d, J=16, 2H, —CH═CH—S—); 7.49 (s, 1H, H of the thiazole); 9.78 (s, 1H,

Product (7a) can be prepared in the following manner:

The syn isomer of 2-(1-t-butoxycarbonylcyclobutoxyimino)-2-(2-tritylaminothiazol-4-yl)-acetic acid prepared according to Belgian Patent 876,541 (4.42 g) and 4-dimethylaminopyridine (0.25 g) are added to a solution of the E form of 7-amino-2-benzhydryloxycarbonyl-8-oxo-3-(2-tosyloxyvinyl)-5-thia-1-azabicyclo[4.2.0]oct-2-ene-5-oxide (product 7d) (4.34 g) in methylene chloride (50 cc). The mixture is cooled to 5° C. and a solution of N,N'-dicyclohexylcarbodiimide (1.69 g) in methylene chloride (30 cc) is added dropwise in the course of 10 minutes. The temperature is left to rise, the mixture is stirred for 4 hours at 20° C. and concentrated to dryness at 20° C. under 20 mm Hg (2.7 kPa) and the residue is taken up in ethyl acetate (200 cc). The solution is washed with water (2×100 cc), 0.1 N hydrochloric acid (100 cc), a saturated aqueous solution of sodium bicarbonate (100 cc) and water (100 cc), dried over sodium sulphate and filtered and the filtrate is concentrated to dryness at 25° C. under 20 mm Hg (2.7 kPa). The residue is chromatographed on a column of Merck silica gel (0.06–0.2) (180 g) (diameter of the column: 3 cm, height: 60 cm). Elution is carried out with a 70/30 (by volume) cyclohexane/ethyl acetate mixture (1 liter), 60 cc fractions being collected. Fractions 6 to 10 are concentrated to dryness at 20° C. under 20 mm Hg (2.7 kPa) and this yields a product (7a) (2.7 g) in the form of a cream-coloured powder.

Infra-red spectrum (CHBr$_3$), characteristic bands (cm$^{-1}$): 3,390, 1,800, 1,720, 1,680, 1,595, 1,495, 1,450, 1,520, 1,370, 1,190, 1,180, 1,070, 940, 830, 750, 700.

Proton NMR spectrum (350 MHz, CDCl$_3$, δ in ppm, J in Hz): 1:45 (s, 9H, —C(CH$_3$)$_3$); 1.92 to 2.12 (m, 2H, —CH$_2$—C$\underline{H}$$_2$—CH$_2$—); 2.40 to 2.65 (m, 4H, —C$\underline{H}$$_2$—CH$_2$—C$\underline{H}$$_2$—); 2.48 (s, 3H, —CH$_3$ of the tosyl); 3.15 and 3.71 (2d, J=18, 2H, —S—CH$_2$—); 4.6 (d, J=4, 1H, —H in the 6-position); 6.17 (dd, J=4 and 9, 1H, —H in the 7-position); 6.75 (s, 1H, —H of the thiazole); 6.91 (s, 1H, —COO—C$\underline{H}$(C$_6$H$_5$)$_2$); 6.92 and 7.09 (2d, J=12, 2H, —CH═CH—S); 6.99 (s, 1H, —N$\underline{H}$—C(C$_6$H$_5$)$_3$); 8.02 (d, J=9, 1H, —CO—NH—);

EXAMPLE 8

A solution of the E form of the syn isomer of 2-benzhydryloxycarbonyl-7-[2-methoxyimino-2-(2-tritylaminothiazol-4-yl)-acetamido]-8-oxo-3-(2-tosyloxyvinyl)-5-thia-1-azabicyclo[4.2.0]oct-2-ene (product 8a, prepared as described in Belgian Pat. No. 883415 (5.85 g) and the sodium salt of 5,6-dioxo-4-[N-(2-hydroxyethyl)carbamoylmethyl]-3-thioxo-perhydro-1,2,4-triazine (1.59 g) in N,N-dimethylformamide (120 cc) is heated at 60° C. for 1½ hours and then poured into distilled water (800 cc). Extraction is carried out with ethyl acetate (3×200 cc) and the extracts are washed with a semi-saturated solution of sodium chloride (2×200 cc). After drying over magnesium sulphate and evaporating off the solvent under reduced pressure (30 mm Hg; 4 kPa) at 30° C., the residue is chromatographed on a column of silica (0.04–0.06) (diameter of the column: 4 cm, height: 30 cm), elution being carried out under 60 kPa with a mixture of methylene chloride and methanol (95/5 by volume) and 100 cc fractions being collected. Fractions 15 to 21, containing the pure product, are combined and concentrated to dryness under reduced pressure (30 mm Hg: 4 kPa) at 30° C. This yields the E form of the syn isomer of 2-benzhydryloxycarbonyl-3-{2-{5,6-dioxo-4-[N-(2-hydroxyethyl)-carbamoylmethyl]-1,4,5,6-tetrahydro-1,2,4-triazin-3-yl}-thiovinyl}-7-[2-methoxyimino-2-(2-tritylaminothiazol-4-yl)-acetamido]-8-oxo-5-thia-1-azabicyclo[4.2.0]oct-2-ene (product 8b) (2 g) in the form of a hard yellow foam.

Infra-red spectrum (CHBr$_3$), characteristic bands (cm$^{-1}$): 3,360, 3,200, 1,780, 1,720, 1,675, 1,590, 1,520, 1,490, 1,445, 1,045, 940, 750, 740.

Proton NMR spectrum (350 MHz, DMSOd$_6$, δ in ppm, J in Hz): 3.18 (m, 2H, —CONH—C$\underline{H}$$_2$—); 3.42 (m, 2H, —CH$_2$—O—); 3.62 and 3.87 (2d, J=18, 2H, —S—CH$_2$—); 3.83 (s, 3H, ═N—OCH$_3$); 4.48 (s broad, 2H, >N—CH$_2$—); 4.71 (t, J=5, 1H, —OH); 5.25 (d, J=4, 1H, —H in the 6-position); 5.76 (dd, J=4 and 9, 1H, —H in the 7-position); 6.74 (s, 1H, H of the thiazole); 6.88 and 6.97 (2d, J=16, 2H, —CH=CH—S—); 6.96 (s, 1H, —COO—C$\underline{H}$(C$_6$H$_5$)$_2$); 8.30 (t, J=5.5, 1H, —CO—N$\underline{H}$—CH$_2$—); 8.80 (s, 1H, —N$\underline{H}$—C(C$_6$H$_5$)$_3$); 9.59 (d, J=9, 1H, —CO—NH—); 12.69 (s, 1H, =N—NH—CO— or

A solution of product (8b) (2 g) in formic acid (25 cc) and distilled water (10 cc) is heated at 50° C. for 50 minutes and then cooled to 25° C. After the insoluble material has been filtered off, the filtrate is concentrated under reduced pressure (2 mm Hg; 0.27 kPa) at 30° C. The residue is triturated with anhydrous ethanol (30 cc), which is then evaporated off under reduced pressure (30 mm Hg; 4 kPa) at 30° C. This operation is repeated 3 times and the residue is then taken up in ethanol (30 cc). The solid is filtered off and washed with ethanol (3×20 cc) and ethyl ether (3×20 cc). This yields the E form of the syn isomer of 7-[2-(2-aminothiazol-4-yl)-2-methoxyiminoacetamido]-2-carboxy-3-{2-{5,6-dioxo-4-[N-(2-hydroxyethyl)-carbamoylmethyl]-1,4,5,6-tetrahydro-1,2,4-triazin-3-yl}-thiovinyl}-8-oxo-5-thia-1-azabicyclo[4.2.0]oct-2-ene (product 8) (1.22 g) in the form of a yellow solid.

Infra-red spectrum (KBr), characteristic bands (cm$^{-1}$): 3,600–2,700, 1,770, 1,715, 1,675, 1,590, 1,550, 1,040, 945.

Proton NMR spectrum (350 MHz, DMSOd$_6$, δ in ppm, J in Hz): 3.20 to 3.60 (m, >N—CH$_2$—CH$_2$—O—); 3.62 and 3.84 (2d, J=18, 2H, —S—CH$_2$—); 3.85 (s, 3H, =N—OCH$_3$); 4.12 (t, J=7, 1H, —OH); 4.50 (s, 2H, >N—CH$_2$—); 5.20 (d, J=4, 1H, —H in the 6-position); 5.79 (dd, J=4 and 9, 1H, —H in the 7-position); 6.74 (s, 1H, H of the thiazole) 6.85 and 7.07 (2d, J=16, 2H, —CH=CH—S—); 7.18 (s, 2H, —NH$_2$); 8.45 (t, J=6, —CO—N$\underline{H}$—CH$_2$—); 9.60 (d, J=9, 1H, —CO—NH—); 12.70 (s, 1H, =N—NH—CO— or

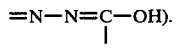

5,6-Dioxo-4-[N-(2-hydroxyethyl)-carbamoylmethyl]-3-thioxo-perhydro-1,2,4-triazine can be prepared in the following manner:

4-[N-(2-Hydroxyethyl)-carbamoylmethyl]-thiosemicarbazide (1.92 g) and ethyl oxalate (1.33 cc) are added to a solution of sodium (0.23 g) in dry methanol (15 cc) at 25° C. The reaction mixture is heated at the reflux temperature for 2½ hours. After cooling to about 25° C., the solid is isolated on a vacuum filter, washed with methanol (5 cc) and ethyl ether (20 cc) and dried. This yields the sodium salt of 5,6-dioxo-4-[N-(2-hydroxyethyl)carbamoylmethyl]-3-thioxo-perhydro-1,2,4-triazine (1.65 g) in the form of a pink solid.

Infra-red spectrum (KBr), characteristic bands (cm$^{-1}$): 3,400, 3,300, 1,695, 1,660, 1,645, 1,590, 1,070.

4-[N-(2-Hydroxyethyl)-carbamoylmethyl]-thiosemicarbazide can be prepared in the following manner:

4-Ethoxycarbonylmethylthiosemicarbazide (5 g) is treated in ethanol (60 cc) with 2-hydroxyethylamine (1.7 g), for 1 hour, at the reflux temperature of the reaction mixture, and the mixture is then concentrated to dryness under reduced pressure (30 mm Hg; 4 kPa) at 40° C. This yields 4-[N-(2-hydroxyethyl)-carbamoylmethyl]-thiosemicarbazide (5.4 g) in the form of an oil, which crystallises slowly.

Proton NMR spectrum (60 MHz, d$_6$-DMSO, δ in ppm, J in Hz): 3.25 (t, J=6, 2H, —CH$_2$OH); 3.40 (q, J=6, 2H, —NHCH$_2$CH$_2$OH); 4.13 (s broad, 2H, —NHCH$_2$CO—); 4.66 (m, 3H, —NH$_2$ and —OH); 7.9 (m, 2H,

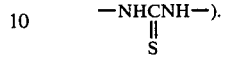

EXAMPLE 9

The E form of the syn isomer of 2-benzhydryloxycarbonyl-7-[2-methoxyimino-2-(2-tritylaminothiazol-4-yl)acetamido]-8-oxo-3-(2-tosyloxyvinyl)-5-thia-1-azabicyclo[4.2.0]oct-2-ene-5-oxide (product 9a) (6 g) is treated with 1-(2,2-diethoxyethyl)-5,6-dioxo-4-methyl-3-thioxoperhydro-1,2,4-triazine (1.65 g) in N,N-dimethylformamide (60 cc), at 60° C., in the presence of N,N-diisopropylethylamine (1.05 cc), in accordance with the procedure described in Example 1. This yields the E form of the syn isomer of 2-benzhydryloxycarbonyl-3-{2-[1-(2,2-diethoxyethyl)-5,6-dioxo-4-methyl-1,4,5,6-tetrahydro-1,2,4-triazin-3-yl]-thiovinyl}-7-[2-methoxyimino-2-(2-tritylaminothiazol-4-yl)-acetamido]-8-oxo-5-thia-1-azabicyclo[4.2.0]oct-2-ene-5-oxide (product 9b) (2.57 g) in the form of a hard orange foam.

Infra-red spectrum (CHBr$_3$), characteristic bands (cm$^{-1}$): 3,380, 2,820, 1,800, 1,715, 1,680, 1,585, 1,515, 1,495, 1,445, 1,050, 940, 750.

Proton NMR spectrum (350 MHz, DMSOd$_6$, δ in ppm, J in Hz): 1.07 and 1.08 (2t, J=7, 6H, 2—CH$_3$); 3.28 (s, >N—CH$_3$); 3.40 to 3.70 (2m, 4H, (—O—C$\underline{H}$$_2$—CH$_3$)$_2$); 3.62 and 4.36 (2d, J=18, 2H, —S—CH$_2$—); 3.85 (s, 3H, =N—OCH$_3$); 3.95 (limiting AB-type, 2H, >N—CH$_2$—); 4.85 (t, J=6, 1H,

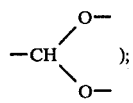

5.08 (d, J=4, 1H, —H in the 6-position); 5.87 (dd, J=4 and 9, 1H, —H in the 7-position); 6.80 (s, 1H, —H of the thiazole); 6.99 (s, 1H, —COO—CH(C$_6$H$_5$)$_2$); 7.05 and 7.18 (2d, J=16, 2H, —CH=CH—S—); 8.79 (s, 1H, —NH—C(C$_6$H$_5$)$_3$); 9.12 (d, J=9, 1H, —CO—NH—).

Rf=0.3, Merck silica gel chromatography plate [eluent: 20/80 by volume mixture of cyclohexane and ethyl acetate].

Product (9b) (2.3 g) is treated with phosphorus trichloride (0.44 cc) in accordance with the procedure of Example 1. This yields the E form of the syn isomer of 2-benzhydryloxycarbonyl-3-{2-[1-(2,2-diethoxyethyl)-5,6-dioxo-4-methyl-1,4,5,6-tetrahydro-1,2,4-triazin-3-yl]thiovinyl}-7-[2-methoxyimino-2-(2-tritylaminothiazol-4-yl)-acetamido]-8-oxo-5-thia-1-azabicyclo[4.2.-0]oct-2-ene (product 9c) (2 g) in the form of a hard yellow foam.

Infra-red spectrum (CHBr$_3$), characteristic bands (cm$^{-1}$): 3,390, 2,820, 1,785, 1,715, 1,680, 1,585, 1,515, 1,490, 1,455, 1,050, 940, 750, 740.

Proton NMR spectrum (350 MHz, DMSOd$_6$, δ in ppm, J in Hz): 1.07 (t, J=7, 6H, 2—CH$_3$); 3.30 (s, >N—CH₃); 3.40 to 3.68 (2m, 4H, (—O—C$\underline{H}$₂—CH₃)₂); 3.68 and 3.92 (2d, J=18, 2H, —S—CH₂—); 3.83 (s, 3H, =N—OCH₃); 3.95 (d, J=6, 2H, >N—CH₂—); 4.85 (t, J=6, 1H,

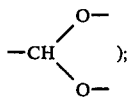

5.27 (d, J=4, 1H, —H in the 6-position); 5.79 (dd, J=4 and 9, 1H, —H in the 7-position); 6.75 (s, 1H, —H of the thiazole); 6.96 (s, 1H, —COO—C$\underline{H}$(C₆H₅)₂); 6.98 and 7.05 (2d, J=16, 2H, —CH=CH—S—); 8.82 (s, 1H, —NH—C(C₆H₅)₃); 9.63 (d, J=9, 1H, —CO—NH—).

A solution of product (9c) (1.9 g) in formic acid (20 cc) is stirred for 30 minutes at 50° C. and then diluted with water (2 cc) and stirred for 10 minutes at 50° C. After cooling to 20° C., the reaction mixture is filtered and the filtrate is concentrated under reduced pressure (0.1 mm Hg; 0.013 kPa) at 35° C. The residue is triturated with ethanol (20 cc), which is evaporated off under reduced pressure (30 mm Hg; 4 kPa) at 40°. This operation is repeated 3 times and the residue is then taken up in ethanol (30 cc). The solid is isolated on a vacuum filter, washed with ethanol (3×10 cc) and with ethyl ether (3×10 cc) and dried. This yields the E form of the syn isomer of 7-[2-(2-aminothiazol-4-yl)-2--methoxyiminoacetamido]-2-carboxy-3-[2-(5,6-dioxo-1-formylmethyl-4-methyl-1,4,5,6-tetrahydro-1,2,4-triazin-3-yl)thiovinyl]-8-oxo-5-thia-1-azabicyclo[4.2.0]oct-2-ene (product 9) (0.96 g) in the form of a cream-coloured solid.

Infra-red spectrum (KBr), characteristic bands (cm⁻¹): 3,700–2,200, 1,770, 1,710, 1,675, 1,580, 1,550, 1,040.

Proton NMR spectrum (350 MHz, CF₃COOD, δ in ppm, J in Hz): 3.66 (s, 3H, >N—CH₃); 3.85 (s broad, 2H, —S—CH₂—); 4.31 (s, 3H, =N—O—CH₃); 5.13 (s broad, 2H, >N—CH₂—); 5.38 (d, J=4, 1H, —H in the 6-position); 6.02 (d, J=4, 1H, —H in the 7-position); 7.22 and 7.73 (2d, J=16, 2H, —CH=CH—S—); 7.48 (s, 1H, —H of the thiazole); 9.74 (s, 1H,

1-(2,2-Diethoxyethyl)-5,6-dioxo-4-methyl-3-thioxoperhydro-1,2,4-triazine can be prepared in the following manner:

1-(2,2-Diethoxyethyl)-1-ethoxalyl-4-methyl-thiosemicarbazide (8.8 g) is treated with potassium t-butylate (3.08 g) in dry t-butanol (60 cc) for 2 hours at 25° C. The reaction mixture is diluted with ether (50 cc). The precipitate of the potassium salt of the expected product is isolated on a filter, washed with ether (10 cc) and then taken up in water (30 cc). The solution obtained is acidified to pH 3 with 4 N hydrochloric acid. The precipitate is isolated on a filter, washed with water (10 cc) and ethyl ether (10 cc) and then dried under reduced pressure (2 mm Hg; 0.27 kPa) at 20° C. This yields 1-(2,2-diethoxyethyl)-5,6-dioxo-4-methyl-3-thioxo-perhydro-1,2,4-triazine (3.65 g) in the form of white crystals, m.p.=136°–138° C.

1-(2,2-Diethoxyethyl)-1-ethoxalyl-4-methyl-thiosemicarbazide can be obtained in the following manner:

1-(2,2-Diethoxyethyl)-4-methyl-thiosemicarbazide (19.4 g) is treated in dry methylene chloride (200 cc) with pyridine (7.1 cc) and ethoxalyl chloride (9.85 cc) for 1 hour at 2° C. and then 16 hours at 25° C.; after the mixture has been washed with water (100 cc), dried over magnesium sulphate and concentrated to dryness under reduced pressure (30 mm Hg; 4 kPa) at 30° C., the residue is crystallised from ethyl ether (40 cc). This yields 1-(2,2-diethoxyethyl)-1-ethoxalyl-4-methyl-thiosemicarbazide (8.5 g) in the form of white crystals (m.p.=122° C.).

1-(2,2-Diethoxyethyl)-4-methyl-thiosemicarbazide can be prepared in the following manner:

1-(2,2-Diethoxyacetyl)-4-methyl-thiosemicarbazide (39.3 g) is reduced with lithium aluminium hydride (18 g) in dry tetrahydrofuran (500 cc) for 1 hour 30 minutes at 25° C. and then 1 hour under reflux. This yields 1-(2,2-diethoxyethyl)-4-methyl-thiosemicarbazide (26.4 g) in the form of a colourless oil.

Infra-red spectrum (CCl₄), characteristic bands (cm⁻¹): 3,360, 3,200, 1,550, 1,240, 1,130, 1,060.

Mass spectrum: m/e=221, 175, 146.

1-(2,2-Diethoxyacetyl)-4-methyl-thiosemicarbazide can be prepared in the following manner:

Diethoxyacetic acid hydrazide (31.5 g) is treated in ethyl ether (200 cc) with methyl isothiocyanate (14.6 g) for 20 hours at between 20° and 30° C. 1-(2,2-diethoxyacetyl)-4-methyl-thiosemicarbazide crystallizes from the medium.

(Weight: 42 g; m.p.=116°–118° C.).

EXAMPLE 10

By following an analogous procedure to Example 9, the E form of the syn isomer of 7-[2-(2-aminothiazol-4-yl)-2-methoxyiminoacetamido]-2-carboxy-3-[2-(5,6-dioxo-4-formylmethyl-1-methyl-1,4,5,6-tetrahydro-1,2,4-triazin-3-yl)-thiovinyl]-8-oxo-5-thia-1-azabicyclo[4.2.0]oct-2-ene is obtained in the form of a yellow powder (product 10).

Infra-red spectrum (KBr), characteristic bands (cm⁻¹): 3,600 to 2,300, 1,770, 1,710, 1,670, 1,575, 1,040, 945.

Proton NMR spectrum (350 MHz, CF₃COOD, δ in ppm, J in Hz): 3.82 (s, broad, 2H, —SCH₂—); 3.88 (s, 3H, >N—CH₃); 4.32 (s, 3H, —OCH₃); 5.18 (s, 2H, >NCH₂); 5.40 (d, J=4, 1H, H in the 6-position); 6.04 (d, J=4, 1H, H in the 7-position); 7.24 and 7.73 (2d, J=16, 2H, —CH=CH—S—); 7.48 (s, 1H, H of the heterocyclic ring); 9.73 (s, 1H, —CHO).

EXAMPLE 11

A mixture of the E form of 7-amino-2-benzhydryloxycarbonyl-3-{2-[4-(2,2-dimethoxyethyl)-5,6-dioxo-1,4,5,6-tetrahydro-1,2,4-triazin-3-yl]-thiovinyl}-8-oxo-5-thia-1-azabicyclo[4.2.0]oct-2-ene-5-oxide methanesulphonate (product 11a) (0.14 g), methylene chloride (30 cc) and a semi-saturated solution of sodium bicarbonate (10 cc) is stirred for 10 minutes at 20° C. and the organic phase is decanted, washed with a saturated solution of sodium chloride (15 cc), dried over sodium sulphate and filtered. The filtered solution is treated with the syn isomer of 2-t-butoxycarbonylmethoxyimino-2-(2-tritylaminothiazol-4-yl)-acetic acid (prepared according to Belgian Pat. No. 865,298) (0.156 g) and with 4-dimethylaminopyridine (5 mg). The mixture is cooled to 5° C., a solution of N,N'-dicyclohexylcarbodiimide (50 mg) in methylene chloride (1 cc) is added dropwise in the course of 3 minutes and the temperature is left to rise to 20° C. in the course of 3 hours. The mixture is washed with a 2% strength solution of sodium bicarbonate (20 cc) and a semi-saturated solution of sodium chloride (20 cc), dried over sodium sulphate and filtered and the filtrate is concentrated to dryness at 20° C. under 20 mm Hg (2.7 kPa). The residue is chromatographed on a column of Merck silica gel (0.04–0.06) (diameter of the column: 1.8 cm; height: 9 cm); elution is carried out with a 20/80 (by volume) cyclohexane/ethyl acetate mixture (200 cc) under a pressure of 40 kPa, 10 cc fractions being collected. Fractions 6 to 14 are concentrated to dryness at 20° C. under 20 mm Hg (2.7 kPa) and the E form of the syn isomer of 2-benzhydryloxycarbonyl-7-[2-t-butoxycarbonylmethoxyimino-2-(2-tritylaminothiazol-4-yl)-acetamido]-3-{2-[4-(2,2-dimethoxyethyl)-5,6-dioxo-1,4,5,6-tetrahydro-1,2,4-triazin-3-yl]-thiovinyl}-8-oxo-5-thia-1-azabicyclo[4.2.0]oct-2-ene-5-oxide (product 11b) (50 mg) is collected, the infra-red and NMR characteristics of which are identical to those of product (1b) described in Example 1.

By following the procedure described in Example 1, the E form of the syn isomer of 2-benzhydryloxycarbonyl-7-[2-t-butoxycarbonylmethoxyimino-2-(2-tritylaminothiazol-4-yl)-acetamido]-3-{2-[4-(2,2-dimethoxyethyl)-5,6-dioxo-1,4,5,6-tetrahydro-1,2,4-triazin-3-yl]-thiovinyl}-8-oxo-5-thia-1-azabicyclo[4.2.0]oct-2-ene (product 11c) is obtained, and then the E form of the syn isomer of 7-[2-(2-aminothiazol-4-yl)-2-carboxymethoxyiminoacetamido]-2-carboxy-3-[2-(5,6-dioxo-4-formylmethyl-1,4,5,6-tetrahydro-1,2,4-triazin-3-yl)-thiovinyl]-8-oxo-5-thia-1-azabicyclo[4.2.0]oct-2-ene (product 11) is obtained, the characteristics of which are identical to those of product (1) described above in Example 1.

Product (11a) can be prepared in the following manner:

The E isomer of 2-benzhydryloxycarbonyl-7-t-butoxycarbonylamino-3-{2-[4-(2,2-dimethoxyethyl)-5,6-dioxo-1,4,5,6-tetrahydro-1,2,4-triazin-3-yl]-thiovinyl}-8-oxo-5-thia-1-azabicyclo[4.2.0]oct-2-ene-5-oxide (product 11d) (5 g) is added to an acetonitrile/methanol mixture (85/15 by volume) (80 cc), and methanesulphonic acid (6 g) is then added. The mixture has become limpid. It is left for 5 hours at 20° C., whilst stirring, and the white precipitate formed is filtered off. The precipitate is washed with acetonitrile (2×10 cc), ethyl acetate (2×25 cc) and then ethyl ether (2×25 cc). After drying in vacuo (0.5 mm Hg; 0.07 kPa), the methanesulphonate of product (11a) (4.4 g) is obtained in the form of white crystals.

Infra-red spectrum (KBr), characteristic bands (cm$^{-1}$): 3,300, 2,200, 1,800, 1,720, 1,590, 1,495, 1,455, 1,220, 1,125, 1,085, 1,080, 1,045, 945, 760, 710, 620, 600, 560.

Proton NMR spectrum (80 MHz, d$_6$-DMSO, δ in ppm, J in Hz): 2.48 (s, 3H, C$\underline{H}_3$SO$_3$H); 3.38 (s, 6H, (—OCH$_3$)$_2$); 3.74 and 4.45 (2d, J=18, 2H, —SCH$_2$—); 3.98 (d, J=5, 2H, >NCH$_2$—); 4.58 (t, J=5, 1H, —C$\underline{H}$(OCH$_3$)$_2$); 5.06 (d, J=4, 1H, H in the 6-position); 5.38 (d, J=4, 1H, H in the 7-position); 7.0 (s, 1H, —COO—C$\underline{H}$<).

Product (11d) can be obtained in accordance with one or other of the following methods:

A. A solution of the E form of 2-benzhydryloxycarbonyl-7-t-butoxycarbonylamino-3-(2-chlorovinyl)-8-oxo-5-thia-1-azabicyclo[4.2.0]oct-2-ene-5-oxide (product 11e) (0.54 g), 4-(2,2-dimethoxyethyl)-5,6-dioxo-3-thioxoperhydro-1,2,4-triazine (0.25 g) and N,N-diisopropylethylamine (0.19 cc) in dry N,N-dimethylformamide (8 cc) is heated at 60° C. for 4 hours and then stirred for 16 hours at 25° C. and diluted with methylene chloride (100 cc). The solution is washed successively with a semi-saturated solution of sodium chloride (2×50 cc), a semi-saturated solution of sodium bicarbonate (2×50 cc) and distilled water (2×50 cc). After the organic layer has been dried over sodium sulphate and concentrated to dryness under reduced pressure (30 mm Hg; 4 kPa) at 35° C., the residue is chromatographed on a column of silica gel (0.04–0.06) (diameter of the column: 2 cm; height: 30 cm), elution being carried out with ethyl acetate under 50 kPa, and 30 cc fractions being collected. Fractions 12 to 16 are combined and concentrated to dryness under reduced pressure (30 mm Hg; 4 kPa) at 35° C. This yields a product (11d) (0.4 g) in the form of an amorphous orange solid. This product is crystallised from a mixture of isopropyl ether and acetonitrile (75/25 by volume) (20 cc). This yields the crystalline product (0.15 g), the characteristics of which are as follows:

Infra-red spectrum (KBr), characteristic bands (cm$^{-1}$): 3,410, 1,790, 1,715, 1,580, 1,490, 1,450, 1,155, 1,115, 1,075, 1,040, 935, 750, 740, 695.

Proton NMR spectrum (80 MHz, d$_6$-DMSO, δ in ppm, J in Hz): 1.45 (s, 9H, (CH$_3$)$_3$C—); 3.62 and 4.42 (2d, J=18.5, 2H, —S(O)CH$_2$—); 3.33 (s, 6H, —CH(OCH$_3$)$_2$); 3.97 (d, J=5, 2H, —C$\underline{H}_2$CH(OCH$_3$)$_2$); 4.55 (t, J=5, 1H, —C$\underline{H}$(OCH$_3$)$_2$); 5.04 (d, J=4, 1H, H in the 6-position); 5.80 (dd, J=4 and 9, 1H, H in the 7-position); 6.40 (d, J=9, —CON$\underline{H}$—C$_7$); 6.98 (s, 1H, —C$\underline{H}$(C$_6$H$_5$)$_2$); 7.08 (limiting AB-type, 2H, —CH=CH—S—); 7.2 to 7.50 (m, 10H, aromatic); 12.68 (s, 1H,

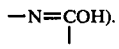

Product (11e) can be prepared in the following manner:

A solution of 2-benzhydryloxycarbonyl-7-t-butoxycarbonylamino-3-(2,2-dichloroethyl)-8-oxo-5-thia-1-azabicyclo[4.2.0]oct-2-ene-5-oxide (product 11f) (3.3 g) and triethylamine (0.88 cc) in dry tetrahydrofuran (50 cc) is stirred at 25° C. for 16 hours and the reaction mixture is then diluted with ethyl acetate (200 cc). The organic solution is washed with distilled water (5×60 cc), dried over sodium sulphate and concentrated to dryness under reduced pressure (30 mm Hg; 4 kPa) at 35° C. This yields a product (11e) (3.1 g) in the form of a hard orange foam.

Infra-red spectrum (CHBr$_3$), characteristic bands (cm$^{-1}$): 3,400, 1,800, 1,715, 1,590, 1,570, 1,500, 1,450, 1,390, 1,365, 1,040, 960, 755.

Proton NMR spectrum (350 MHz, CDCl$_3$, δ in ppm, J in Hz): 1.48 (s, 9H, (CH$_3$)$_3$C—); 3.20 and 3.94 (2d, J=18, 2H, —S(O)CH$_2$—); 4.53 (d, J=4, 1H, H in the 6-position); 5.78 (d, J=9, 1H, —CONH—); 5.86 (dd, J=4 and 9, 1H, H in the 7-position); 6.45 (d, J=14, 1H, —C$\underline{H}$=CHCl); 7.03 (s, 1H, —CO$_2$CH(C$_6$H$_5$)$_2$); 7.49 (d, J=14, 1H, —CH=C$\underline{H}$Cl); 7.20 to 7.60 (m, 10H, aromatic).

B. A solution of product (11f) (1.09 g), 4-(2,2-dimethoxyethyl)-5,6-dioxo-3-thioxo-perhydro-1,2,4-triazine (0.49 g) and N,N-diisopropylethylamine (0.77 cc) in N,N-dimethylformamide (20 cc) is stirred for 16 hours at 25° C. and 4 hours at 60° C. and then cooled and diluted with methylene chloride (200 cc). The solution obtained is washed successively with a saturated solution of sodium chloride (2×100 cc), a saturated solution of sodium bicarbonate (2×100 cc) and distilled water (2×100 cc) and then dried over sodium sulphate and concentrated to dryness under reduced pressure; the residue is chromatographed on a column of silica gel (0.04–0.06) (diameter of the column: 3 cm; height: 30 cm), elution being carried out with ethyl acetate under a pressure of 50 kPa, and approximately 50 cc fractions being collected. Fractions 7 to 15, containing the pure product, are combined and evaporated to dryness. This yields a product (11d) (0.7 g), the characteristics of which are identical to those of the product described under A.

A solution of the addition compound of chlorine and triphenyl phosphite is prepared by adding a solution of triphenyl phosphite (1.55 g) in methylene chloride (5 cc), in the course of 15 minutes, to a 10% strength (weight/volume) solution of chlorine in methylene chloride (4 cc), cooled to −5° C. This solution is added in the course of 90 minutes, at −10° C., to a solution of 2-benzhydryloxycarbonyl-7-t-butoxycarbonylamino-8-oxo-3-(2-oxoethyl)-5-thia-1-azabicyclo[4.2.0]oct-2-ene (product 11 g) (2.4 g) and pyridine (0.4 cc) in methylene chloride (15 cc). The reaction mixture is washed with distilled water (20 cc), a saturated solution of sodium bicarbonate (20 cc) and distilled water (2×20 cc) and then dried over magnesium sulphate and concentrated to dryness under reduced pressure (30 mm Hg; 4 kPa) at 30° C. This yields an equimolecular mixture (4.6 g) of 2-benzhydryloxycarbonyl-7-t-butoxycarbonylamino-3-(2,2-dichloroethyl)-8-oxo-5-thia-1-azabicyclo[4.2.0]oct-2-ene (product 11h) and triphenyl phosphate. This mixture can be used for the remainder of the synthesis, without additional purification, by redissolving it in dry methylene chloride (15 cc) and by adding a solution of 85% pure metachloroperbenzoic acid (1.22 g) in methylene chloride (30 cc), in the course of 20 minutes, to the above solution, cooled to −10° C. The insoluble material is removed by filtration and the filtrate is washed with a saturated solution of sodium bicarbonate (2×25 cc) and a saturated solution of sodium chloride (2×25 cc) and then dried over magnesium sulphate. The residue obtained after the solvent has been evaporated off under reduced pressure (30 mm Hg; 4 kPa) at 35° C. is chromatographed on a column of silica (0.04–0.06) (diameter of the column: 2 cm; height: 30 cm), elution being carried out with a mixture of cyclohexane and ethyl acetate (60/40 by volume) under 50 kPa, and 30 cc fractions being collected. Fractions 6 to 12 are combined and concentrated to dryness under reduced pressure (30 mm Hg; 4 kPa) at 40° C. This yields a hard yellow foam (1.3 g) mainly consisting of product (11f).

Mass spectrum: molecular peak: m/e=578.

Proton NMR spectrum (350 MHz, CDCl$_3$, δ in ppm, J in Hz): 1.48 (s, 9H, (CH$_3$)$_3$C—); 3.10 (dd, J=5 and 14, 1H, —C$\underline{H}_2$—CHCl$_2$); 3.66 (dd, J=7 and 14, 1H, 2nd H of the —C$\underline{H}_2$—CHCl$_2$); 3.41 and 3.96 (2d, J=18, 2H, —S(O)CH$_2$—); 4.53 (d, J=4, 1H, H in the 6-position); 5.78 (d, J=9, 1H, —CONH—); 5.83 (dd, J=4 and 9, 1H, H in the 7-position); 5.87 (dd, J=5 and 7, 1H, —CH$_2$CHCl$_2$); 6.98 (s, 1H, —CHAr$_2$); 7.2 to 7.5 (m, 10H, aromatic).

The purified product (11h) is obtained by chromatographing an equimolecular mixture (4.6 g) of this product and triphenyl phosphate, as obtained above, on a column of silica gel (0.2–0.06) (30 g), elution being carried out with methylene chloride and 10 cc fractions being collected. Fractions 2 to 11 are combined and concentrated to dryness under reduced pressure (30 mm Hg; 4 kPa) at 30° C. The residue obtained is chromatographed again on a column of silica (0.04–0.06) (diameter of the column: 2 cm; height: 30 cm), elution being carried out with a mixture of cyclohexane and ethyl acetate (80/20 by volume) under 50 kPa, and 10 cc fractions being collected. Fractions 7 and 8, containing the pure product, are concentrated to dryness under reduced pressure (30 mm Hg; 4 kPa) at 35° C. and the product is dried under reduced pressure (0.2 mm Hg; 0.027 kPa) at 25° C.

Mass spectrum: molecular peak: m/e=562.

Proton NMR spectrum (350 MHz, CDCl$_3$, δ in ppm, J in Hz): 1.46 (s, 9H, (CH$_3$)$_3$C—); 3.20 and 3.28 (2dd, J=9 and 14, 2H, —C$\underline{H}_2$CHCl$_2$); 3.65 (limiting AB-type, J=18, 2H, —SCH$_2$—); 5.0 (d, J=4, 1H, H in the 6-position); 5.25 (d, J=9, 1H, —CONH—); 5.67 (dd, J=4 and 9, 1H, H in the 7-position); 5.98 (dd, J=9 and 4, 1H, —CH$_2$—C$\underline{H}$Cl$_2$); 6.95 (s, 1H, —CO$_2$CH(C$_6$H$_5$)$_2$); 7.20 to 7.50 (m, 10H aromatic).

Product (11 g) can be obtained in the following manner:

A solution of the E form of 2-benzhydryloxycarbonyl-7-t-butoxycarbonylamino-3-(2-dimethylaminovinyl)-8-oxo-5-thia-1-azabicyclo[4.2.0]oct-2-ene (product 11i) (1.07 g) in ethyl acetate (10 cc) is stirred for 1 hour, at 25° C., with a 1 N aqueous solution of hydrochloric acid (5 cc). The organic phase is decanted, washed with a saturated aqueous solution of sodium chloride (4×50 cc) and then dried over magnesium sulphate and filtered. After the solvent has been evaporated off to dryness under reduced pressure, a product (1 g) is obtained, the IR spectrum of which shows that it is mainly product (11 g).

Rf=0.57 [silica gel chromatography plate; eluent: 60/40 (by volume) cyclohexane/ethyl acetate].

Infra-red spectrum (CHBr$_3$ solution), characteristice bands (cm$^{-1}$): 2,840, 1,785, 1,720.

Proton NMR spectrum (350 MHz, CDCl$_3$, δ in ppm, J in Hz): 1.47 (s, 9H, (CH$_3$)$_3$C—O—); 3.24 and 3.55 (AB-type, J=18, 2H, —SCH$_2$—); 3.50 and 3.66 (AB-type, J=16, 2H, —C$\underline{H}_2$CHO); 4.98 (d, J=4.5, 1H, H in the 6-position); 5.25 (d, J=9, 1H, —CONH—); 5.65 (dd, J=4.5 and 9, 1H, H in the 7-position); 6.87 (s, 1H, —CO$_2$C$\underline{H}$<); 7.2 to 7.5 (b, 10H, aromatic); 9.54 (s, 1H, —CHO).

Product (11i) can be obtained by following the procedure below:

A solution of 2-benzhydryloxycarbonyl-7-t-butoxycarbonylamino-3-methyl-8-oxo-5-thia-1-azabicyclo[4.2.0]oct-3-ene (product 11j) (1.0 g) in anhydrous N,N-dimethylformamide (100 cc) is heated to 80° C. under a nitrogen atmosphere. Bis-dimethylamino-t-butoxymethane (0.86 cc) is then added rapidly. The reaction mixture is kept at 80° C. for 5 minutes and then poured into ethyl acetate (50 cc). After the addition of distilled water (25 cc), the organic phase is decanted, washed with distilled water (4×25 cc), dried over magnesium sulphate and filtered. The filtrate is concentrated to dryness under reduced pressure (20 mm Hg;

2.7 kPa) at 30° C. and this yields a product (1.10 g), mainly consisting of product (11i), in the form of a hard orange foam.

Rf=0.29; silica gel chromatography plate [50/50 (by volume) cyclohexane/ethyl acetate].

Infra-red spectrum (CHBr$_3$), characteristic bands (cm$^{-1}$): 3,430, 3,350, 2,820, 1,765, 1,715, 1,690, 1,615, 1,540, 1,505, 1,495, 1,465, 1,370, 1,240, 940, 745, 600.

UV/visible spectrum in ethanol: λmax=390 nm, ε=29,000 (c=2.10$^{-5}$ M).

Mass spectrum: molecular peak=535; characteristic fragments: m/e=378 and 379 (scission of the δ-lactam).

Proton NMR spectrum (350 MHz, CDCl$_3$, δ in ppm, J in Hz): 1.48 (s, (CH$_3$)$_3$C—OCO—, 9H); 2.89 (s, 6H, (CH$_3$)$_2$N—); 3.17 (AB-type, J=14, 2H, —S—CH$_2$— of the cephem); 5.02 (d, J=4, 1H, H in the 6-position); 5.27 (dd, J=4 and 9, 1H, H in the 7-position); 5.60 (d, J=9, 1H, —OCONH—); 6.71 (d, J=14, 1H, —CH═CH—N<); 6.49 (d, J=14, 1H, —CH═CH—N<); 6.95 (s, 1H, —CH(C$_6$H$_5$)$_2$); 7.2 to 7.5 (b, aromatic, 10H).

The product (11j) can be prepared by esterifying 7-t-butoxycarbonylamino-2-carboxy-3-methyl-8-oxo-5-thia-1-azabicyclo[4.2.0]oct-3-ene (product 11k) (3.2 g) with diphenyldiazomethane (2.1 g) at between 25° and 30° C. for 16 hours. After recrystallisation from a 90/10 (by volume) cyclohexane/ethyl acetate mixture, a product (11j) (2.3 g) is obtained in the form of white crystals (m.p.=161° C.)

Product (11k) can be prepared by converting 7-t-butoxycarbonylamino-2-methoxycarbonyl-3-methyl-8-oxo-5-thia-1-azabicyclo[4.2.0]oct-2-ene (product 11l) (8.28 g), using the method of R. B. Morin et al., J. Amer. Chem. Soc., 91 (6), 1,401 (1969). This yields a product (11k) (5.4 g).

M.p.=200° C. (decomposition) (after recrystallisation from ethyl acetate).

Rf=0.59 [silica gel chromatography plate; eluent: 60/20/1/1 (by volume) ethyl acetate/acetone/water/formic acid mixture].

Product (11l) can be prepared by esterifying 7-t-butoxycarbonylamino-2-carboxy-3-methyl-8-oxo-5-thia-1-azabicyclo[4.2.0]oct-2-ene (product 11m) (16.7 g) with a solution of diazomethane in ether, according to R. B. Morin et al., J. Amer. Chem. Soc., 91 (6), 1,401 (1969). This yields a product (11l) (13.6 g) in the form of white crystals (m.p.=148° C.).

Rf=0.45 [silica gel chromatography plate; eluent: 60/40 (by volume) cyclohexane/ethyl acetate].

Product (11m) can be prepared in the following manner:

7-Amino-2-carboxy-3-methyl-8-oxo-5-thia-1-azabicyclo[4.2.0]oct-2-ene (371 g) is dissolved in a solution of sodium bicarbonate (307 g) in a mixture of distilled water (2 liters) and dioxane (2 liters). A solution of di-t-butyl pyrocarbonate (421 g) in dioxane (2 liters) is added in the course of 10 minutes. The reaction mixture is stirred for 48 hours at 25° C. The suspension obtained is concentrated under reduced pressure (20 mm Hg; 2.7 kPa), at 50° C., to a residual volume of about 2 liters and then diluted with ethyl acetate (1 liter) and distilled water (2 liters). The aqueous phase is decanted, washed with ethyl acetate (500 cc) and acidified to pH=2 with 6 N hydrochloric acid, in the presence of ethyl acetate (1,500 cc). The aqueous phase is extracted with ethyl acetate (2×1 liter). The combined organic phases are washed with a saturated solution of sodium chloride (2×250 cc) and dried over sodium sulphate. After filtration, the solvent is evaporated off under reduced pressure (20 mm Hg; 2.7 kPa) at 50° C. This yields 7-t-butoxycarbonylamino-2-carboxy-3-methyl-8-oxo-5-thia-1-azabicyclo[4.2.0]oct-2-ene (486 g) in the form of yellow crystals (m.p.=190° C., decomposition).

EXAMPLE 12

A solution of the E form of the syn isomer of 2-benzhydryloxycarbonyl-3-(2-chlorovinyl)-7-[2-methoxyimino-2-(2-tritylaminothiazol-4-yl)-acetamido]-8-oxo-5-thia-1-azabicyclo[4.2.0]oct-2-ene-5-oxide (product 12a) (0.9 g), 1-(2,2-diethoxyethyl)-5,6-dioxo-4-methyl-3-thioxo-perhydro-1,2,4-triazine (0.23 g) and N,N-diisopropylethylamine (0.19 cc) in N,N-dimethylformamide (10 cc) is stirred for 16 hours at 25° C. and then 4 hours at 60° C. and then cooled and diluted with methylene chloride (100 cc). The solution obtained is washed succesuvely with a saturated solution of sodium chloride (2×50 cc), a saturated solution of sodium bicarbonate (2×50 cc) and distilled water (2×50 cc) and then dried over sodium sulphate and concentrated to dryness under reduced pressure (30 mm Hg; 4 kPa) at 30° C. The residue is chromatographed on a column of silica gel (0.04–0.06) (diameter of the column: 3 cm; height: 30 cm), elution being carried out with a mixture of cyclohexane and ethyl acetate (25/75 by volume) (2.5 liters) under a pressure of 50 kPa, and 50 cc fractions being collected. Fractions 19 to 42, containing the pure product, are combined and concentrated to dryness. This yields the E form of the syn isomer of 2-benzhydryloxycarbonyl-3-{2-[1-(2,2-diethoxyethyl)-5,6-dioxo-4-methyl-1,4,5,6-tetrahydro-1,2,4-triazin-3-yl]-thiovinyl}-7-[2-methoxyimino-2-(2-tritylaminothiazol-4-yl)-acetamido]-8-oxo-5-thia-1-azabicyclo[4.2.0]oct-2-ene-5-oxide (product 12b) (0.8 g), the characteristics of which are identical to those of product (9b) obtained in Example 9.

By following the procedure described in Example 9, followed by reduction and removal of the protective radicals, the E form of the syn isomer of 7-[2-(2-aminot hiazol-4-yl)-2-methoxyiminoacetamido]-2-carboxy-3-[2-(5,6-dioxo-1-formylmethyl-4-methyl-1,4,5,6-tetrahydro-1,2,4-triazin-3-yl)-thiovinyl]-8-oxo-5-thia-1-azabicyclo[4.2.0]oct-2-ene (product 12) is obtained, the characteristics of which are described in Example 9, product (9).

Product (12a) can be obtained in the following manner:

A solution of para-toluenesulphonic acid (hydrate) (2.2 g) in acetonitrile (15 cc) is added, in the course of 15 minutes, to a solution of the E form of 2-benzhydryloxycarbonyl-7-t-butoxycarbonylamino-3-(2-chlorovinyl)-8-oxo-5-thia-1-azabicyclo[4.2.0]oct-2-ene-5-oxide (product 12c) (3.4 g) in acetonitrile (15 cc) at 40° C. After 30 minutes at 40° C., the reaction mixture is concentrated to dryness under reduced pressure (30 mm Hg; 4 kPa) at 30° C. The residue is taken up in ethyl acetate (100 cc) and the solution obtained is washed with a saturated solution of sodium bicarbonate (2×50 cc) and distilled water (2×50 cc) and then dried over sodium sulphate and concentrated to dryness under reduced pressure (30 mm Hg; 4 kPa) at 35° C. The residue is dried under reduced pressure (0.2 mm Hg; 0.03 kPa) at 25° C. for 1 hour. This yields crude E form of 7-amino-2-benzhydryloxycarbonyl-3-(2-chlorovinyl)-8-oxo-5-thia-1-azabicyclo[4.2.0]oct-2-ene-5-oxide (product 12d) (2.5 g) in the form of a hard orange foam. This product is redissolved in dry methylene chloride (45 cc), a solution of 2-methoxyimino-2-

(2-tritylaminothiazol-4-yl)acetic acid (syn isomer) (2.5 g) and 4-dimethylaminopyridine (0.03 g) in dry methylene chloride (30 cc) is added and N,N'-dicyclohexylcarbodiimide (1.3 g) and dry methylene chloride (10 cc) are then added (after cooling to about 4° C.) The reaction mixture is stirred for 40 minutes at about 6° C. and then 16 hours at 25° C. The precipitate of N,N'-dicyclohexylurea is filtered off and rinsed with dry methylene chloride (2×5 cc). The filtrate and the combined washings are concentrated to dryness under reduced pressure (30 mm Hg; 4 kPa) at 30° C. and the residue obtained is taken up in ethyl acetate (200 cc). The solution obtained is washed successively with 0.2 N hydrochloric acid (50 cc), a semisaturated solution of sodium bicarbonate (2×50 cc) and a saturated solution of sodium chloride (50 cc) and then dried over sodium sulphate. The residue obtained after evaporation to dryness under reduced pressure (30 mm Hg; 4 kPa) at 30° C. is chromatographed on a column of silica (0.04–0.06) (diameter of the column: 4 cm, height: 30 cm), elution being carried out with methylene chloride (800 cc) and then with a mixture of methylene chloride and ethyl acetate (95/5 by volume) (1,200 cc) under a pressure of 50 kPa, and 60 cc fractions being collected. Fractions 12 to 25, containing the pure product, are combined and concentrated to dryness under reduced pressure. This yields a product (12a) (1.7 g) in the form of a hard cream-coloured foam.

Infra-red spectrum (CHBr₃), characteristic bands (cm⁻¹): 3,380, 2,820, 1,800, 1,725, 1,680, 1,595, 1,585, 1,570, 1,515, 1,495, 1,450, 1,210, 1,040, 930, 750.

Proton NMR spectrum (350 MHz, CDCl₃, δ in ppm, J in Hz): 3.22 and 3.92 (2d, J=18, 2H, —S—CH₂—); 4.12 (s, 3H, =N—O—CH₃); 4.63 (d, J=5, 1H, —H in the 6-position); 6.21 (dd, J=5 and 9, 1H, —H in the 7-position); 6.44 and 7.50 (2d, J=14, 2H, —CH=CHCl); 6.74 (s, 1H, —H of the thiazole); 7.01 (s, 1H, —COO—CH(C₆H₅)₂); 7.11 (b, 1H, —NH—C(C₆H₅)₃); 7.2 to 7.6 (m, aromatic); 7.54 (d, J=9, =CO—NH—).

Product (12c) can be obtained as described above in Example 11 (product 11e).

EXAMPLE 13

N,N-Diisopropylethylamine (0.04 cc) is added to a solution of the syn isomer of 2-benzhydryloxycarbonyl-3-(2,2-dichloroethyl)-7-[2-methoxyimino-2-(2-tritylaminothiazol-4-yl)-acetamido]-8-oxo-5-thia-1-azabicyclo[4.2.0]oct-2-ene-5-oxide (product 13a) (0.09 g) and 1-(2,2-diethoxyethyl)-5,6-dioxo-4-methyl-3-thioxo-perhydro-1,2,4-triazine (0.03 g) in dry N,N-dimethylformamide (2 cc) and the reaction mixture is stirred for 16 hours at 25° C. and then 4 hours at 60° C. Chromatographic examination shows the formation of the E form of the syn isomer of 2-benzhydryloxycarbonyl-3-{2-[1-(2,2-diethoxyethyl)-5,6-dioxo-4--methyl-1,4,5,6-tetrahydro-1,2,4-triazin-3-yl]-thiovinyl}-7-[2-methoxyimino-2-(2-tritylaminothiazol-4-yl)-acetamido]-8-oxo-5-thia-1-azabicyclo[4.2.0]oct-2-ene-5-oxide (product 13 b).

Rf=0.3 [Merck silica gel chromatography plate; eluent: 20/80 (by volume) mixture of cyclohexane and ethyl acetate].

By following the procedure of Example 9, and after reduction and removal of the protective radicals, the E form of the syn isomer of 7-[2-(2-aminothiazol-4-yl)-2--methoxyiminoacetamido]-2-carboxy-3-[2-(5,6-dioxo-1-formylmethyl-4-methyl-1,4,5,6-tetrahydro-1,2,4-triazin-3-yl)-thiovinyl]-8-oxo-5-thia-1-azabicyclo[4.2.0]oct-2-ene (product 13) is obtained, identical with product (9).

Product (13a) can be obtained in the following manner:

Following the procedure described in Example 11B, a solution of the syn isomer of 2-benzhydryloxycarbonyl-7-[2-methoxyimino-2-(2-tritylaminothiazol-4-yl)-acetamido]-8-oxo-3-(2-oxoethyl)-5-thia-1-azabicyclo[4.2.0]oct-2-ene (product 13c) (2.3 g) in methylene chloride (15 cc), cooled to −40° C., is treated with a 0.5 M solution (5.5 cc), in methylene chloride, of the addition compound of chlorine and triphenyl phosphite. The reaction mixture is stirred for 3 hours at a temperature between −40° C. and −20° C. and then diluted with ethyl acetate (200 cc). The organic solution is decanted and washed with a semisaturated solution of sodium bicarbonate and sodium chloride (50 cc) and then a saturated solution of sodium chloride (3×50 cc). The aqueous phases are reextracted with ethyl acetate (50 cc) and the combined organic solutions are concentrated to dryness under reduced pressure (30 mm Hg; 4 kPa) at 30° C. The residue is stirred with isopropyl ether (150 cc) for 16 hours. The precipitate is filtered off, washed with isopropyl ether (50 cc) and then redissolved in methylene chloride (50 cc) and fixed to silica gel (0.2–0.06) (8 g), which is deposited on a column of silica gel (0.06–0.04) (diameter of the column: 1.8 cm; height: 35 cm). Elution is carried out with a mixture of cyclohexane and ethyl acetate (75/25 by volume) under a pressure of 80 kPa, 50 cc fractions being collected. Fractions 5 to 7, containing the pure product, are combined and concentrated to dryness under reduced pressure (30 mm Hg; 4 kPa) at 30° C. This yields the syn isomer of 2-benzhydryloxycarbonyl-3-(2,2-dichloroethyl)-7-[2-methoxyimino-2-(2-tritylaminothiazol-4-yl)-acetamido]-8-oxo-5-thia-1-azabicyclo[4.2.0]oct-2-ene (product 13d) (0.25 g) in the form of a whitish solid.

Proton NMR spectrum (350 MHz, CDCl₃, δ in ppm, J in Hz): 3.17+3.33 (2dd, J=14 and 9+J=14 and 5, 2H, exo—CH₂); 3.62 (limiting AB-type, J=18, 2H, —CH₂—S—); 4.08 (s, 3H, =N—O—CH₃); 5.06 (d, J=5, 1H, —H in the 6-position); 5.94 to 6 (m, 2H, —H in the 7-position and —CHCl₂); 6.76 (s, 1H, —H of the thiazole); 6.8 (d, J=9, 1H, —CO—NH—); 6.92 (s, 1H, —COO—CH(C₆H₅)₂); 7.04 (b, 1H, —NH—C(C₆H₅)₃); 7.15 to 7.5 (m, aromatic).

A solution of 85% pure meta-chloroperbenzoic acid (0.05 g) in methylene chloride (1 cc) is added all at once to a solution, cooled to −10° C., of product (13d) (0.2 g) in methylene chloride (5 cc). After 30 minutes at −10° C., the reaction mixture is diluted with ethyl acetate (20 cc) and washed with a saturated solution of sodium bicarbonate (2×10 cc) and a saturated solution of sodium chloride (2×10 cc). After the organic phase has been dried over sodium sulphate and concentrated to dryness under reduced pressure (30 mm Hg; 4 kPa) at 30° C., a crude product (13a) (0.15 g) is obtained in the form of a hard orange foam.

Proton NMR spectrum (350 MHz, CDCl₃, δ in ppm, J in Hz): 3.14+3.56 (2dd, J=15 and 5+J=15 and 7, 2H, exo—CH₂); 3.39 and 3.96 (2d, J=18, 2H,

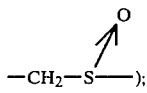

4.09 (s, 3H, =N—O—CH₃); 4.58 (d, J=5, 1H, —H in the 6-position); 5.87 (dd, J=5 and 7, 1H, —CHCl₂); 6.19 (dd, J=5 and 9, 1H, —H in the 7-position); 6.72 (s, 1H, —H of the thiazole); 6.94 (s, 1H, —COO—CH(C₆H₅)₂); 7.08 (b, 1H, —NH—C(C₆H₅)₃); 7.10 to 7.60 (m, aromatic+—CO—NH).

EXAMPLE 14

Following the procedure described in Example 1 (by treating the E form of the syn isomer) of 2-benzhydryloxycarbonyl-7-[2-t-butoxycarbonylmethoxyimino-2-(2-t ritylaminothiazol-4-yl)acetamido]-3-{2-[1-(2,2-diethoxyethyl)-5,6-dioxo-4-methyl-1,4,5,6-tetrahydro-1,2,4-triazin-3-yl]-thiovinyl}-8-oxo-5-thia-1-azabicyclo[4.2.0]oct-2-ene (1.9 g) successively with trifluoroacetic acid (19 cc) and with a mixture of formic acid (19 cc) and water (9.5 cc), there is obtained the E form of the syn isomer of 7-[2-(2-aminothiazol-4-yl)-2-carboxymethoxyiminoacetamido]-2-carboxy-3-[2-(5,6-dioxo-1-formylmethyl-4-methyl-1,4,5,6-tetrahydro-1,2,4-triazin-3-yl)-thiovinyl]-8-oxo-5-thia-1-azabicyclo[4.2.0]oct-2-ene (0.75 g) in the form of a yellow powder.

Infra-red spectrum (KBr), characteristic bands (cm⁻¹): 3600, 2200, 1775, 1705, 1675, 1580, 1405, 945.

The E form of the syn isomer of 2-benzhydryloxycarbonyl-7-[2-t-butoxycarbonylmethoxyimino-2-(2-t ritylaminothiazol-4-yl)acetamido]-3-{2-[1-(2,2-diethoxyethyl)-5,6-dioxo-4-methyl-1,4,5,6-tetrahydro-1,2,4-triazin-3-yl]-thiovinyl}-8-oxo-5-thia-1-azabicyclo[4.2.0]oct-2-ene may be obtained in the following manner:

The E form of the syn isomer of 2-benzhydryloxycarbonyl-7-[2-t-butoxycarbonylmethoxyimino-2-(2-t ritylaminothiazol-4-yl)acetamido]-3-{2-[1-(2,2-diethoxyethyl)-5,6-dioxo-4-methyl-1,4,5,6-tetrahydro-1,2,4-triazin-3-yl]-thiovinyl}-8-oxo-5-thia-1-azabicyclo[4.2.0]oct-2-ene 5-oxide (2.9 g) is reduced (as described in Example 1) in a mixture of dichloromethane (80 cc) and dimethylacetamide (0.889 cc) with phosphorus trichloride (0.428 cc). After chromatography on a column of Merck silica gel (0.06–0.2) (60 g) (diameter of the column: 2 cm), eluting with a 35/65 (by volume) cyclohexane/ethyl acetate mixture (600 cc) and collecting fractions of 60 cc, fractions 3 to 9 are evaporated to dryness to yield the E form of the syn isomer of 2-benzhydryloxycarbonyl-7-[2-butoxycarbonylmethoxyimino-2-(2-t ritylaminothiazol-4-yl)acetamido]-3-{2-[1-(2,2-diethoxyethyl)-5,6-dioxo-4-methyl-1,4,5,6-tetrahydro-1,2,4-triazin-3-yl]-thiovinyl}-8-oxo-5-thia-1-azabicyclo[4.2.0]oct-2-ene (1.9 g) in the form of a hard yellow foam.

Infra-red spectrum (CHBr₃), characteristic bands (cm⁻¹): 3380, 3260, 1770, 1720, 1680, 1585, 1525, 1490, 1450, 1095, 1065, 940, 750, 735.

Proton NMR spectrum (350 MHz, CDCl₃, δ in ppm, J in Hz) 1.16 (t, J=7, 6H, —CH₃); 1.42 (s, 9H, —C(CH₃)₃); 3.43 (s, 3H, >N—CH₃); 3.5 to 3.8 (m, 6H, (—OCH₂CH₃)₂ and —SCH₂—); 4.07 (d, J=5, 2H, >N—CH₂—); 4.74 and 4.86 (2d, J=16, 2H, —OCH₂COO—); 4.91 (t, J=5, 1H,

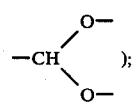

5.11 (d, J=4.5, 1H, H in the 6-position); 5.92 (dd, J=4.5 and 9, 1H, H in the 7-position); 6.81 (d, J=16, 1H, —CH=CHS—); 6.83 (s, 1H, H of the thiazole); 6.95 (s, 1H, —COOCH—); 7 (s broad, 1H, —NHC(C₆H₅)₃); 8.75 (d, J=9, 1H, —CONH—).

The E form of the syn isomer of 2-benzhydryloxycarbonyl-7-[2-t-butoxycarbonylmethoxyimino-2-(2-t ritylaminothiazol-4-yl)-acetamido]-3-{2-[1-(2,2-diethoxyethyl)-5,6-dioxo-4-methyl-1,4,5,6-tetrahydro-1,2,4-triazin-3-yl]thiovinyl}-8-oxo-5-thia-1-azabicyclo[4.2.0]oct-2-ene 5-oxide may be obtained in the following manner:

The E form of the syn isomer of 2-benzhydryloxycarbonyl-7-[2-t-butoxycarbonylmethoxyimino-2-(2-tritylaminothiazol-4-yl)acetamido]-8-oxo-3-(2-tosyloxyvinyl)-5-thia-1-azabicyclo[4.2.0]oct-2-ene 5-oxide (3.3 g) is treated (as described in Example 1) in solution in dimethylformamide (60 cc) with 1-(2,2-diethoxyethyl)-5,6-dioxo-3-mercapto-4-methyl-1,4,5,6-tetrahydro-1,2,4-triazine (0.864 g) in the presence of diisopropylethylamine (0.552 cc). After chromatography on a column of Merck silica gel (0.06–0.2) (200 g) (diameter of the column: 2.2 cm) eluting with a 20/80 (by volume) cyclohexane-ethyl acetate mixture (600 cc) and evaporating to dryness, fractions 4 to 9 (each of 60 cc) the E form of the syn isomer of 2-benzhydryloxycarbonyl-7-[2-t-butoxycarbonylmethoxyimino-2-(2-tritylaminothiazol-4-yl)acetamido]-3-{2-[1-(2,2-diethoxyethyl)-5,6-dioxo-4-methyl-1,4,5,6-tetrahydro-1,2,4-triazin-3-yl]-thiovinyl}-8-oxo-5-thia-1-azabicyclo[4.2.0]oct-2-ene 5-oxide (2.9 g) in the form of a hard yellow foam is obtained.

Infra-red spectrum (CHBr₃), characteristic bands (cm⁻¹): 3380, 3240, 1805, 1720, 1680, 1580, 1520, 1490, 1445, 1390, 1370, 1060, 940, 750, 735.

Proton NMR spectrum (350 MHz, CDCl₃, δ in ppm, J in Hz): [1.17 (t, J=7) and 1.18 (t, J=7); 6H, —CH₃]; 1.44 (s, 9H, —C(CH₃)₃); 3.22 and 4.02 (2d, J=18, 2H, —SCH₂—); 3.43 (s, 1H, >N—CH₃); 3.53 (m, 2H, OCH₂CH₃); 3.72 (m, 2H, —OCH₂CH₃); 4.07 (m, 2H, >NCH₂—); 4.64 (d, J=4.5, 1H, H in the 6-position); 3.72 and 3.79 (2d, J=16, 2H, =NOCH₂—); 4.91 (t, J=5, 1H,

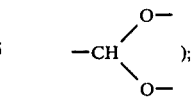

6.06 (dd, J=4.5 and 9, 1H, H in the 7-position); 6.78 (s, 1H, H of the thiazole); 6.82 (d, J=16, 1H, —CH=C-HS—); 6.97 (s, 1H, —COOCH<); 7.03 (s broad, 1H, —NHC(C₆H₅)₃); 8.37 (d, J=9, 1H, —CONH—).

The present invention also relates to the medicaments which contain, as the active product, at least one product of the general formula (I) in the pure form (in the free form or in the form of a salt) or in the form of a composition in association with one or more pharmaceutically acceptable adjuvants. These medicaments can be administered orally, parenterally (in particular intramuscularly or intravenously) or rectally.

Tablets, pills, powders (generally presented in capsules, e.g. gelatin capsules) or granules can be used as solid compositions for oral administration. In these compositions, the active product according to the invention is mixed with one or more inert diluents or adjuvants such as sucrose, lactose or starch. These compositions can also comprise substances other than diluents, e.g. a lubricant such as magnesium stearate.

Solutions, suspensions, syrups, elixirs containing inert diluents such as water or paraffin oil, and pharmaceutically acceptable emulsions can be used as liquid compositions for oral administration. These compositions can also comprise substances other than diluents, e.g. wetting, sweetening or flavouring products.

The compositions for parenteral administration can be suspensions, emulsions or aqueous or non-aqueous sterile solutions. Propylene glycol, a polyethylene glycol, vegetable oils, in particular olive oil, and injectable organic esters, e.g. ethyl oleate, can be employed as the solvent or vehicle. These compositions can also contain adjuvants, in particular wetting, emulsifying or dispersing agents. Sterilisation can be carried out in several ways, e.g. with the aid of a bacteriological filter, by incorporating sterilising agents into the composition, by irradiation or by heating. The compositions can also be prepared in the form of sterile solid compositions which are to be dissolved, at the time of use, in sterile water or any other injectable sterile medium.

The compositions for rectal administration are suppositories which can contain, in addition to the active product, excipients such as cacao butter or semi-synthetic glycerides.

In human therapy, the medicaments according to the present invention are particularly useful in the treatment of infections of bacterial origin.

In general, the physician will determine the posology which he considers to be most appropriate as a function of the age, the weight, the degree of infection and the other factors peculiar to the subject to be treated. Adult doses are generally between 1 and 10 g of active product per day, administered intramuscularly.

The following example, which is given without implying a limitation, illustrates a composition according to the present invention.

EXAMPLE

An isotonic aqueous solution (100 cc), containing sodium bicarbonate (2.63 g) and, as the active product, the E form of the syn isomer of 7-[2-(2-aminothiazol-4-yl)-2-carboxymethoxyiminoacetamido]-2-carboxy-3-[2-(5,6-dioxo-4-formylmethyl-1,4,5,6-tetrahydro-1,2,4-triazin-3-yl)-thiovinyl]-8-oxo-5-thia-1-azabicyclo[4.2.-0]oct-2-ene (free aldehyde) (10 g), is prepared. After filtration on a bacteriological filter, this solution is divided up under aseptic conditions into ampoules (at a rate of 10 cc per ampoule) and lyophilised and the ampoules are sealed.

Each ampoule contains the equivalent of 1 g of the active product in the form of the aldehyde hydrate of its disodium salt.

We claim:
1. A 3-thiovinylcephalosporin of the formula:

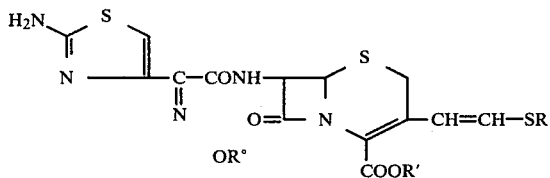

in which:
α. the symbol R is chosen from amongst the following meanings:
(1) alkyl, L-2-amino-2-carboxyethyl or phenyl,
(2) pyrid-2-yl, pyrid-3-yl or pyrid-4-yl and their N-oxides,
(3) pyrimidin-2-yl, pyridazin-3-yl substituted in the 6-position (by an alkyl, methoxy, amino or alkanoylamino radical) and optionally N-oxidised, or tetrazolo[4,5-b]pyridazin-6-yl,
(4) 5,6-dioxo-1,4,5,6-tetrahydro-1,2,4-triazin-3-yl substituted in the 4-position, or 1,3,4-triazol-5-yl or 2-alkoxycarbonyl-1,3,4-triazol-5-yl substituted in the 1-position, by
(a) an alkyl radical which is unsubstituted or substituted by an alkoxy, alkylthio, phenyl, formyl, carbamoyl, alkylcarbamoyl, dialkylcarbamoyl, alkanoyl (containing 2 to 4 carbon atoms), alkoxycarbonyl or thiazolidin-2-yl radical,
(b) an allyl, 2,3-dihydroxypropyl, 1,3-dihydroxyprop-2-yl, 2-formyl-2-hydroxyethyl, 3-formyloxy-2-hydroxypropyl, 2,3-bis-formyloxypropyl or 1,3-bis-formyloxyprop-2-yl radical,
(c) an alkyl radical containing 2 to 4 carbon atoms, which is substituted by a hydroxyl or carbamoyloxy radical, an alkanoyloxy radical (the alkanoyl part of which can be substituted by an amino, alkylamino or dialkylamino radical), an alkylsulphinyl, alkylsulphonyl, amino, alkylamino, dialkylamino, sulphoamino, alkylsulphonylamino or sulphamoylamino radical, an alkanoylamino radical (the alkanoyl part of which is optionally substituted by hydroxyl, amino, alkylamino or dialkylamino) or an alkoxycarbonylamino, ureido, alkylureido or dialkylureido radical,
(d) a radical corresponding to one of the formulae:

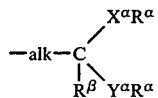

or

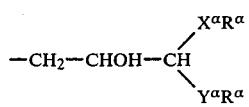

or

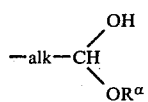

in which alk is an alkylene radical containing 1 to 4 carbon atoms, $X^\alpha$ and $Y^\alpha$ are identical and represent oxygen or sulphur atoms and $R^\alpha$ represents an alkyl radical, or alternatively $X^\alpha$ and $Y^\alpha$ are identical or different and represent oxygen or sulphur atoms and the radicals $R^\alpha$ together form an alkylene radical containing 2 or 3 carbon atoms, and $R^\beta$ represents a hydrogen atom or an alkyl radical containing 1 to 3 carbon atoms, or
(e) an alkyl radical containing 2 to 5 carbon atoms, which is substituted by an alkoxyimino or hydroxyimino radical,
(5) 1,4-dialkyl-5,6-dioxo-1,4,5,6-tetrahydro-1,2,4-triazin-3-yl, 1-alkyl-5,6-dioxo-1,4,5,6-tetrahydro-1,2,4-triazin-3-yl or 2-alkyl-5,6-dioxo-1,2,5,6-tetrahydro-1,2,4-triazin-3-yl, (6) 1,3,4-triazol-5-yl, 1,2,3-triazol-5-yl or 1-alkyl-1,2,4-triazol-5-yl which is unsubstituted or substituted in the 3-position by alkoxycarbonyl, (7) (a) 1,3,4-thiadiazol-5-yl which is unsubstituted or substituted by an alkyl, trifluoromethyl, alkoxy or alkylthio radical, a hydroxyalkylthio radical, the alkyl part of which contains 2 to 4 carbon atoms, or an alkylsulphonyl, hydroxyl, hydroxyalkyl, carboxyl, carboxyalkyl, amino, alkylamino, dialkylamino, aminoalkyl, alkylaminoalkyl, dialkylaminoalkyl, alkanoylamino or alkanoylaminoalkyl radical, or (b) 1,2,4-thiadiazol-5-yl substituted by an alkyl or alkoxy radical, (8) (a) 1,3,4-oxadiazol-5-yl which is unsubstituted or substituted by an alkyl, trifluoromethyl, phenyl, aminoalkyl, alkylaminoalkyl, dialkylaminoalkyl or alkanoylaminoalkyl radical, or (b) oxazol-2-yl or 4-alkyloxazol-2-yl, and (9) tetrazol-5-yl which is unsubstituted or substituted in the 1-position by (a) an alkyl radical which is unsubstituted or substituted by alkoxy, sulpho, carboxyl, formyl or sulphamoyl, (b) an alkyl radical containing 2 to 4 carbon atoms, which is substituted by hydroxyl, amino, alkylamino, dialkylamino, alkanoylamino, carboxyalkylamino, sulphamoylamino, sulphoamino, ureido, alkylureido or dialkylureido, (c) an alkyl radical containing 2 to 5 carbon atoms, which is substituted by hydroxyimino or alkoxyimino, (d) a phenyl, 2,3-dihydroxypropyl, 1,3-dihydroxyprop-2-yl, 2-formyl-2-hydroxyethyl, 3-formyloxy-2-hydroxypropyl, 2,3-bis-formyloxypropyl or 1,3-bis-formyloxyprop-2-yl radical, or (e) a radical of the formulae:

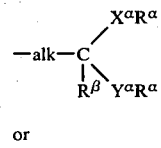

or

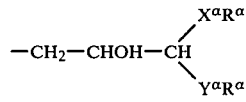

in which $R^\beta$ is a hydrogen atom and $X^\alpha$, $Y^\alpha$ and $R^\alpha$ are defined as under (4d) above, and the symbol R° represents a carboxyalkyl radical of the formula:

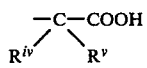

in which the radicals $R^{iv}$ and $R^v$, which are identical or different, represent hydrogen atoms or alkyl radicals, or together form an alkylene radical containing 2 or 3 carbon atoms, or alternatively β. the symbol R is chosen from amongst:

1. 5,6-dioxo-1,4,5,6-tetrahydro-1,2,4-triazin-3-yl substituted in the 1-position, 5,6-dioxo-1,2,5,6-tetrahydro-1,2,4-triazin-3-yl substituted in the 2-position, or 1,2,4-triazol-5-yl or 3-alkoxycarbonyl-1,2,4-triazol-5-yl substituted in the 1-position, by (a) an alkyl radical which is itself substituted by an alkoxy, alkylthio, phenyl, formyl, carbamoyl, alkylcarbamoyl or dialkylcarbamoyl radical, a hydroxyalkylcarbamoyl radical (the alkyl part of which contains 2 to 4 carbon atoms) or an alkanoyl (containing 2 to 4 carbon atoms), alkoxycarbonyl or thiazolidin-2-yl radical, (b) an allyl, 2,3-dihydroxypropyl, 1,3-dihydroxyprop-2-yl, 2-formyl-2-hydroxyethyl, 3-formyloxy-2-hydroxypropyl, 2,3-bis-formyloxypropyl or 1,3-bis-formyloxyprop-2-yl radical, (c) an alkyl radical containing 2 to 4 carbon atoms, which is substituted by a hydroxyl or carbamoyloxy radical, an alkanoyloxy radical (the alkanoyl part of which can be substituted by an amino, alkylamino or dialkylamino radical), an alkylsulphinyl, alkylsulphonyl, amino, alkylamino, dialkylamino, sulphoamino, alkylsulphonylamino or sulphamoylamino radical, an alkanoylamino radical (the alkanoyl part of which is optionally substituted by hydroxyl, amino, alkylamino or dialkylamino) or an alkoxycarbonylamino, ureido, alkylureido or dialkylureido radical, (d) a radical corresponding to one of the formulae mentioned above under (α. 4d), or (e) an alkyl radical containing 2 to 5 carbon atoms, which is substituted by an alkoxyimino or hydroxyimino radical, 2. 5,6-dioxo-4-hydroxyalkylcarbamoylalkyl-1,4,5,6-tetrahydro-1,2,4-triazin-3-yl, the hydroxyalkyl portion of which contains 2 to 4 carbon atoms, and 3. 1-alkyl-5,6-dioxo-1,4,5,6-tetrahydro-1,2,4-triazin-3-yl substituted in the 4-position, 1-alkyl-5,6-dioxo-1,2,5,6-tetrahydro-1,2,4-triazin-3-yl substituted in the 2-position, 2-alkyl-5,6-dioxo-1,2,5,6-tetrahydro-1,2,4-triazin-3-yl substituted in the 1-position, or 4-alkyl-5,6-dioxo-1,4,5,6-tetrahydro-1,2,4-triazin-3-yl substituted in the 1-position, by a formylalkyl radical or by a radical of the formula:

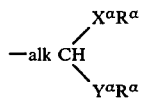

in which alk, $X^\alpha$, $Y^\alpha$ and $R^\alpha$ are defined as above, and the symbol R° represents a hydrogen atom, an alkyl, vinyl or cyanomethyl radical or a radical of the formula:

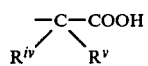

as defined above, and the symbol R' represents a hydrogen atom or a radical which can easily be removed by an enzymatic method, of the formula:

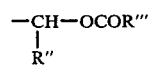

in which R" represents a hydrogen atom or an alkyl radical and R'" represents an alkyl radical or the cyclohexyl radical, it being understood that the alkyl or alkanoyl radicals and portions mentioned above are linear or branched (unless otherwise mentioned) and contain (unless otherwise mentioned) 1 to 4 carbon atoms, in its syn or anti forms and E or Z forms, and mixtures thereof, and also its addition salts with acids, its metal salts and its addition salts with nitrogen-containing bases.

2. A 3-thiovinylcephalosporin as claimed in claim 1 in which R is pyrimidin-2-yl, 5,6-dioxo-1,4,5,6-tetrahydro-1,2,4-triazin-3-yl substituted in the 4-position by formylmethyl or by 2,3-dihydroxypropyl, or tetrazol-5-yl substituted in the 1-position by alkyl and R° represents a carboxyalkyl radical of the formula

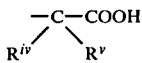

in which the radicals $R^{iv}$ and $R^v$ which are identical or different represent hydrogen or alkyl or together form an ethylene or trimethylene chain, or R is 5,6-dioxo-4-hydroxyalkylcarbamoylalkyl-1,4,5,6-tetrahydro-1,2,4-triazin-3-yl in which the hydroxyalkyl contains 2 to 4 carbon atoms, 1-alkyl-4-formylalkyl-5,6-dioxo-1,4,5,6-tetrahydro-1,2,4-triazin-3-yl, or 1-formylalkyl-4-alkyl-5,6-dioxo-1,4,5,6-tetrahydro-1,2,4-triazin-3-yl, and R° represents alkyl or a carboxyalkyl radical of the formula:

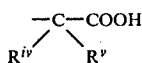

in which the radicals $R^{iv}$ and $R^v$ are as hereinbefore defined, the aforesaid alkyls containing (unless otherwise stated) 1 to 4 carbon atoms.

3. 7-[2-(2-Aminothiazol-4-yl)-2-carboxymethoxyiminoacetamido]-2-carboxy-3-[2-(5,6-dioxo-4-formylmethyl-1,4,5,6-tetrahydro-1,2,4-triazin-3-yl)-thiovinyl]-8-oxo-5-thia-1-azabicyclo-[4.2.0]oct-2-ene, in its syn or anti forms and E or Z forms, and mixtures thereof, and its addition salts with acids, its metal salts and its addition salts with nitrogen-containing bases.

4. 7-[2-(2-Aminothiazol-4-yl)-2-carboxymethoxyiminoacetamido]-2-carboxy-3-{2-[4-(2,3-dihydroxypropyl)-5,6-dioxo-1,4,5,6-tetrahydro-1,2,4-triazin-3-yl]-thiovinyl}-8-oxo-5-thia-1-azabicyclo[4.2.0]oct-2-ene, in its syn or anti forms and E or Z forms, and mixtures thereof, and its addition salts with acids, its metal salts and its addition salts with nitrogen-containing bases.

5. 7-[2-(2-Aminothiazol-4-yl)-2-carboxymethoxyiminoacetamido]-2-carboxy-3-[2-(1-methyltetrazol-5-yl)-thiovinyl]-8-oxo-5-thia-1-azabicyclo[4.2.0]oct-2-ene, in its syn or anti forms and E or Z forms, and mixtures thereof, and its addition salts with acids, its metal salts and its addition salts with nitrogen-containing bases.

6. 7-[2-(2-Aminothiazol-4-yl)-2-carboxymethoxyiminoacetamido]-2-carboxy-3-[2-(pyrimidin-2-yl)-thiovinyl]-8-oxo-5-thia-1-azabicyclo[4.2.0]oct-2-ene, in its syn or anti forms and E or Z forms, and mixtures thereof, and its addition salts with acids, its metal salts and its addition salts with nitrogen-containing bases.

7. 7-{2-(2-Aminothiazol-4-yl)-2-[(2-carboxyprop-2-yl)-oxyimino]-acetaido}-2-carboxy-3-[2-(5,6-dioxo-4-formylmethyl-1,4,5,6-tetrahydro-1,2,4-triazin-3-yl)-thiovinyl]-8-oxo-5-thia-1-azabicyclo[4.2.0]oct-2-ene, in its syn or anti forms and E or Z forms, and mixtures thereof, and its addition salts with acids, its metal salts and its addition salts with nitrogen-containing bases.

8. 7-{2-(2-Aminothiazol-4-yl)-2-[(2-carboxyprop-2-yl)-oxyimino]-acetamido}-2-carboxy-3-[2-(1-methyltetrazol-5-yl)-thiovinyl]-8-oxo-5-thia-1-azabicyclo[4.2.0]oct-2-ene, in its syn or anti forms and E or Z forms, and mixtures thereof, and its addition salts with acids, its metal salts and its addition salts with nitrogen-containing bases.

9. 7-[2-(2-Aminothiazol-4-yl)-2-(1-carboxycyclobutoxyimino)-acetamido]-2-carboxy-3-[2-(5,6-dioxo-4-formylmethyl-1,4,5,6-tetrahydro-1,2,4-triazin-3-yl)thiovinyl]-8-oxo-5-thia-1-azabicyclo[4.2.0]oct-2-ene, in its syn or anti forms and E or Z forms, and mixtures thereof, and its addition salts with acids, its metal salts and its addition salts with nitrogen-containing bases.

10. 7-[2-(2-Aminothiazol-4-yl)-2-methoxyiminoacetamido]-2-carboxy-3-{2-{5,6-dioxo-4-[N-(2-hydroxyethyl)carbamoylmethyl]-1,4,5,6-tetrahydro-1,2,4-triazin-3-yl}thiovinyl}-8-oxo-5-thia-1-azabicyclo-[4.2.0]-oct-2-ene, in its syn or anti forms and E or Z forms, and mixtures thereof, and its addition salts with acids, its metal salts and its addition salts with nitrogen-containing bases.

11. 7-[2-(2-Aminothiazol-4-yl)-2-methoxyiminoacetamido]-2-carboxy-3-[2-(5,6-dioxo-1-formylmethyl-4-methyl-1,4,5,6-tetrahydro-1,2,4-triazin-3-yl)-thiovinyl]-8-oxo-5-thia-1-azabicyclo[4.2.0]oct-2-ene, in its syn or anti forms and E or Z forms, and mixtures thereof, and its addition salts with acids, its metal salts and its addition salts with nitrogen-containing bases.

12. 7-[2-(2-Aminothiazol-4-yl)-2-methoxyiminoacetamido]-2-carboxy-3-[2-(5,6-dioxo-4-formylmethyl-1-methyl-1,4,5,6-tetrahydro-1,2,4-triazin-3-yl)-thiovinyl]-8-oxo-5-thia-1-azabicyclo[4.2.0]oct-2-ene, in its syn or anti forms and E or Z forms, and mixtures thereof, and its addition salts with acids, its metal salts and its addition salts with nitrogen-containing bases.

13. 7-[2-(2-Aminothiazol-4-yl)-2-carboxymethoxyiminoacetamido]-2-carboxy-3-[2-(5,6-dioxo-1-formylmethyl-4-methyl-1,4,5,6-tetrahydro-1,2,4-triazin-3-yl)-thiovinyl]-8-oxo-5-thia-1-azabicyclo[4.2.0]oct-2-ene, in its syn or anti forms and E and Z forms, and mixtures thereof and its addition salts with acids, its metal salts and its addition salts with nitrogen-containing bases.

14. The E form of the syn isomer of a compound as claimed in any one of claims 1 and 2 to 13.

15. A pharmaceutical antibacterial composition which comprises an antibacterial amount of a compound according to claim 1 in association with one or more compatible and pharmaceutically acceptable diluents or adjuvants.

16. Method of treating a bacterial infection which comprises administering to a subject suffering therefrom or subject thereto an effective amount of a cephalosporin compound according to claim 1.

* * * * *